United States Patent [19]
Rohrberg

[11] Patent Number: 5,979,457
[45] Date of Patent: Nov. 9, 1999

[54] ULTRASONIC FLOATATION-ENHANCED BODY IMAGING SYSTEM

[76] Inventor: Roderick G. Rohrberg, 2742 W. 234th St., Torrance, Calif. 90505

[21] Appl. No.: 08/744,347
[22] Filed: Nov. 7, 1996
[51] Int. Cl.⁶ .................................................... A61B 8/00
[52] U.S. Cl. ............................................................. 128/915
[58] Field of Search .................................... 128/660, 630, 128/660.09, 915

[56] References Cited

U.S. PATENT DOCUMENTS

| | | | |
|---|---|---|---|
| 4,252,125 | 2/1981 | Iinuma | 128/660 |
| 4,434,799 | 3/1984 | Taenzer | 128/660 |
| 4,545,385 | 10/1985 | Pirschel | 128/660 |
| 5,474,064 | 12/1995 | Rohrberg | 128/630 |
| 5,572,995 | 11/1996 | Rohrberg | 128/630 |
| 5,664,573 | 9/1997 | Shmulewitz | 128/660.09 |

*Primary Examiner*—William E. Kamm
*Assistant Examiner*—Maulin Patel
*Attorney, Agent, or Firm*—Anglin & Giaccherini

[57] ABSTRACT

"Methods and apparatus for producing enhanced ultrasound images of portions of the human body while utilizing the beneficial effects of floatation are disclosed." Although the method is especially useful for generating images of the female breast, tissues of the male abdomen and testicles may also be imaged using the present invention. In the preferred embodiment of the invention, a patient relaxes while substantially immersed in hot water. When the breast is submerged, the buoyancy of the breast tissue in the water counteracts the effects of gravity. The buoyancy of the water enhances the capacity of an ultrasound sensor which is also submerged to form an image of the body tissues which may be employed to detect abnormalities.

22 Claims, 61 Drawing Sheets

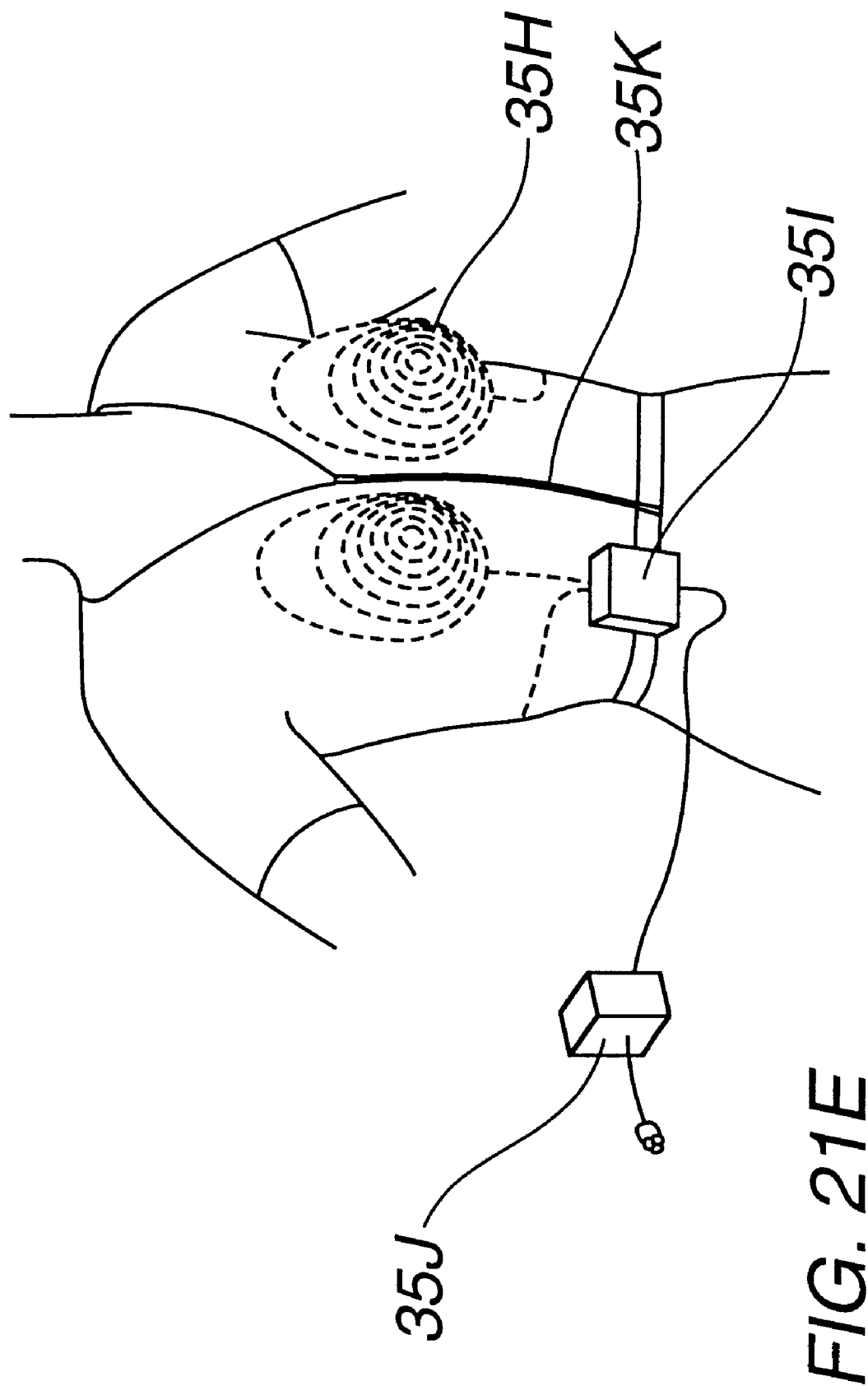

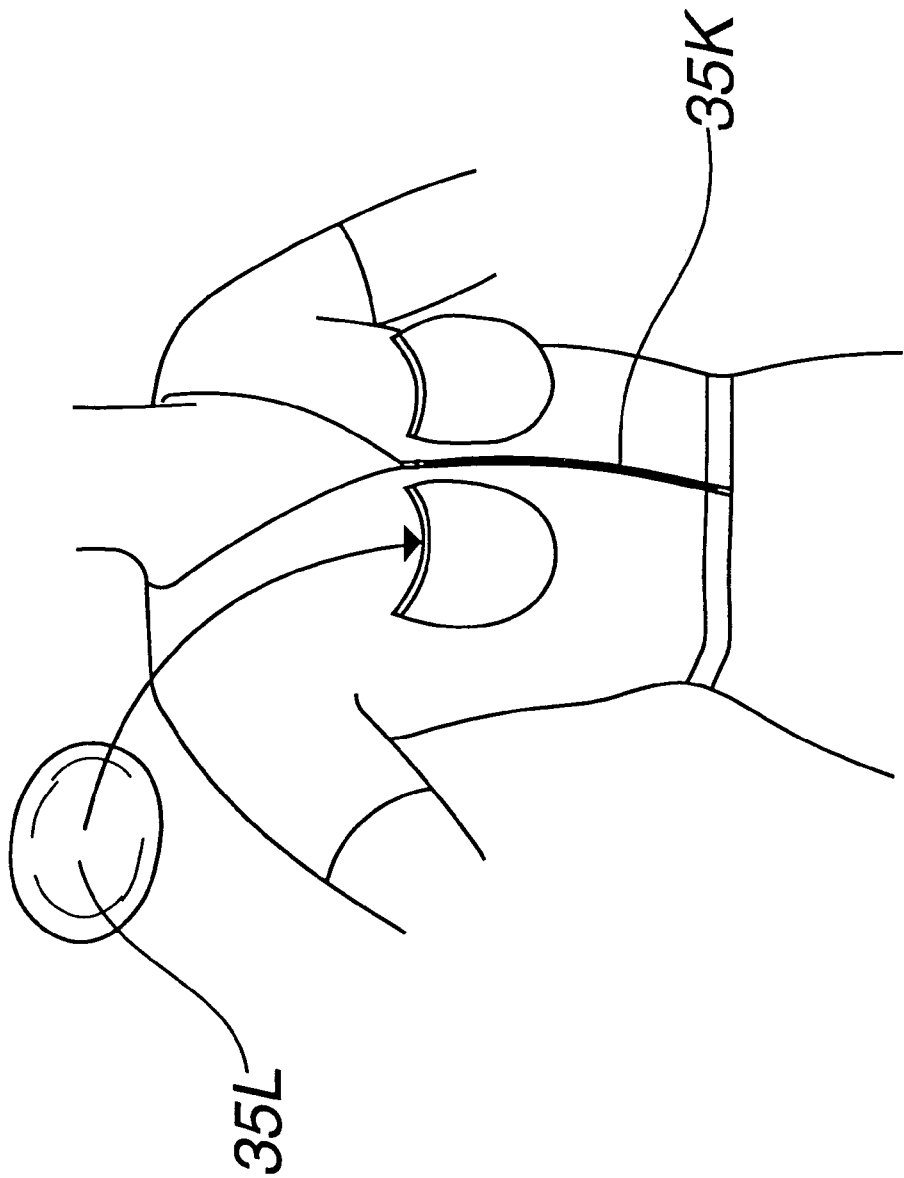

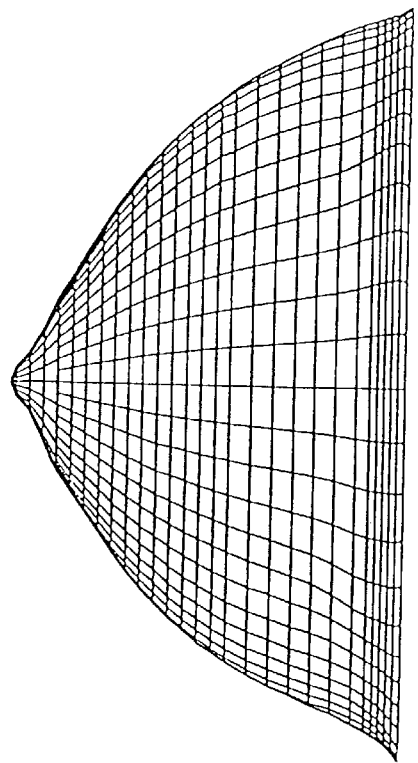
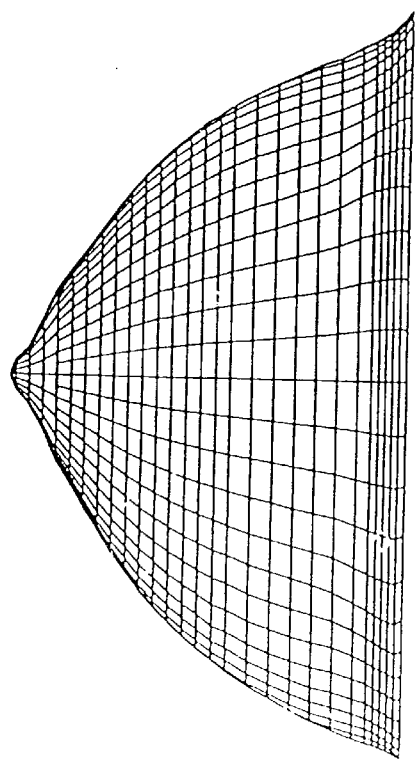
FIG. 59

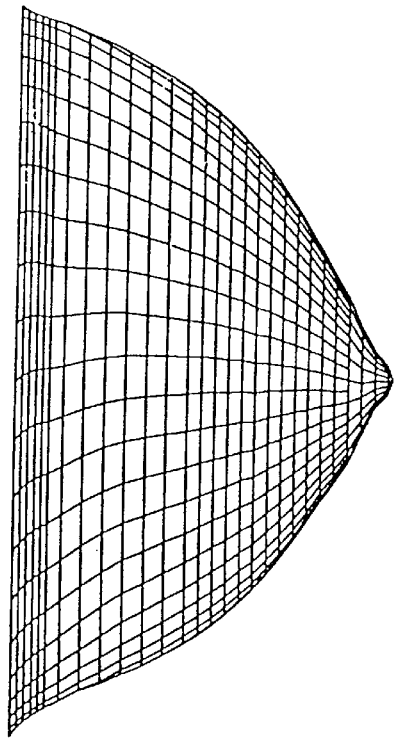
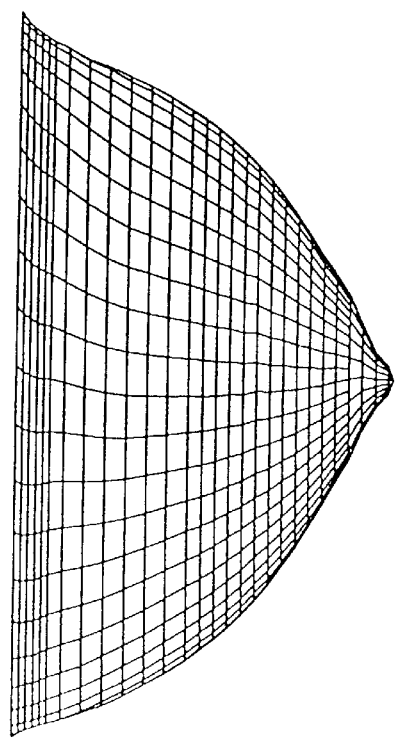
FIG. 60

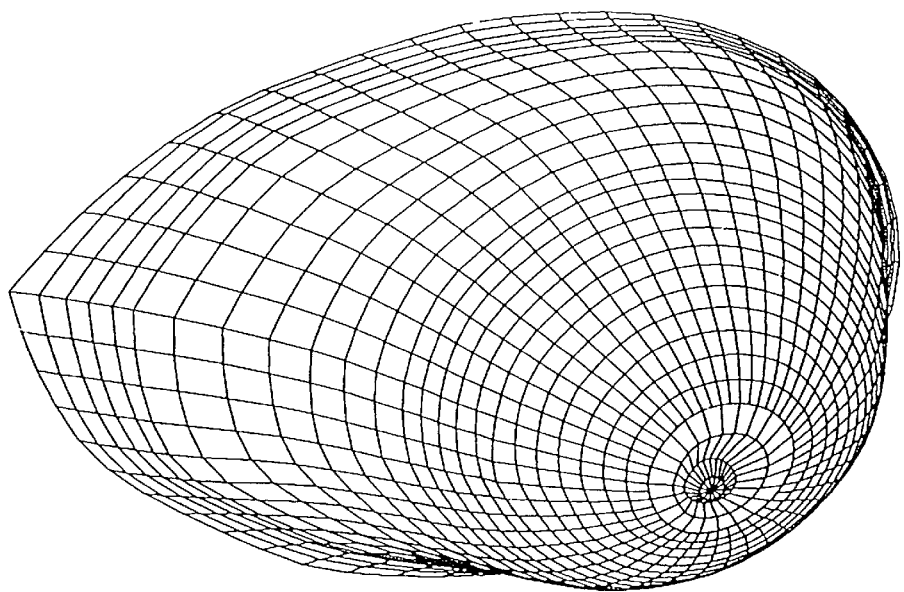
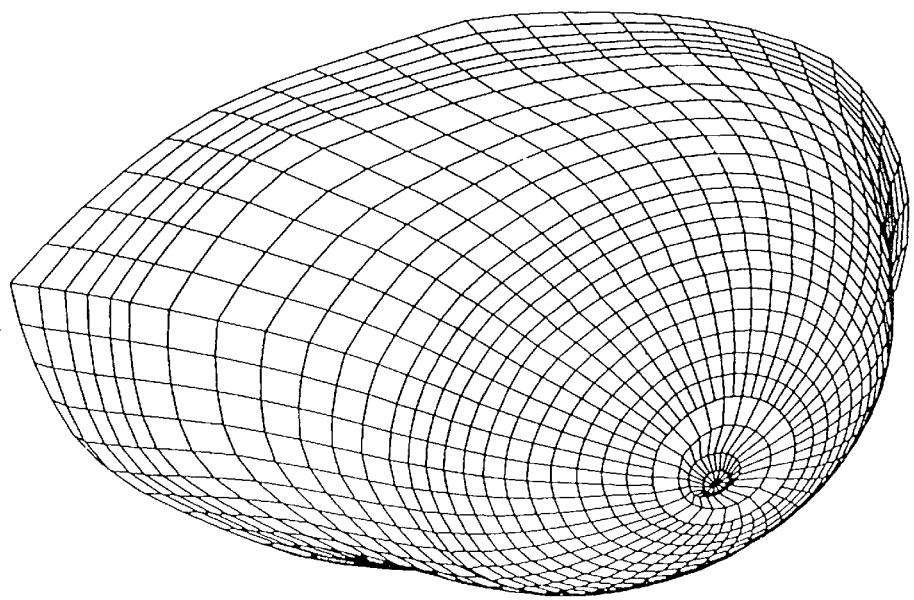
FIG. 62

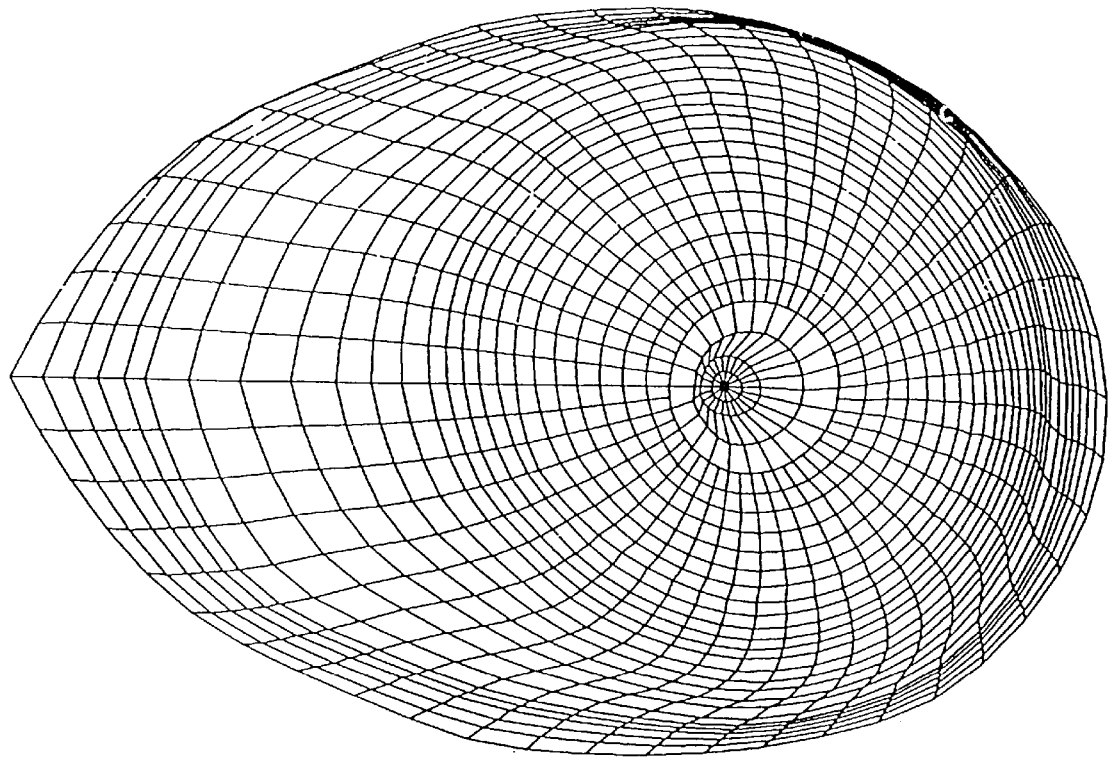
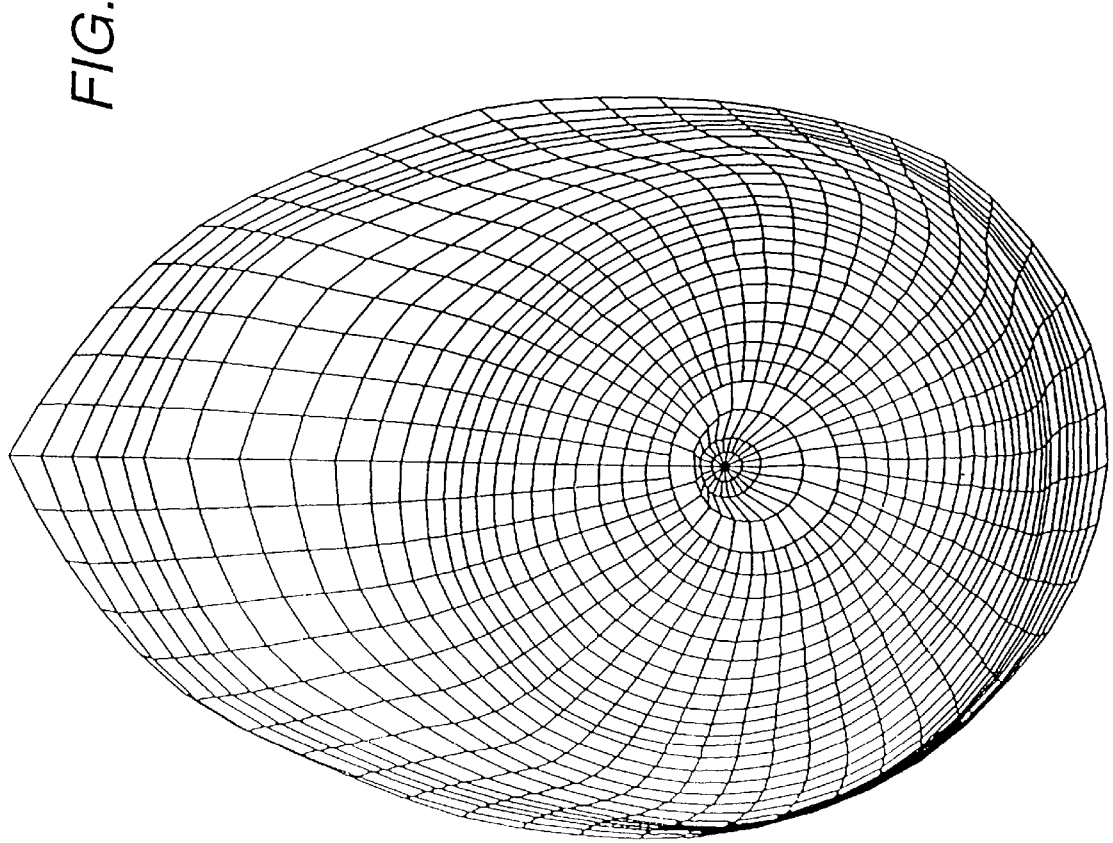
FIG. 63

FIG. 66

BUST MOLD MEASUREMENTS
DIGITIZED NUMBERS OF MOLD
RADIAL POSITION - 30° INCREMENTS

BUST MOLD #1
LEFT BREAST

| ELEVATION | 0° (NIPPLE) | 30° | 60° | 90° | 120° | 150° | 180° | 210° | 240° | 270° | 300° | 330° | 360° |
|---|---|---|---|---|---|---|---|---|---|---|---|---|---|
| .000 | .272 | .240 | .225 | .215 | .204 | .174 | .175 | .185 | .190 | .201 | .233 | .266 | .272 |
| .100 | .583 | .545 | .446 | .346 | .277 | .229 | .213 | .246 | .290 | .368 | .467 | .549 | .578 |
| .200 | .841 | .800 | .687 | .576 | .484 | .418 | .403 | .426 | .483 | .590 | .694 | .785 | .841 |
| .300 | 1.039 | .986 | .863 | .739 | .670 | .605 | .573 | .573 | .651 | .742 | .857 | .971 | 1.038 |
| .400 | 1.206 | 1.145 | 1.029 | .918 | .838 | .780 | .741 | .729 | .777 | .872 | 1.001 | 1.133 | 1.205 |
| .500 | 1.346 | 1.286 | 1.182 | 1.087 | 1.032 | .957 | .905 | .879 | .915 | 1.010 | 1.164 | 1.297 | 1.353 |
| .600 | 1.486 | 1.410 | 1.314 | 1.249 | 1.205 | 1.146 | 1.070 | 1.019 | 1.053 | 1.148 | 1.314 | 1.436 | 1.490 |
| .700 | 1.609 | 1.521 | 1.440 | 1.389 | 1.358 | 1.312 | 1.220 | 1.161 | 1.172 | 1.281 | 1.443 | 1.573 | 1.608 |
| .800 | 1.722 | 1.623 | 1.549 | 1.523 | 1.513 | 1.466 | 1.376 | 1.292 | 1.284 | 1.396 | 1.563 | 1.686 | 1.722 |
| .900 | 1.818 | 1.715 | 1.650 | 1.638 | 1.640 | 1.610 | 1.515 | 1.147 | 1.398 | 1.506 | 1.673 | 1.788 | 1.820 |
| 1.000 | 1.904 | 1.793 | 1.744 | 1.743 | 1.768 | 1.744 | 1.649 | 1.529 | 1.503 | 1.609 | 1.756 | 1.868 | 1.905 |
| 1.100 | 1.981 | 1.866 | 1.831 | 1.840 | 1.882 | 1.871 | 1.777 | 1.647 | 1.608 | 1.699 | 1.852 | 1.953 | 1.980 |
| 1.200 | 2.040 | 1.939 | 1.912 | 1.928 | 1.973 | 1.983 | 1.890 | 1.754 | 1.690 | 1.782 | 1.928 | 2.012 | 2.042 |
| 1.300 | 2.096 | 2.004 | 1.984 | 1.997 | 2.062 | 2.092 | 2.010 | 1.854 | 1.783 | 1.857 | 1.994 | 2.083 | 2.097 |
| 1.400 | 2.144 | 2.058 | 2.056 | 2.084 | 2.140 | 2.202 | 2.135 | 1.962 | 1.867 | 1.924 | 2.061 | 2.140 | 2.143 |
| 1.500 | 2.209 | 2.143 | 2.150 | 2.180 | 2.259 | 2.358 | 2.327 | 2.123 | 1.979 | 2.014 | 2.149 | 2.209 | 2.205 |
| 1.650 | 2.260 | 2.213 | 2.242 | 2.265 | 2.359 | 2.511 | 2.548 | 2.289 | 2.077 | 2.093 | 2.219 | 2.270 | 2.257 |
| 1.800 | 2.299 | 2.285 | 2.318 | 2.348 | 2.456 | 2.678 | 2.795 | 2.482 | 2.189 | 2.159 | 2.281 | 2.317 | 2.299 |
| 1.950 | 2.333 | 2.340 | 2.385 | 2.423 | 2.550 | 2.864 | 3.113 | 2.690 | 2.291 | 2.231 | 2.347 | 2.370 | 2.333 |
| 2.100 | 2.365 | 2.377 | 2.442 | 2.487 | 2.633 | 3.074 | 3.474 | 2.946 | 2.403 | 2.287 | 2.400 | 2.420 | 2.368 |
| 2.250 | 2.427 | 2.475 | 2.476 | 2.544 | 2.722 | 3.316 | 3.810 | 3.229 | 2.517 | 2.368 | 2.458 | 2.487 | 2.427 |
| 2.400 | 2.482 | 2.471 | 2.496 | 2.572 | 2.787 | 3.509 | 3.975 | 3.412 | 2.615 | 2.418 | 2.508 | 2.586 | 2.486 |
| 2.500 | 2.527 | 2.498 | 2.507 | 2.584 | 2.830 | 3.613 | 4.040 | 3.492 | 2.669 | 2.447 | 2.534 | 2.583 | 2.527 |
| 2.550 | 2.577 | 2.528 | 2.522 | 2.600 | 2.872 | 3.710 | 3.937 | 3.577 | 2.720 | 2.478 | 2.565 | 2.615 | 2.573 |
| 2.600 | — | 2.567 | 2.530 | 2.611 | 2.908 | 3.791 | 4.168 | 3.668 | 2.801 | 2.517 | 2.599 | 2.659 | — |
| 2.650 | — | 2.593 | 2.543 | 2.628 | 2.964 | 3.868 | 4.203 | 3.762 | 2.882 | 2.559 | 2.633 | 2.715 | — |
| 2.700 | — | 2.620 | 2.557 | 2.642 | 3.013 | 3.902 | 4.239 | 3.852 | 2.992 | 2.606 | 2.679 | 2.762 | — |
| 2.750 | — | — | — | — | — | — | — | 3.941 | 3.136 | 2.668 | 2.729 | 2.810 | — |
| 2.800 | — | — | — | — | — | — | — | — | — | — | — | — | — |

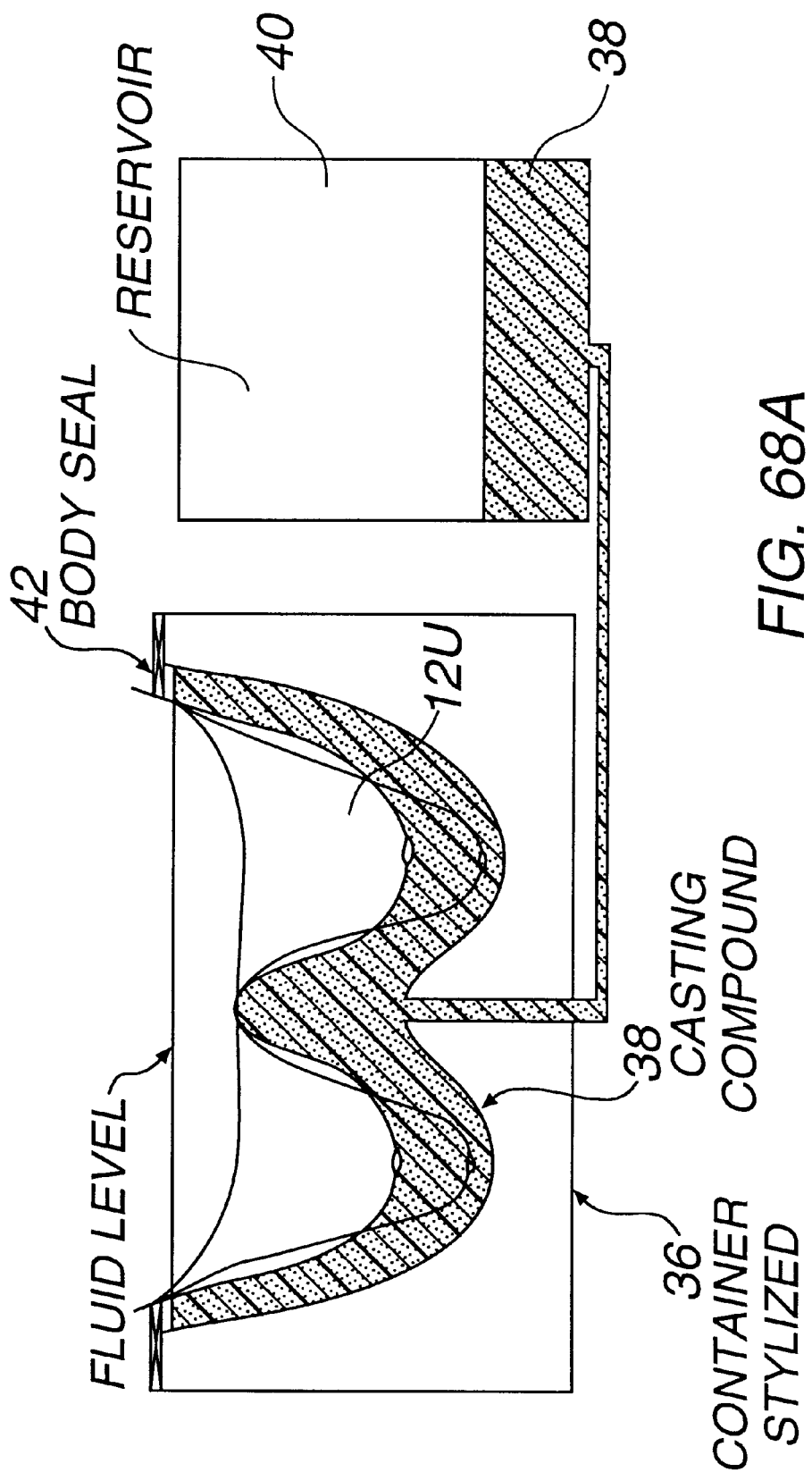

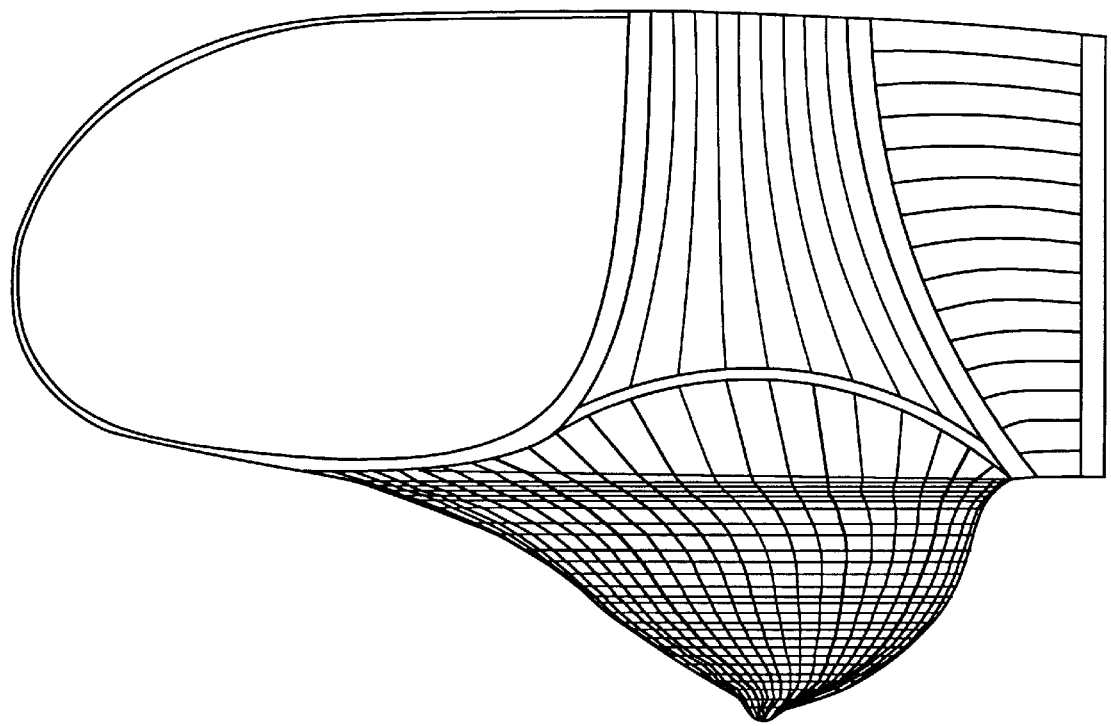

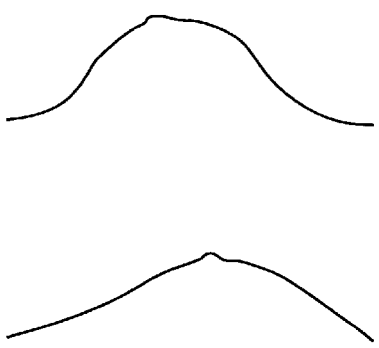
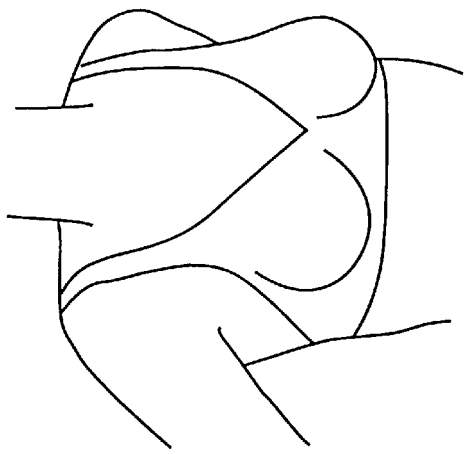
FIG. 75
PADDED PRESENT BRAS
NON-PADDED PRESENT BRAS
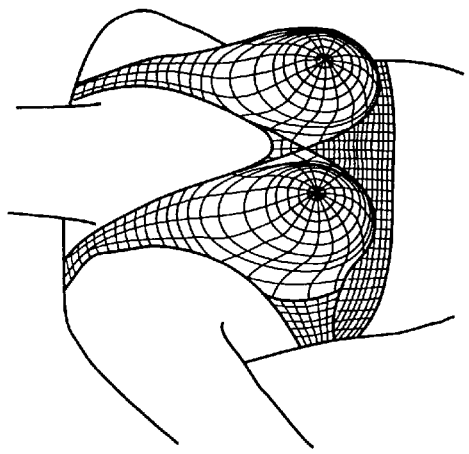
FIG. 74
PERFECT WAY NATURAL SHAPE BRA

ULTRASONIC FLOATATION-ENHANCED BODY IMAGING SYSTEM

CROSS-REFERENCES TO RELATED U.S. PATENTS

The present Patent Application is related to a commonly-owned U.S. Pat. No. 5,474,064 entitled *Breast Self-Examination Floatation System* by Roderick G. Rohrberg, which was granted on Dec. 12, 1995. The present Patent Application is also related to a commonly-owned U.S. Pat. No. 5,572,995 entitled *Floatation Enhanced Self-Examination System*, which will be granted on Nov. 12, 1996.

FIELD OF THE INVENTION

The present invention pertains to forming images of various parts of the human body immersed in a water bath using an ultrasonic sensor. More particularly, the present invention utilizes fingertip ultrasound sensors to produce images of portions of the body while the patient relaxes in a bath. The buoyant forces of the water levitate the portions of the body which are probed, and enhance the imaging capacities of the ultrasonic detector.

BACKGROUND OF THE INVENTION

According to a recent study by the American Cancer Society, 46,000 women in the United States will die in 1993 from breast cancer. (From the 1993 *World Almanac*, published by Pharos Books.) Recent advances in diagnostic techniques and surgical treatments have helped to reduce the mortality rate due to breast cancer, but this disease is still the third greatest cause of death among women in this country. A variety of mammographic systems which employ X-rays and ultrasound have been developed over the past few decades, but this equipment is generally very large, prohibitively expensive and requires a trained technician to operate them. As an example, the minimum price of an ultrasonic imaging system sold by Acuson of Mountain View, Calif. exceeds $200,000. Several documents noted below disclose various systems that pertain to equipment that may be used for different kinds of medical diagnosis.

In U.S. Pat. No. 4,282,880, Gardineer et al. disclose a water conditioning system for maintaining and conditioning the water used in an ultrasound imaging system especially adapted to perform diagnosis of the human breast.

In his U.S. Pat. No. 4,737,109, Abramson discloses a method and apparatus for use in training persons in breast cancer detection by manual examination. The apparatus includes a device which is comprised of a body of elastomerically yielding material and one or more lumps embedded in the body, wherein the lump or lumps resemble a pre-determined type of lesion.

In their U.S. Pat. No. 4,793,354, Wright and Perry disclose a method of enhancing the sense of touch.

In his U.S. Pat. No. 4,867,686, Goldstein uses a model of a human female breast for teaching breast examination. Goldstein discloses a method of training a person to detect breast tumors by palpating a model of a human female breast having at least one simulated tumor.

In his U.S. Pat. No. 5,207,582, Michelson discusses a device for facilitating breast self-examination in order to speed up detection of breast cancer. The device has an information panel, instructions for conducting self-examinations and diagrams for recording the results. Recording means are also included with this device.

In their U.S. Pat. No. 5,479,661, Fingleson and Richman teach the use a garment worn by a woman for self-examination of the breasts, the device having written and graphic instructions printed on it.

In his U.S. Pat. No. 4,130,112, Frazer describes an apparatus for ultrasonic scanning of a breast or other tissue. This invention includes a cavity for receiving the patient's breast, and a vacuum for drawing the breast into intimate contact with the walls of the cavity. The walls enclose ultrasonic transducers that are employed to create an image of the breast tissue.

U.S. Pat. No. 4,135,497 issued to Meyers et al. reveals an apparatus for detecting temperature variations over selected regions of living tissue. The inventors state that the method disclosed in their patent is useful for detecting malignant tissue in the breasts.

U.S. Pat. No. 4,206,763 issued to Pedersen discloses a device and a method for ultrasonic examination for carcinoma of the breast. Pedersen employs a compartment in which water is drawn upward by suction over the breast. An ultrasonic transducer then revolves around the breast to obtain complete 360 degree scans. A pleated flexible bag 12 pulls the breast into a water bath compartment 4 when the water bath compartment 4 is evacuated by a pair of bellows 16. (See Column 1, Lines 60–68; Column 3, Lines 23–51 and Column 4, Lines 4 & 5.)

U.S. Pat. No. 4,252,125 issued to Iinuma describes an ultrasonic diagnosing apparatus that utilizes a receptacle 11 filled with warm water 12. An ultrasonic probe 14 makes an image of the breasts, which are pressed against a flexible membrane 18 that is stretched in front of the probe. (See Column 1, Lines 65–68 and Column 2, Lines 1–7.)

U.S. Pat. No. 4,341,222 issued to Gardineer et al. relates to a patient support system for orienting a woman's breast over an ultrasound scanner. The patient is shown bent over a pool of water 20 that is positioned over a scanning transducer 14. (See Column 5, Lines 62–68 and Column 6, Lines 1–4.) The water serves as a transmission medium for the ultrasonic waves. (See Column 2, Lines 15 & 16.)

U.S. Pat. No. 4,347,850 issued to Kelly-Fry et al. discloses a direct water coupling device for ultrasound scanning. A tank 10 is placed in a sealed position about the perimeter of the breast area while the patient is in a supine position. (See FIG. 3 & Column 4, Lines 37–38.)

U.S. Pat. No. 4,545,385 issued to Pirschel describes an apparatus for ultrasonic examination of body parts using a fluid container and an ultrasound scanning system. (See FIG. 1.) A liquid-filled basin 6 serves as an acoustic coupling. (See Column 3, Lines 4–5 & Column 3, Lines 24–25.)

U.S. Pat. No. 4,657,021 issued to Perry et al. concerns an apparatus which he claims enhances the sense of touch when placed between the fingertips of the user and the object being touched. A liquid lubricant 13 is captured inside a sealed enclosure 10 made from a pliable, elastic material. (See Column 2, Lines 36–40 and Column 3, Lines 4–18.)

U.S. Pat. No. 4,873,982 issued to Morrison contains an discussion of an examination garment that may be used to feel for lumps under the skin. (See FIGS. 1 and 3.)

U.S. Pat. No. 4,917,096 issued to Englehart et al. reveals the details of a portable ultrasonic probe. A fluid-filled enclosure is coupled to a handled portion which houses a drive motor. (See FIG. 3.) The probe 20 includes a fluid-filled enclosure 34. (See Column 4, Lines 30–31.)

U.K. Patent Application No. 2,111,347A by Robert Cribbs pertains to a method of pulse examination using a container that holds a liquid couplant. The container is placed about the breasts of a female torso, and breast tissue is scanned using ultrasound.

A brochure published by Metrix Incorporated of Deerfield, Ill. presents specifications for echo-scan and echo-trace ultrasonic analyzers. The brochure describes how high frequency, short duration electromechanical pulses emitted by special transducers in direct or indirect contact with a portion of the human body can produce visual information.

In her book entitled *Dr. Susan Love's Breast Book,* Susan M. Love describes conventional techniques for breast self-examinations. (See pp. 21–31).

The vast majority of literature published in both the academic and popular press suggests that the best weapon in the fight against breast cancer is early detection. The problem of providing a low-cost yet effective method of producing diagnostic images of portions of the human body has presented a major challenge to doctors and other health-care professionals. The development of methods and apparatus that enhance the prospects of detecting abnormalities during examinations would constitute a major technological advance and would satisfy a long felt need within the health-care field.

SUMMARY OF THE INVENTION

The *Ultrasonic Floatation-Enhanced Body Imaging System* comprises apparatus and methods for generating images of portions of the human body utilizing the beneficial effects of floatation. The method is especially useful for producing ultrasound images of the female breast. In the preferred embodiment of the invention, a patient relaxes in a tub filled with hot water. The physical relaxation created by the bath brings about a concomitant state of mental relaxation. When the breast is substantially submerged, the buoyancy of the breast tissue in the water counteracts the effects of gravity. The buoyancy of the water allows the breast to assume its natural shape and position, and consequently enhances the quality of images generated by an ultrasonic detector which is also immersed in the water bath.

An appreciation of other aims and objectives of the present invention and a more complete and comprehensive understanding of this invention may be achieved by studying the following description of preferred embodiment and alternative embodiments and by referring to the accompanying drawings.

BRIEF DESCRIPTION OF THE DRAWINGS

In FIG. 6, the patient is shown in a lateral view in an upright position and the examiner is checking tissue near the rib cage.

FIG. 21E is an illustration of an alternative embodiment of the invention that includes a heating pad that may be worn like an article of clothing. Another embodiment of the heating pad is pictured in FIG. 21F.

FIG. 32 shows the Finger Walk$^{SM}$ "S" Curve.

FIG. 55 shows the same breast after the emulsification that occurs during a hot bath and massage, while

FIGS. 57 through 64 are computer-generated representations of breasts under floatation.

FIG. 65 is a cross-sectional plot of a female breast, while FIG. 66 is a table that contains bust mold measurements for the breast shown in FIG. 65.

FIGS. 68A and 68B depict containers that are used to cast a mold of female breasts. The mold may be used to manufacture a bra, blouse, shirt or dress.

FIGS. 72 and 73 are front and side views of the Perfect Bra™ which is manufactured in accordance with the present invention.

FIGS. 74 and 75 offer views of the Perfect Bra™ and a conventional bra, respectively.

DETAILED DESCRIPTION OF PREFERRED & ALTERNATIVE EMBODIMENTS

The Basic Finger Walk$^{SM}$ Method

Figure 1:
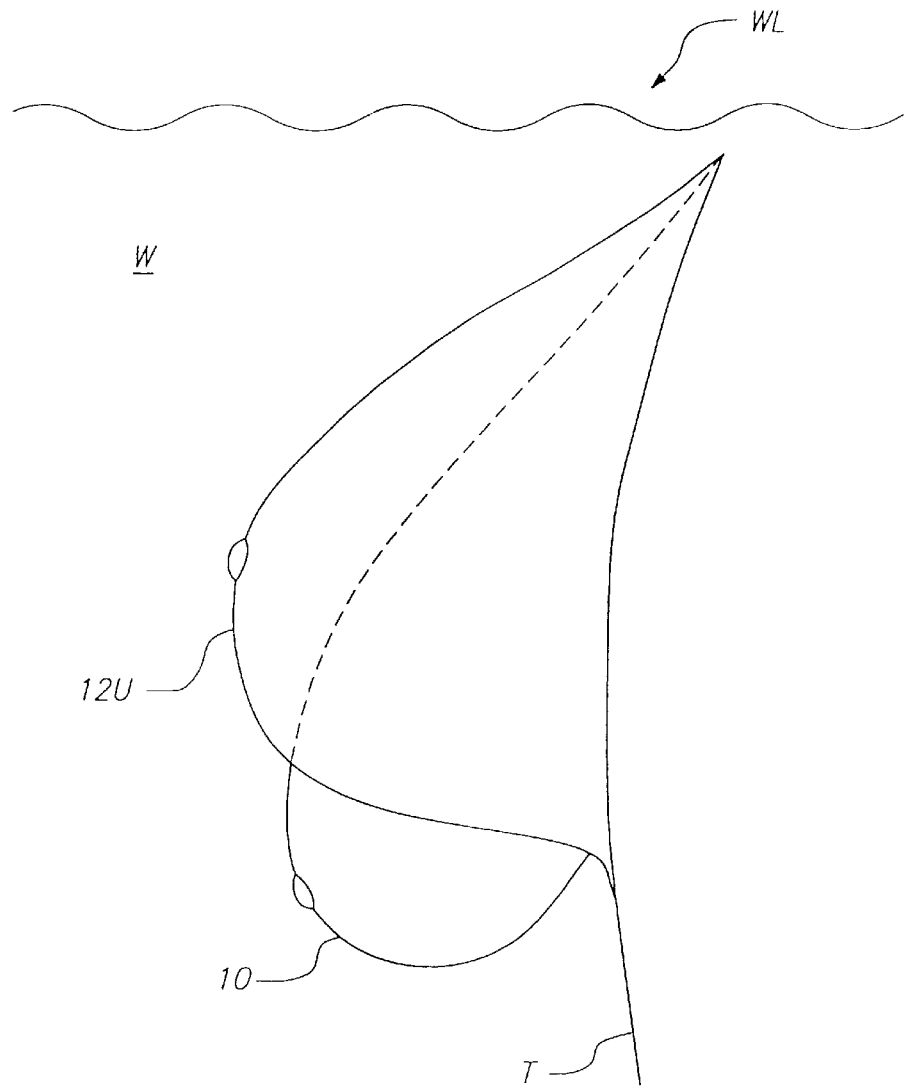
FIG. 1 is a cross-sectional view which compares a female breast in a pendent position and in the levitated position which occurs when it is immersed in water.

FIG. 1 furnishes cross-sectional, superimposed views of a single female breast. In this figure, the patient is positioned in an upright posture, leaning forward at an angle of approximately five to fifteen degrees. In one view, the breast is shown extending from the torso T in its normal, unsupported and pendent position 10. The second view shows the position of the same breast when the breast is immersed in water W. This immersion is accomplished by having the patient sit in a tub filled with hot water. This second position, indicated by the reference character 12U, is the natural or undeflected position of the breast under the influence of the levitating effects of the water W. When the breast is substantially submerged below the water line WL, the buoyancy of the breast tissue in the water counteracts the effects of gravity. Although other fluids such as salt-water may be employed to exaggerate the differences in density between the breast and the fluid medium, and to further lift the breast tissue, ordinary hot water is utilized in the preferred embodiment of the invention. According to the preferred embodiment of the invention, the best temperature range for the hot water is 101 to 104 degrees Fahrenheit.

This buoyancy or "floatation" effect enhances the ability of the patient herself or a second person to test the breast tissue to detect abnormalities. The levitating effects of the present invention allow the internal structure of the breast to float out of the way of the examiner's probing fingertips. By using the Finger Walk$^{SM}$ method of the preferred embodiment, aberrations in the breast may be discovered at an early stage.

Figure 2:
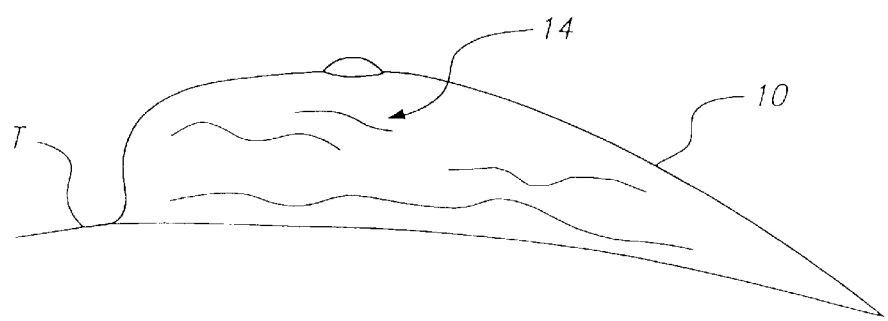
FIGS. 2 and 3 are cross-sectional illustrations of a female breast in a supine position in its undeflected non-floatation position.
Figure 3:
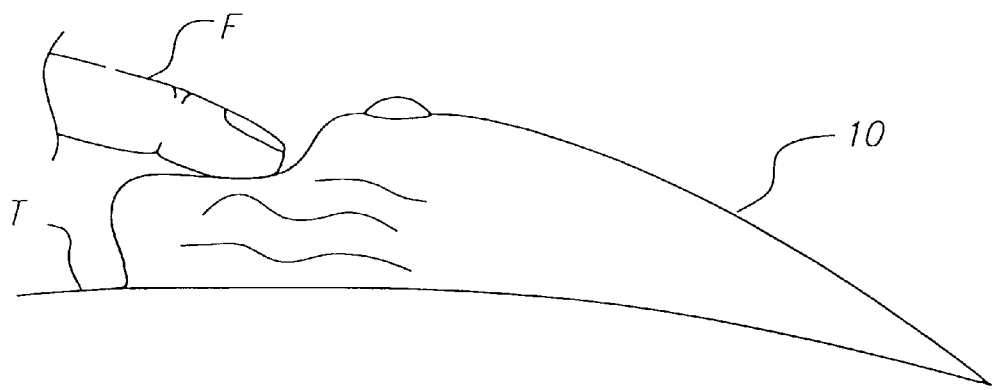

FIGS. 2 and 3 provide additional cross-sectional illustrations of a female breast which is not immersed in water. In FIG. 2, the patient is reclining on her back in a supine posture. As a consequence, the breast occupies a normal flattened position. The collapsed, overlapping internal structure of the breast is identified by reference character "14". FIG. 3 illustrates the finger F of an examiner who engages or palpates the breast as shown in FIG. 2 to detect abnormalities. This collapsed tissue 14, which may "pile up" in the absence of floatation forces, may cause health problems and may make it difficult for an examiner to detect an abnormality during a conventional examination. The levitation forces of the hot bath may assist the examiner by reducing the entanglement of internal tissues of the breast which, in turn, may increase the chances of detecting an abnormality. The hot bath may also emulsify fatty tissue within the breast, which would also enhance the examiner's ability to detect an abnormality.

In this Specification, the term "examiner" refers to both the patient herself or to a second person who may stroke the tissue in an attempt to detect abnormalities. Although the preferred embodiment of the invention pertains to the examination of the female breast, the present invention may be beneficially employed to examine a variety of body parts of both genders, including tissues of the male abdomen and testicles.

Figure 4:
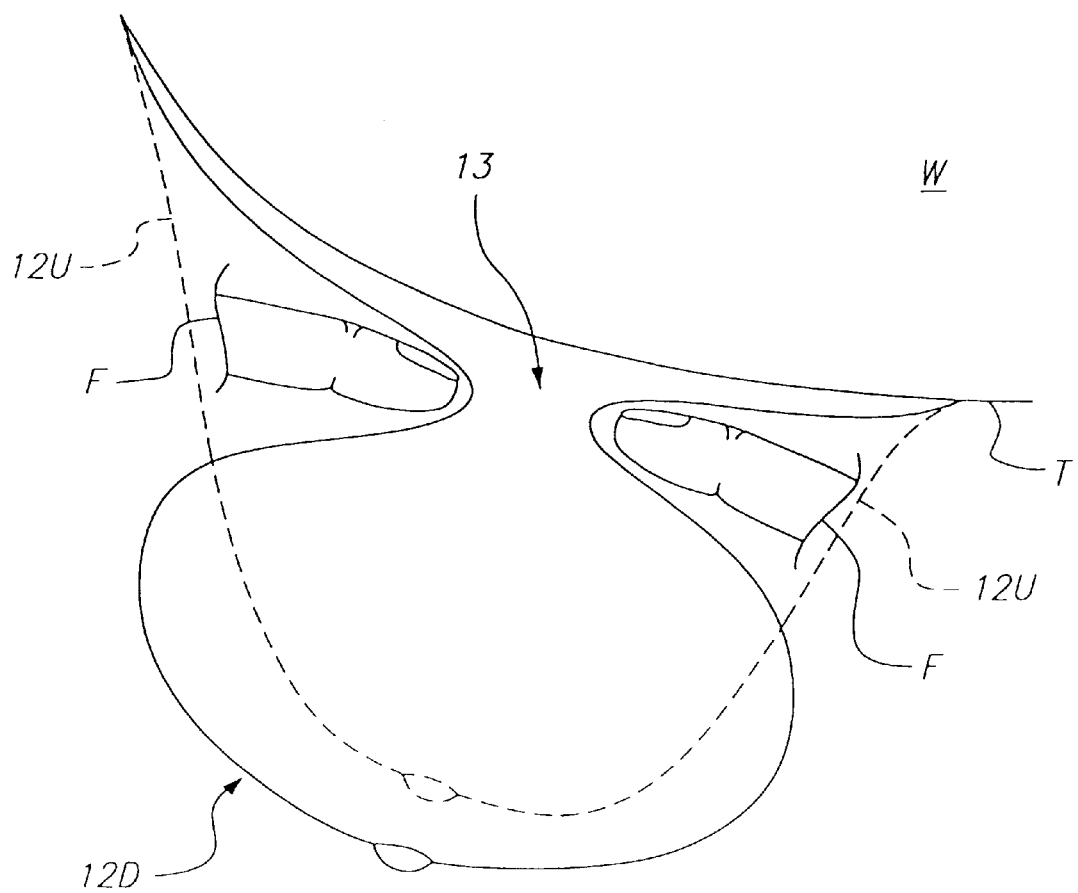
FIGS. 4 and 5 show cross-sectional depictions of a female breast in a top view in floatation in both an undeflected pendent position and in a deflected position that occurs during examination.
Figure 5:
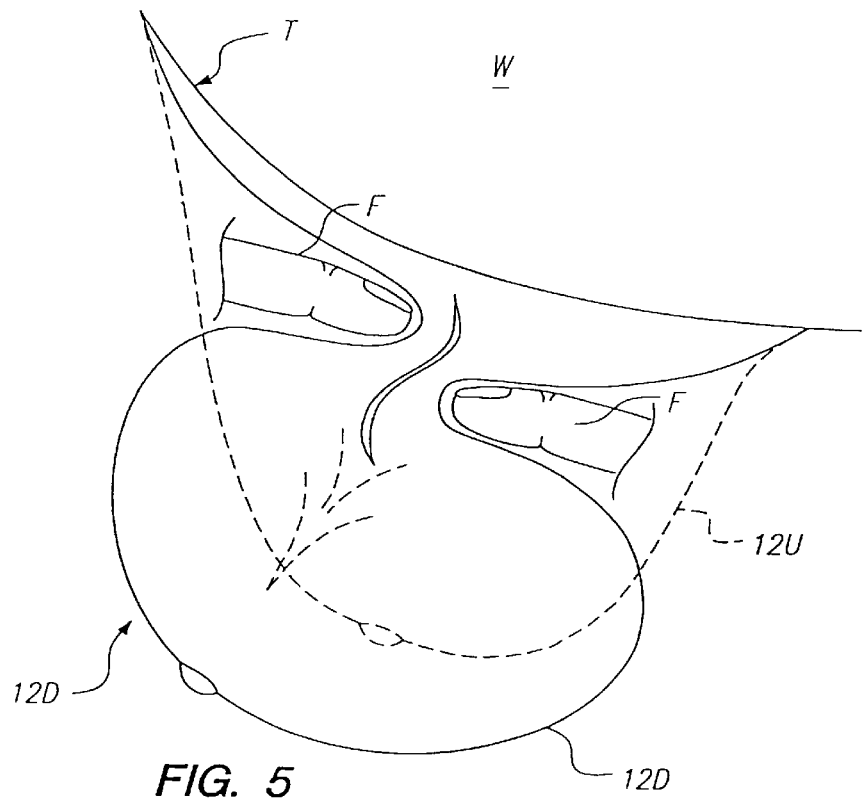
Figure 6:
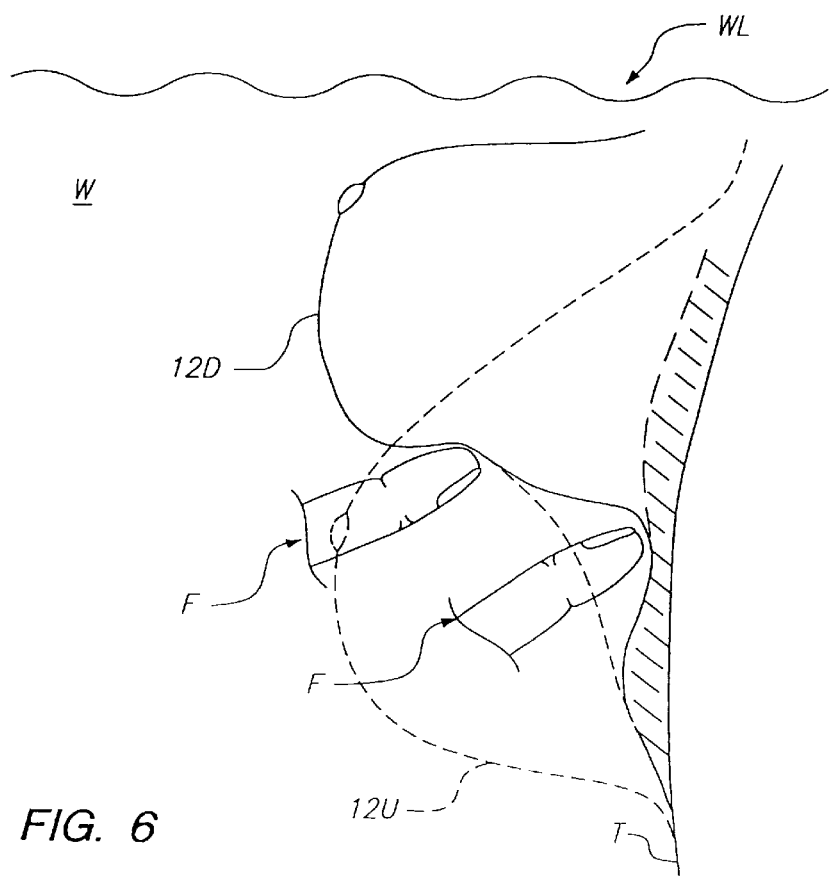
FIG. 6 provides a cross-sectional representation of a female breast in floatation in both undeflected and deflected positions.

FIGS. 4 and 5 provide two superimposed views of a single breast. The perspective in both cross-sectional views is from the overhead position, looking down into the water bath towards the immersed breast. In both FIGS. 4 and 5, the patient is in an upright position, leaning forward approximately five to fifteen degrees. One depiction, indicated by 12U, represents the breast in a natural undeflected position under the effects of floatation. The second depiction, indicated by 12D, illustrates the shape of the breast after it has been deflected by the gentle probing action of the examiner's finger tips FT. The constricted portion of the breast that lies between the examiner's finger tips FT is indicated by reference character 13. It is this ability to obtain the narrow constriction that greatly enhances the sensitivity of the detection procedure. Without forming the constricted portion of the tissue, the examiner's ability to detect an abnormality may be reduced. Forming this constricted three-dimensional projection is quite different from the generally flat or planar, circular rubbing motions advocated by more conventional methods of breast examination. The enhanced sensitivity offered by the Three Dimensional Perfect Way Finger Walk method is not available to patients who rely on conventional breast-exam and mammographic techniques.

In the preferred embodiment of the invention, slight pressure is applied to the breast tissue simultaneously using the tips of the fingers of both hands. The hands are placed in a position that allows the tips of the fingers of opposite hands to face each other. This arrangement of the fingers is referred to as the "opposing" position of the fingertips. When the tips of the fingers are used to probe the tissue in this opposing position, the capacity to detect abnormalities is enhanced. The heightened sensitivity results from the improved sensory ability of the finger tips to discover an abnormality when it is caught between the two opposed surfaces of the finger tips.

Unlike conventional examination methods, the floatation environment allows the breast to assume its fill, undistorted and natural position and shape. Conventional breast examination procedures often involve the use of the supine position and other positions which introduce muscle and tissue distortions caused by the placement of the patient's arms over her head. Other tissue distortions are caused by gravity. The present invention eliminates these unwanted effects by counteracting all forces which would tend to block the patient's ability to perform an e presents side views of a female breast under floatation forces. In this view, the patient is in an upright position, leaning forward slightly (approximately five to fifteen degrees). The outline marked "12U" represents the position of the levitated breast without any deflection forces introduced by the examiner. The outline marked "12D" represented the position of the levitated breast after it has been deflected by the examiner. The outline indicated by reference character 12D reveals how the breast can be gently floated out of the way exposing the structure near the rib cage.

Figure 7:
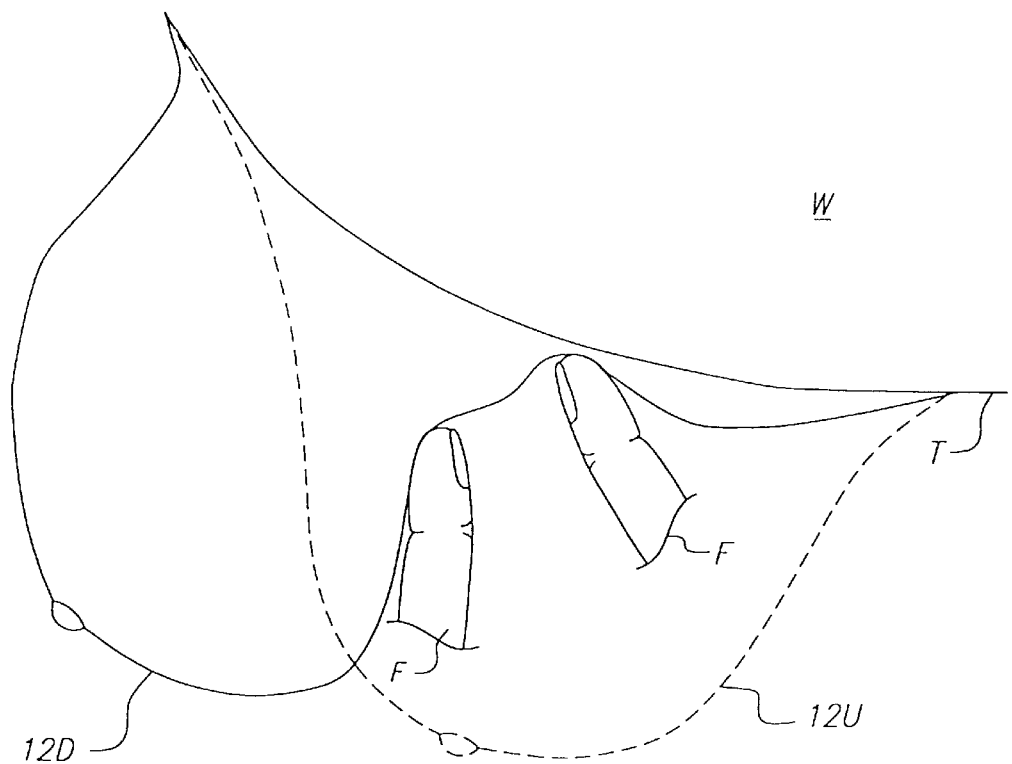
FIGS. 7, 8 and 9 exhibit cross-sectional diagrams of a female breast in floatation in overhead views. Both undeflected and deflected conditions are shown in each drawing.
Figure 8:
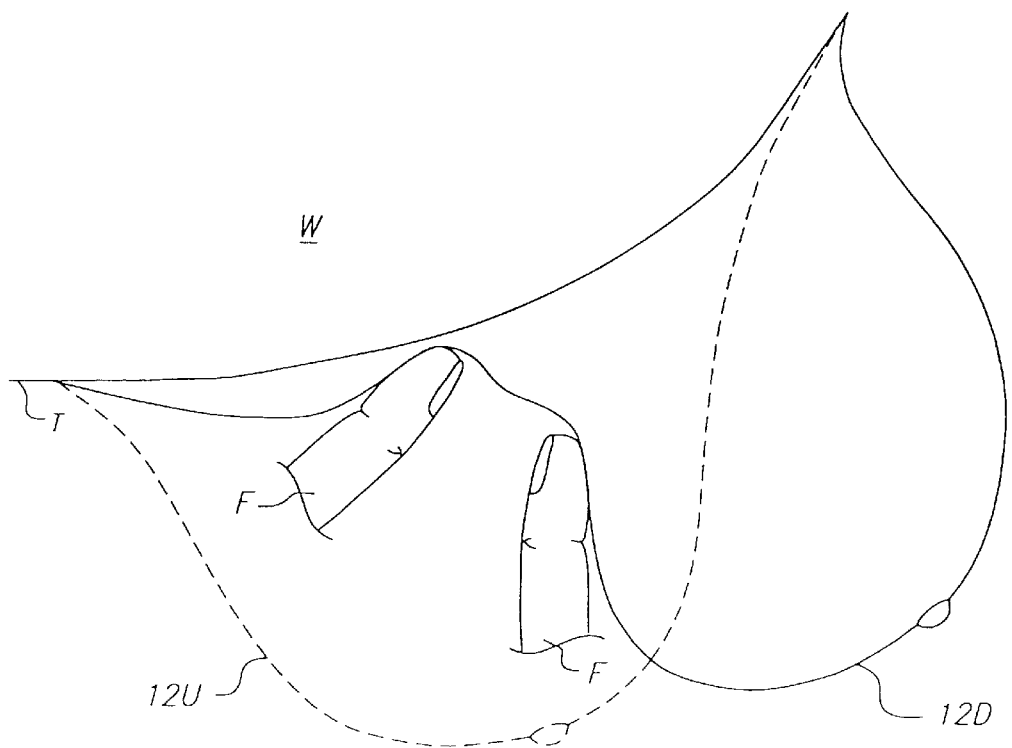
Figure 9:
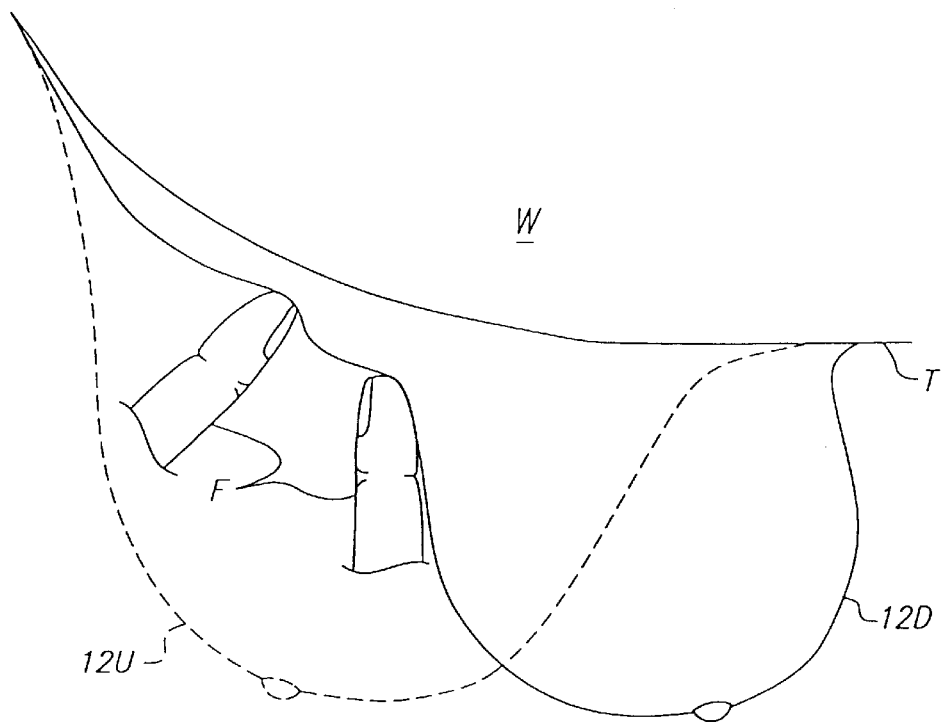

FIGS. 7, 8 and 9 furnish three additional overhead views of the patient during an examination. While the patient is sitting with her and leaning forward slightly, the examiner uses his or her fingers F to gently probe the breast tissue. In FIG. 7, the examiner probes the patient's right breast (shaded) in the area of the rib cage. FIG. 8 illustrates an examination of the patient's left breast (shaded). FIG. 9 supplies yet another view of an examination of the patient's right breast (shaded).

Figure 10:
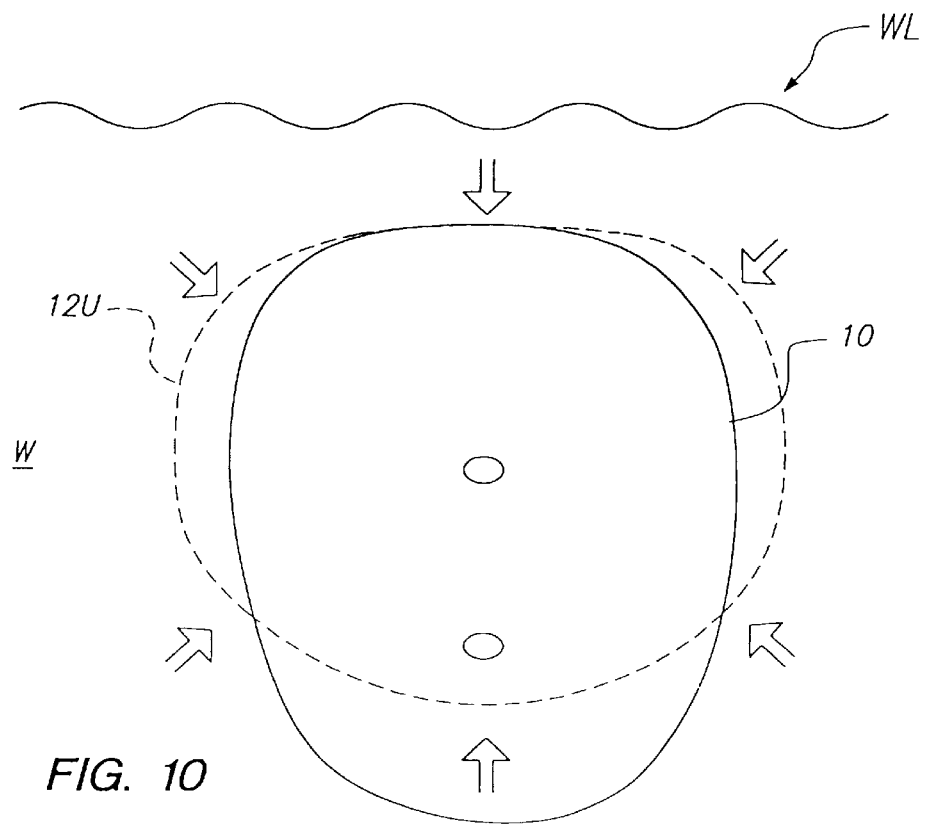
FIG. 10 supplies frontal view of a female breast both under the effects of floatation and under non-floatation conditions. This figure also exhibits the anticipated direction of the opposed fingers in the Finger Walk$^{SM}$ method of examination.

FIG. 10 supplies front view of a female breast, both under the effects of floatation and under non-floatation conditions. The arrows in FIG. 10 represent positions around the circumference of the breast where the examiner may place his or her fingers to begin the Finger Walk[SM] method. In one embodiment of the invention, the examiner places the fingers from each hand at opposite positions of the generalized "circle" formed by the periphery of the breast where it meets the torso. As a convenient reference, the unmarked arrows in FIG. 10 may be associated with the hour positions of the clock. "Opposite pairs of positions" means twelve and six o'clock, one and seven o'clock and four and ten o'clock et al. The examiner would first perform an examination starting at one of the opposite pairs, and then proceed around the circumference of the breast to perform a complete test for abnormalities as may be necessary.

The floatation influence of the water bath on the breast permits the examiner to gently move the breast tissue to one side so that tissue immediately adjacent to the breast may be tested for abnormalities. By moving the breast to one side, the examiner may also gain access to testing the tissues beneath the breast which are adjacent to the rib cage.

Figure 11:
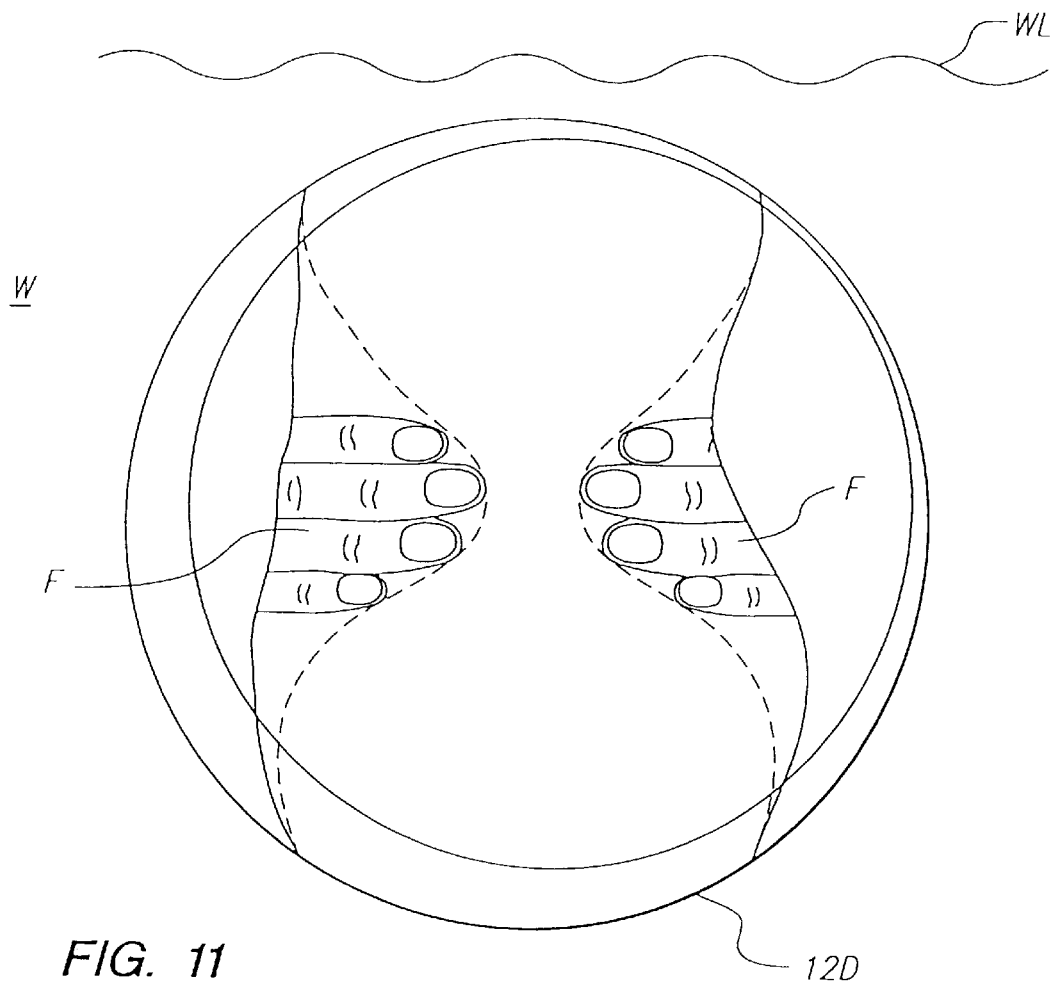
FIG. 11 depicts front views of the breast during an examination that shows the fingers from each hand in an opposed juxtaposition.
Figure 12:
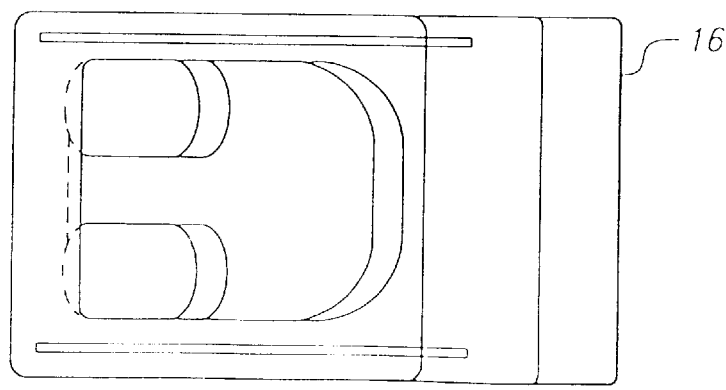
FIGS. 12, 13, 14, 15 and 16 offer top and cut-away side views of various floatation spa tubs 16 which may be used to practice the Finger Walk$^{SM}$ examination method.
Figure 13:
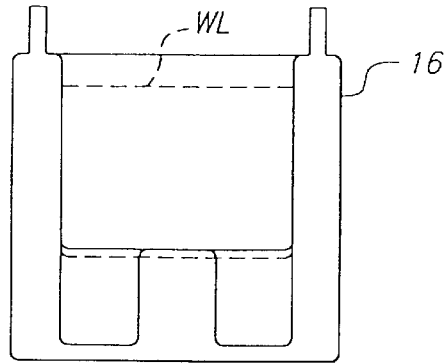
Figure 14:
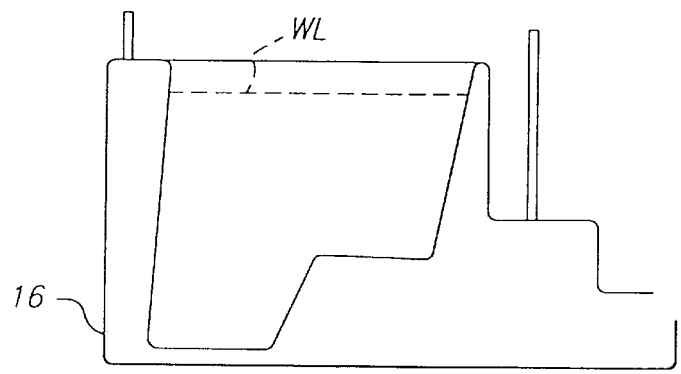
Figure 15:
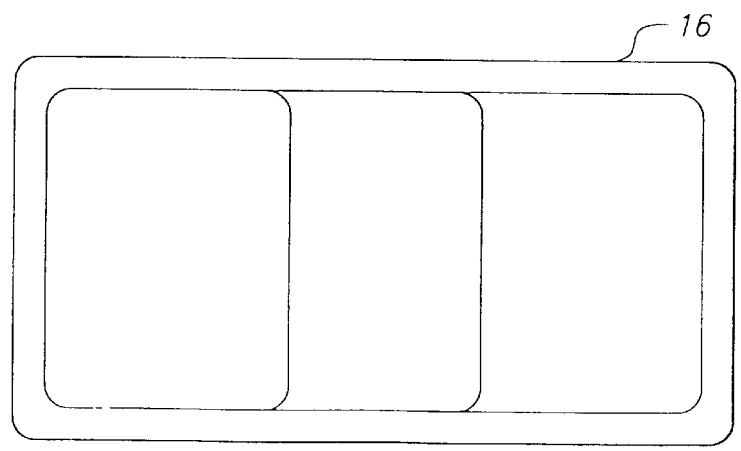
Figure 16:
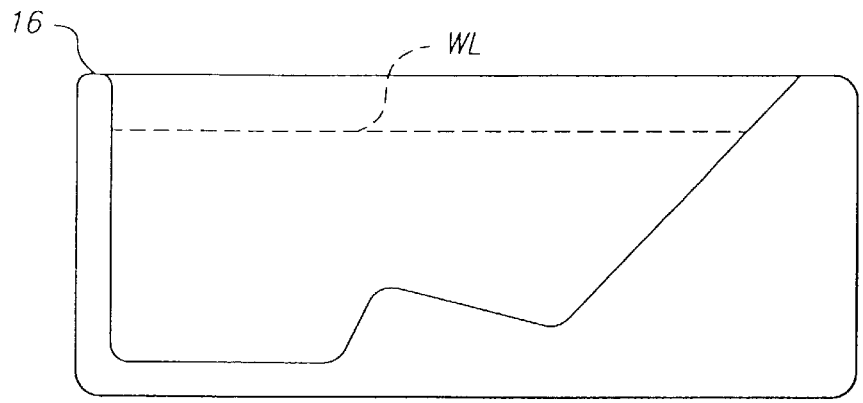

FIG. 11 depicts front views of the breast during an examination that utilizes several fingers from each hand. In general, the three index fingers are employed to perform an examination.

Advantages of the Finger Walk[SM] Method

The present invention is designed to stimulate the flow of lymph fluid in breast, as well as to encourage blood flow through the capillaries of the breast. The Finger Walk[SM] may break up lumpy clusters and make breast tissue more pliable. These effects may compensate for a patients's lack of adequate exercise.

Unlike conventional two-dimensional body massage techniques, the Finger Walk[SM] Method may help clear up lumpiness and generally make the breast more pliable. The stimulation of the flow of the lymphatic system may inhibit maladies in the body tissue adjacent to the lymph ducts. The lymphatic duct system does not have a circulating pump to drive the lymph fluid through the duct system to the lymph nodes. The lymph system depends upon the motion of the body in the form of work or exercise to cause the muscles to impose forces upon the lymphatic duct system. These forces, in turn, drive the lymph fluid to flow through the body to provide a cleansing function. Insufficient exercise may limit the flow of this fluid and provide inadequate cleansing.

It is reasonably well known that women athletes have a considerably lower incidence of breast cancer than the general population. This would imply that their athletic motions stimulate the flow of not only blood through the breast, but also the flow of the lymphatic fluids through the same area. This activity may promote better health in this area of the body and could potentially lower the incidence of cancer.

In addition to stimulating the flow of body fluids in the breast tissue, the Finger Walk[SM] Method may also have the beneficial effect of realigning the internal structure of the breast into its natural desired position. This realignment could be similar to an intestinal disorder caused by an intestine that has become displaced or contorted. The realignment of the tissues of the breast may improve the health of the breast and reduce the incidence of lumps and other breast abnormalities.

Apparatus Used to Practice the Finger Walk[SM] Method

Figure 17:
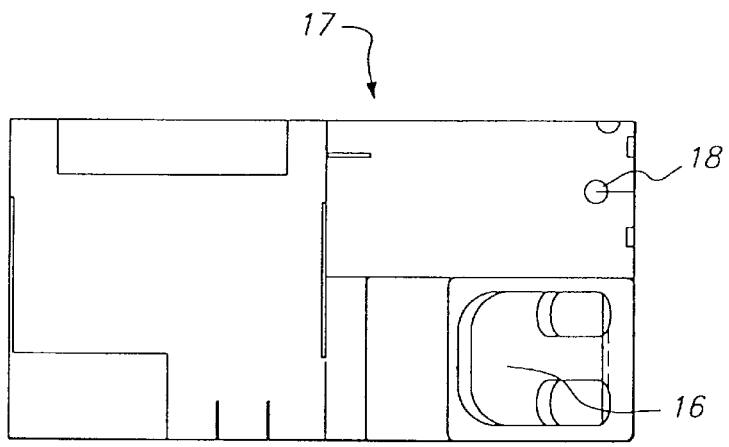
FIGS. 17, 18 and 19 furnish plan and elevational views of various embodiments of a modular spa facility 17 that includes both a tub 16 and a shower 18 which may be used to practice the present invention.
Figure 18:
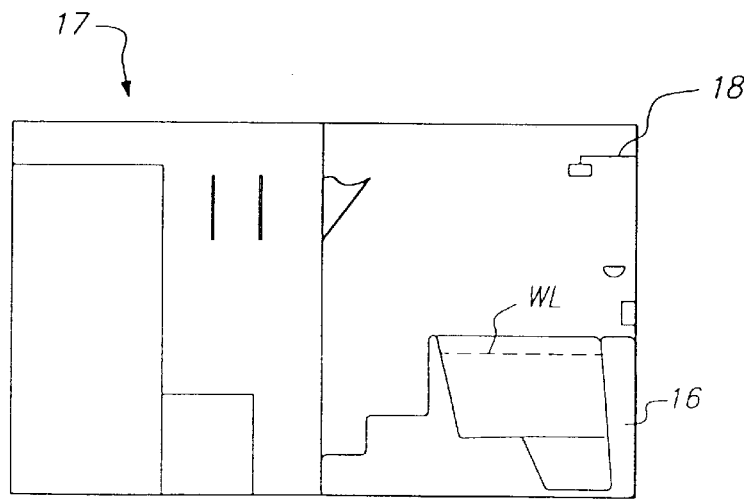
Figure 19:
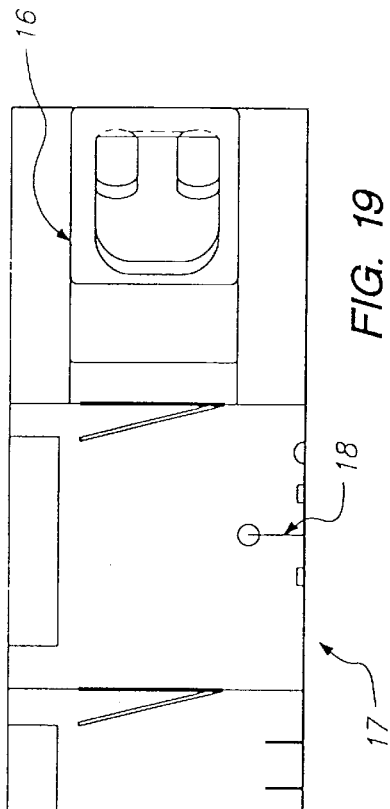

FIGS. 12, 13, 14, 15 and 16 offer top and cut-away side views of a floatation spa tub 16 which may be used to practice the Finger Walk[SM] examination method. FIGS. 17, 18 and 19 furnish plan and elevational views of various embodiments of a modular spa facility that includes a tub 16 and a shower 18 which may be used to practice the present invention.

Ultrasonic Imaging

Figure 20:
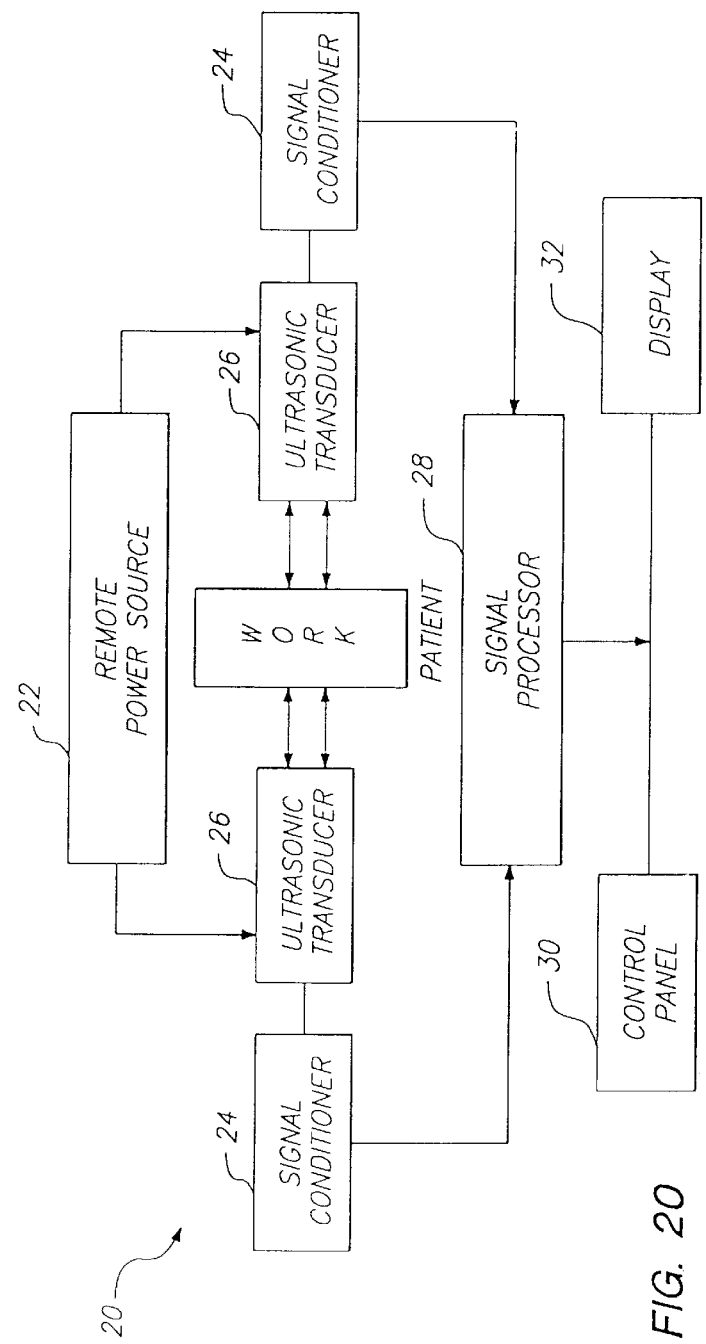
FIG. 20 is a schematic block diagram that depicts the ultrasonic apparatus that may be used to implement the invention.

FIG. 20 is a schematic block diagram that depicts apparatus that is well known to persons ordinarily skilled in the ultrasonic imaging art that may be used to implement the invention. Diagram 20 includes a remote power source 22 coupled to ultrasonic transducers 26. A signal is produced by the transducers 26 which is processed by signal conditioners 24 and signal processors 28 to form an image of the patient's body tissues. The image is generated on a display 32. The electronic equipment is operated by switches on a control panel 30.

Figure 21A:
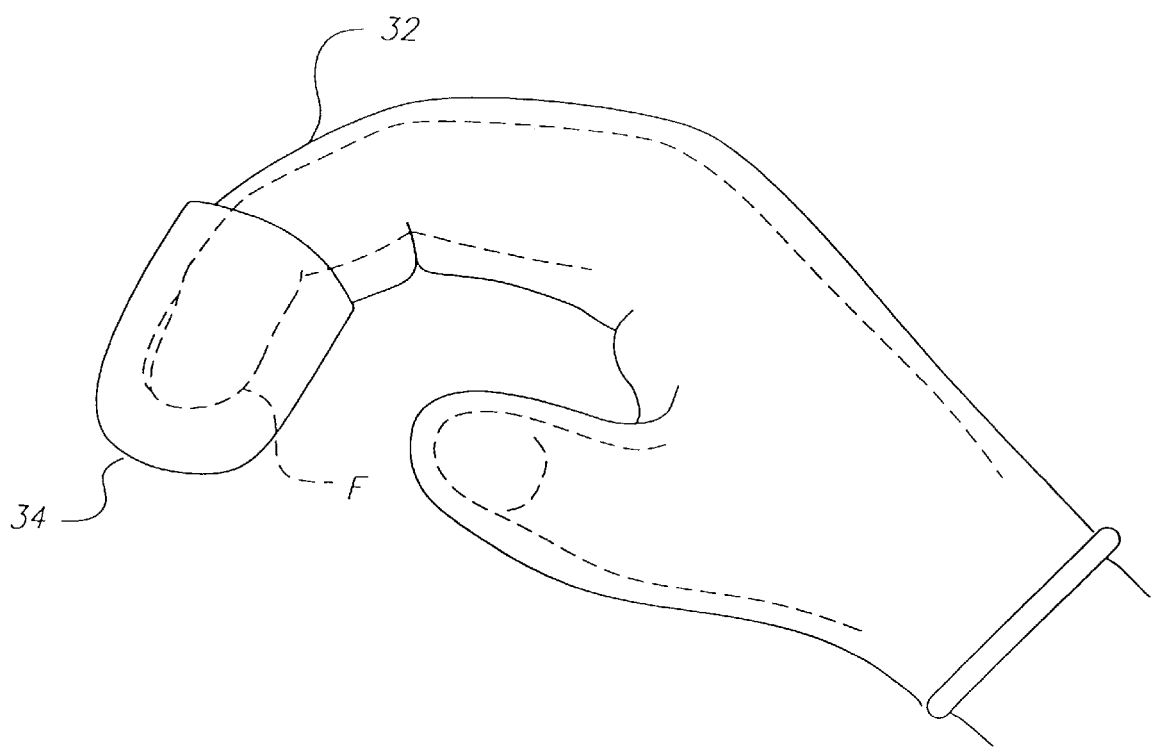
FIG. 21A is a schematic view of an ultrasonic transducer mounted in the finger of a glove that may be used to implement the invention.

FIG. 21A is a schematic view of an ultrasonic transducer mounted in the finger cup 34 of a glove 32 that may be used to implement the invention.

Figure 21B:
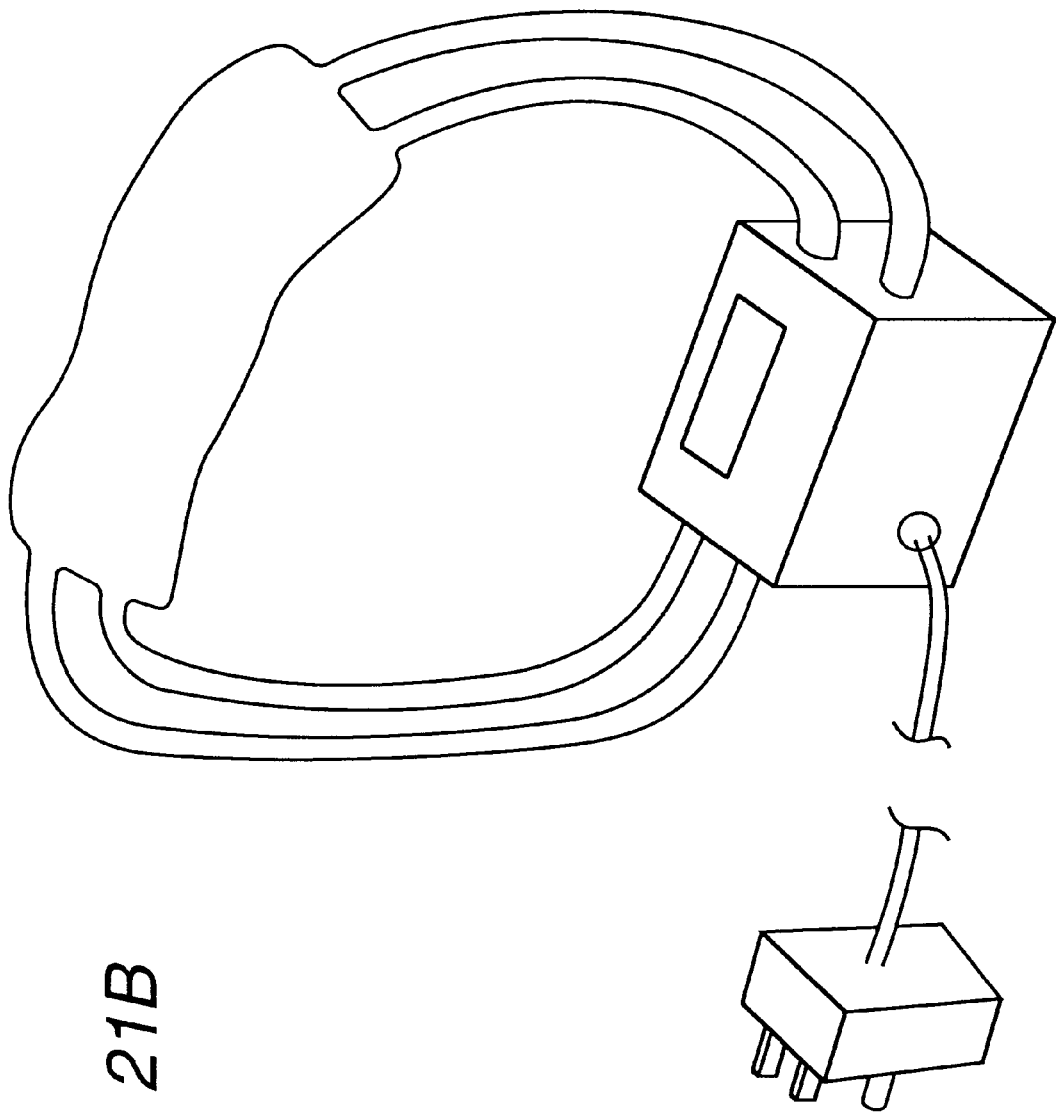
FIG. 21B provides an illustration of a heating pad that may be used to warm up the breast prior to ultrasonic imaging or an examination.
Figure 21C:
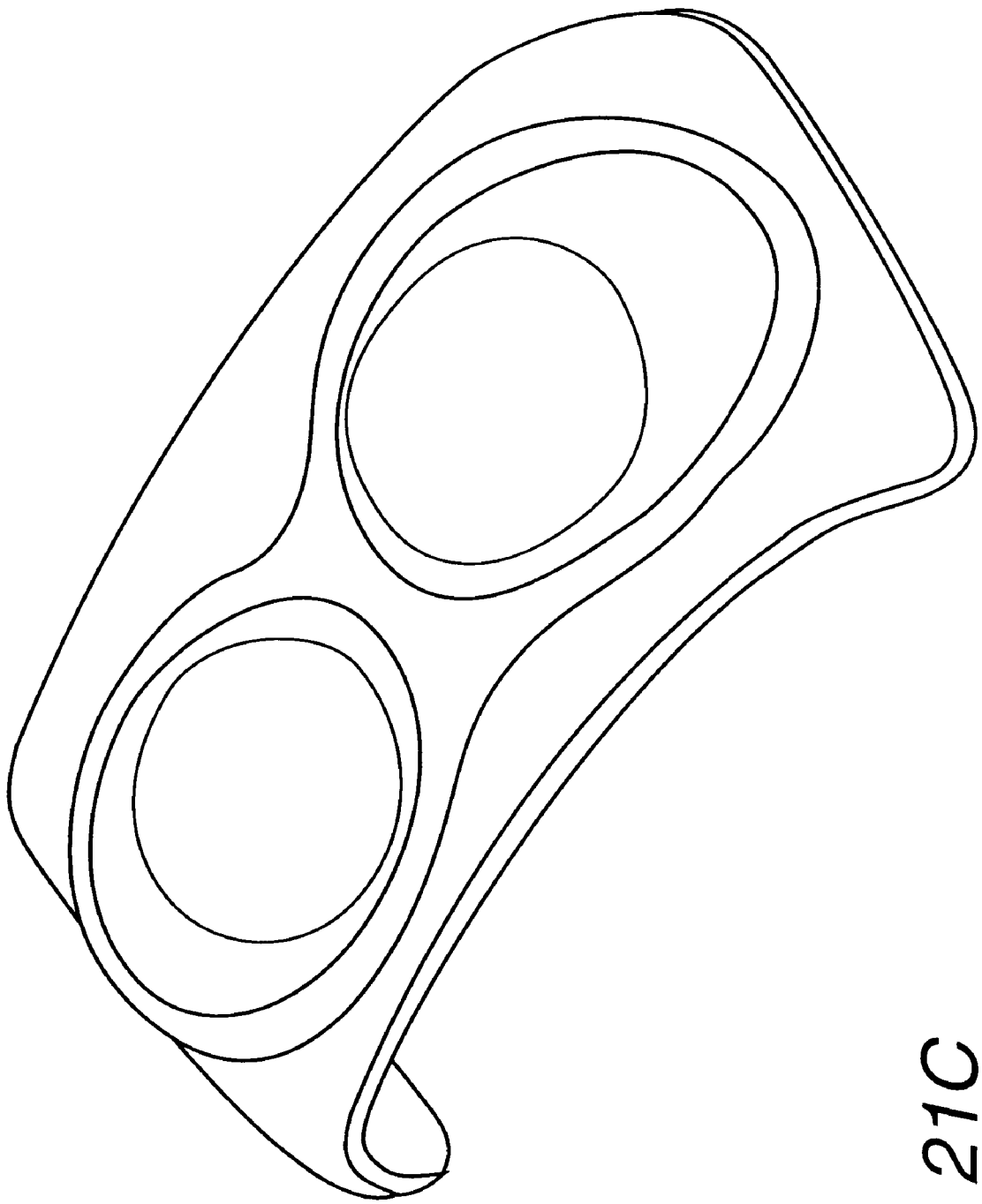
FIG. 21C furnishes a view of an alternative embodiment of the invention which incorporates a heating blanket.
Figure 21D:
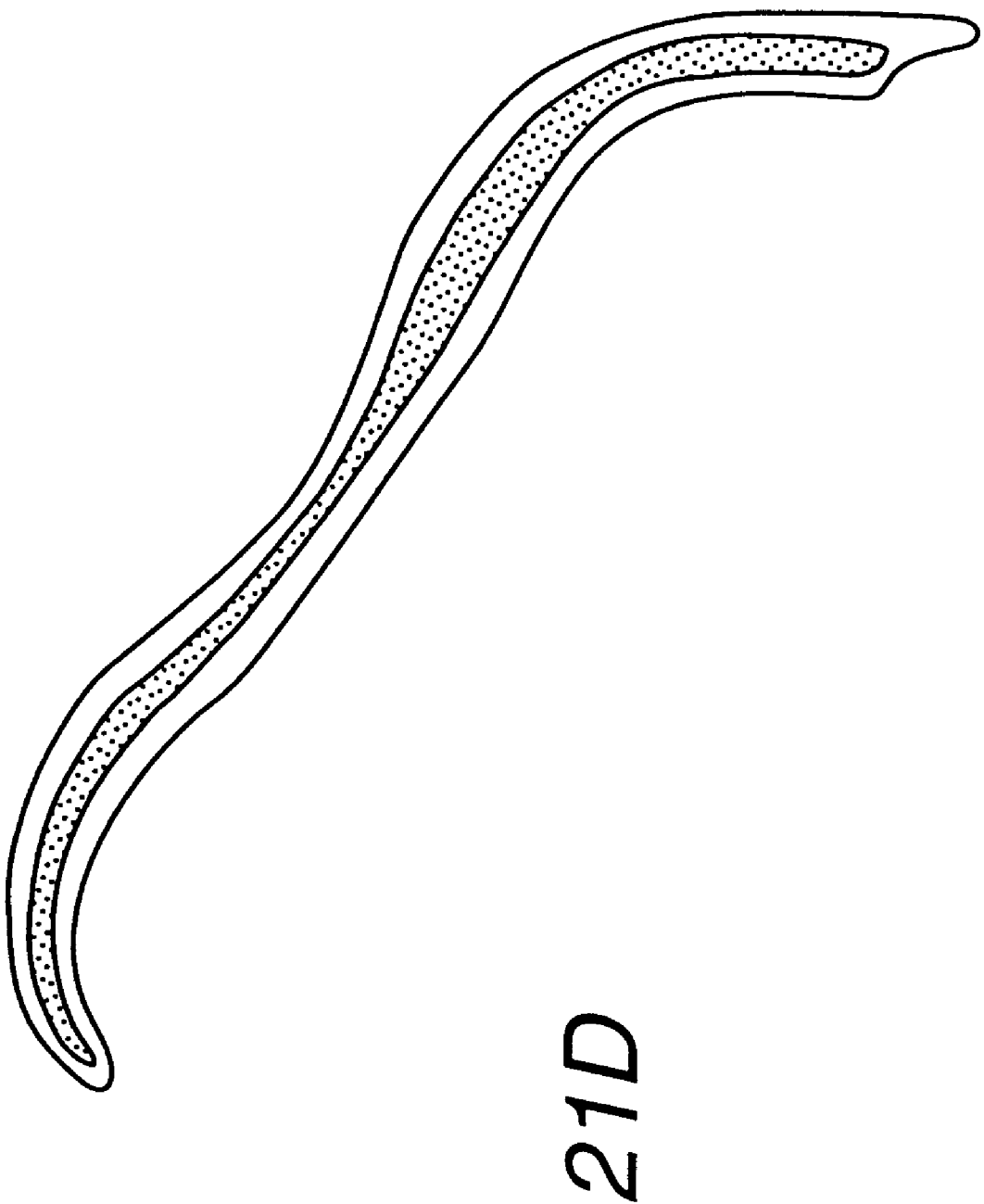
FIG. 21D offers a cross-sectional view of the heating blanket shown in FIG. 21C.

FIGS. 21B, 21C and 21D provide views of heating pads and blankets that may be used to warm the breasts prior to immersion in a floatation bath. FIG. 21B exhibits a heater and control unit 35A which contains a heating element and a thermostat, and heated water tubes 35B which conduct water to a impermeable heating pad 35C. Return tubes 35D carry water back to the heater 35A. A transformer 35E supplies stepped-down power to the heating element in the heater and control unit 35A. FIG. 21C portrays a preferred embodiment of a pad or blanket 35C, which includes a well area 35F formed to the contour of the breasts. FIG. 21D is a cross-sectional view of the pad shown in FIG. 21C taken along Section line A—A. The pad may be filled with a gel 35G to provide a comfortable transfer of heat to the patient.

FIG. 21E is an illustration of a garment intended for use with mammographic equipment. This alternative embodiment of the invention includes heating pads 35H having coils which are incorporated in a garment and which are formed to fit the breasts. The pads 35H are coupled to a control unit 35I and a portable and lightweight power supply 35J. The garment may be a vest or a light coat with a central zipper 35K, and is designed to heat the breasts and emulsify fatty tissues prior to beginning the mammogram procedure. Yet another embodiment of the heating pad is revealed in FIG. 21F, which utilizes pre-heated gel pouches 35L that may be slipped into breast pockets sewn into a garment.

Figure 22:
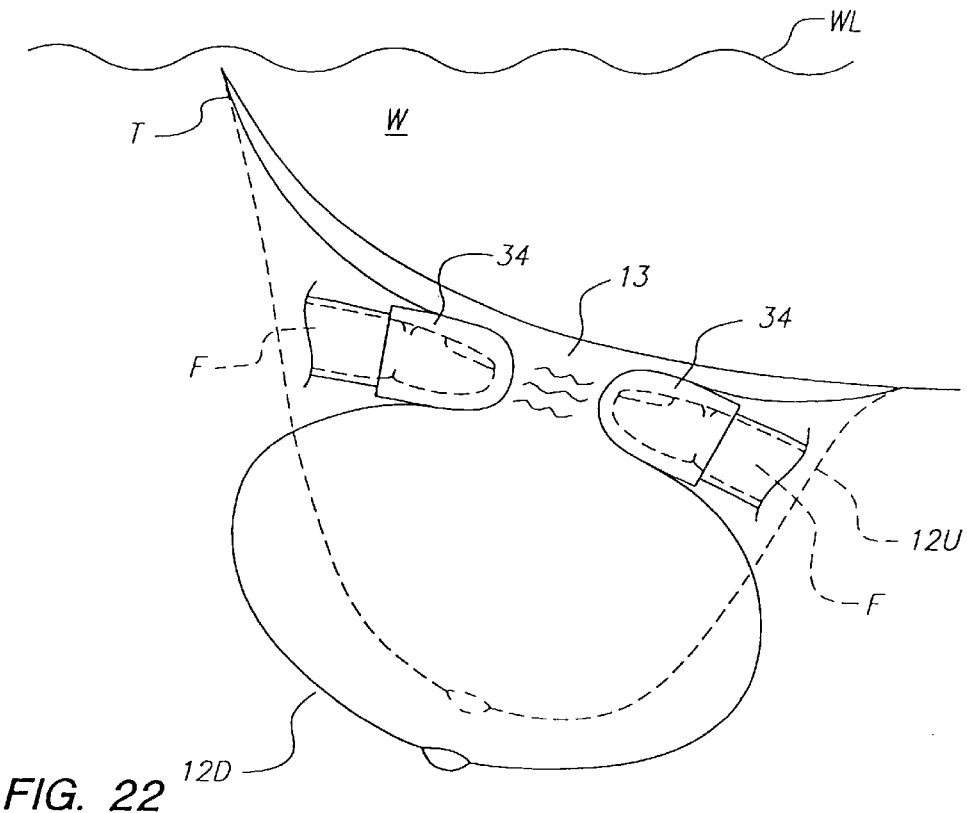
FIGS. 22 and 23 are superimposed views of a breast in both undeflected and deflected conditions. The view in each figure which represents the breast in floatation shows the tissue in a deflected condition during an examination that utilizes the transducer shown in FIG. 21.
Figure 23:
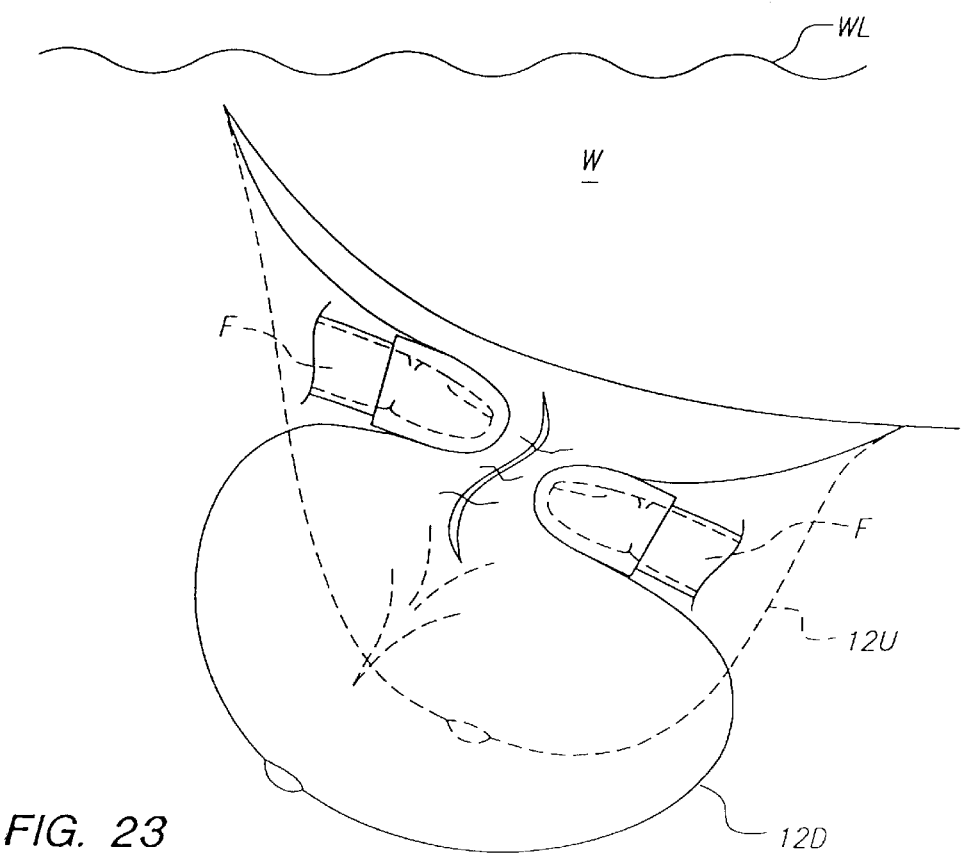

FIGS. 22 and 23 are superimposed views of a breast in both undeflected 12U and deflected 12D conditions. The view in each figure which represents the breast in floatation shows the tissue in a deflected condition during an examination that utilizes the finger cup transducer 34 shown in FIG. 21.

Advanced Finger Walk$^{SM}$ Methods

Figure 24:
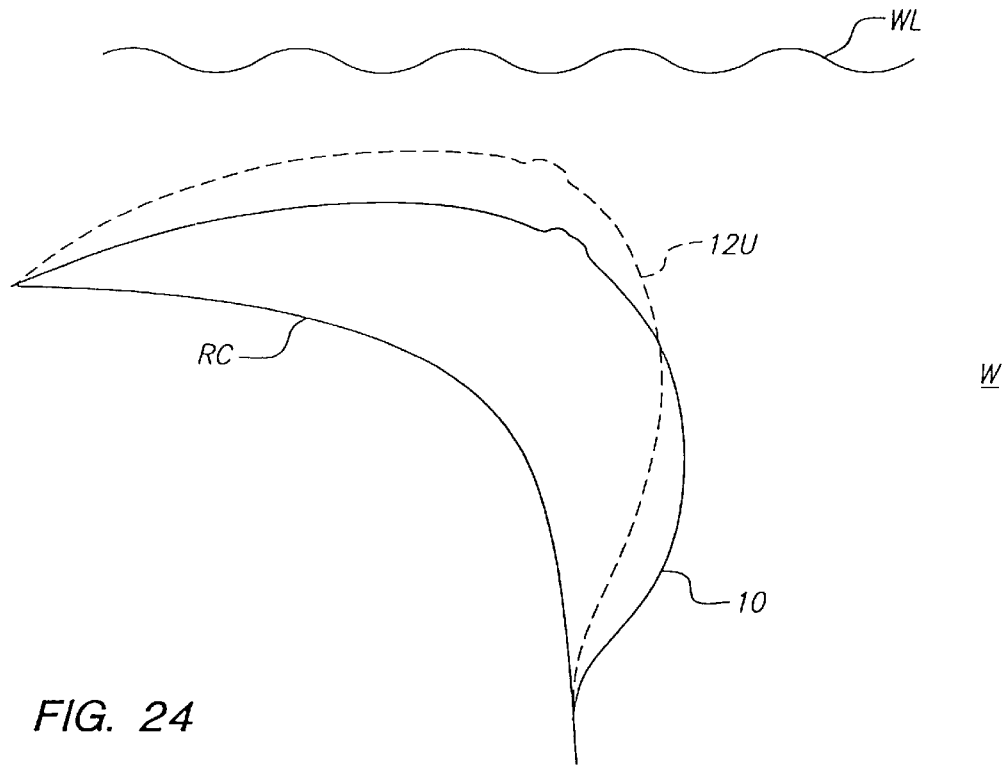
FIG. 24 provides views of a female breast while the patient is in a supine position.
Figure 25:
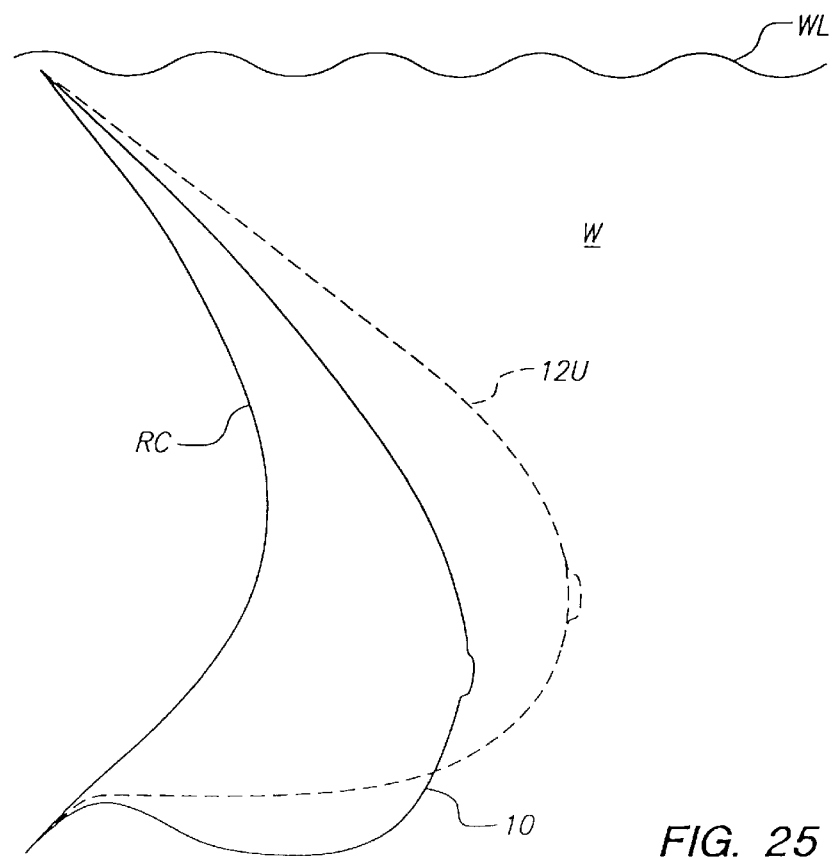
FIG. 25 provides views of a female breast with the patient in a supine position, but with the rib cage rotated outward approximately forty-five degrees.

FIG. 24 presents two different views of a female breast while the patient is in a supine position, with the patient flat on her back. As best seen in FIG. 24, without being immersed in water W, the breast would normally occupy the position indicated by reference character 10. When the breast is immersed below the water line WL, it is levitated and occupies the position indicated by reference character 12U. In either case, the contour of the rib cage is represented by reference character RC. FIG. 25 furnishes a pair of views of a female breast in both the normal 10 and levitated 12U positions when the patient is in a supine position, but with the rib cage rotated outward approximately forty-five degrees. This position is especially useful for examining the pectoral area under the arm pits after a breast is gently moved to one side with one hand while probing is accomplished with the other hand.

Figure 26:
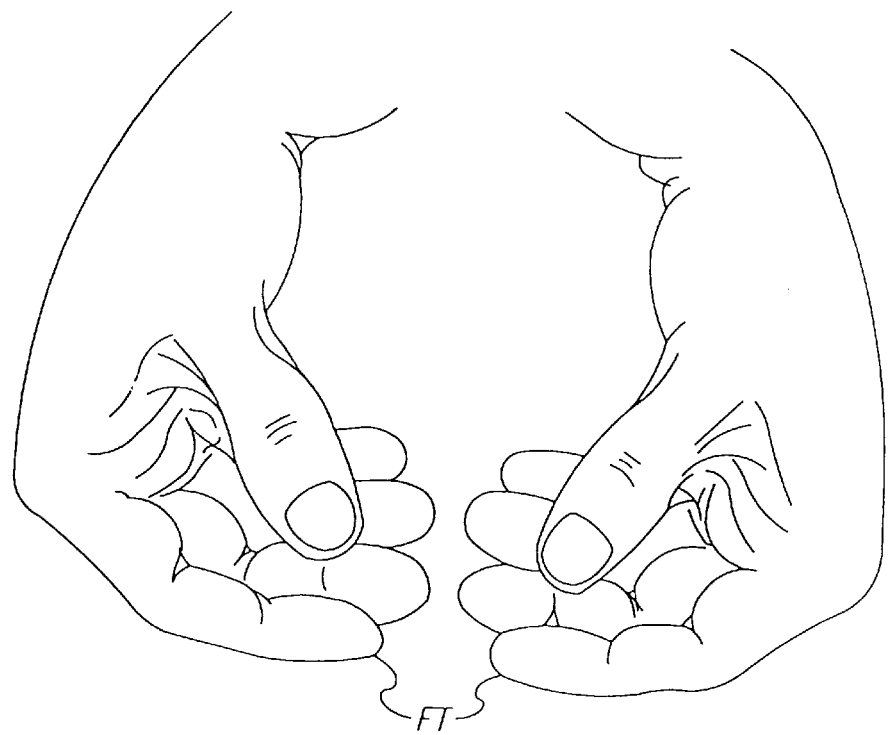
FIGS. 26, 27 and 28 illustrate the positions of the examiner's hands and fingers during the examination procedure embodied by the present invention.
Figure 27:
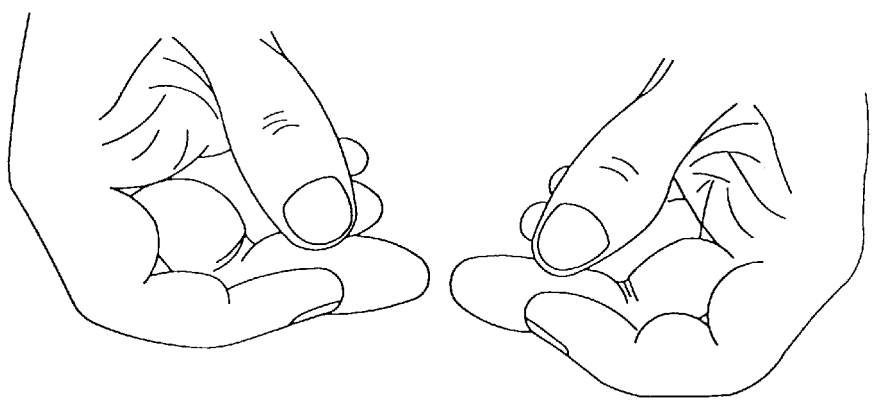
Figure 28:
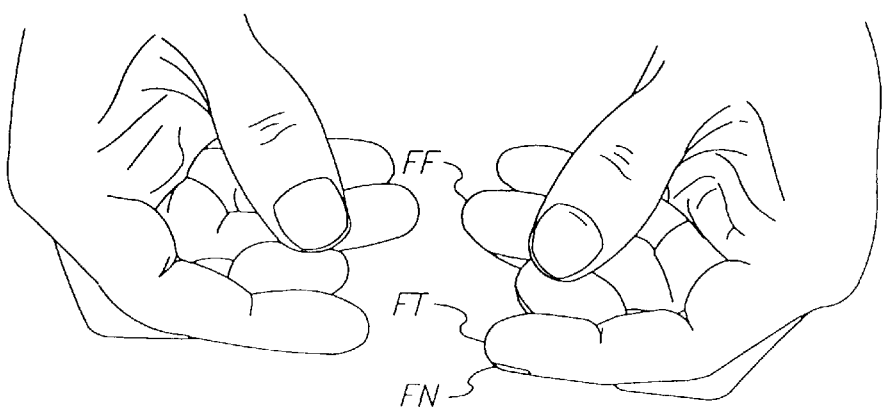

FIGS. 26, 27 and 28 reveal the placement and motion of the hands and the fingers according to a preferred embodiment of the present invention. In FIG. 26, the fingers F are generally in-line and occupy a normal extended position. In FIG. 27, the middle fingers F of both hands are extended toward each other. In FIG. 28, the middle fingers F move in and out slightly in a gentle repetitive motion, permitting the internal breast structure to readjust to penetration by the fingers. This readjustment enhances the ability of the examiner to detect abnormalities. FIG. 28 also identifies the area of the examiner's finger F that is used to perform the Finger Walk$^{SM}$ Method. The present invention relies on the enhanced sensitivity of the small portion of the finger tip FT that lies immediately below the fingernail FN. The flat portion FF of the finger, which is located near the whorl of the fingerprint, is less sensitive than the finger tip FT, and is therefore not used to perform the Finger Walk$^{SM}$. Unlike previous breast examination techniques that employ the rotating action of the flat portion of the fingers, the present invention utilizes a series of palpating motions.

Figure 29:
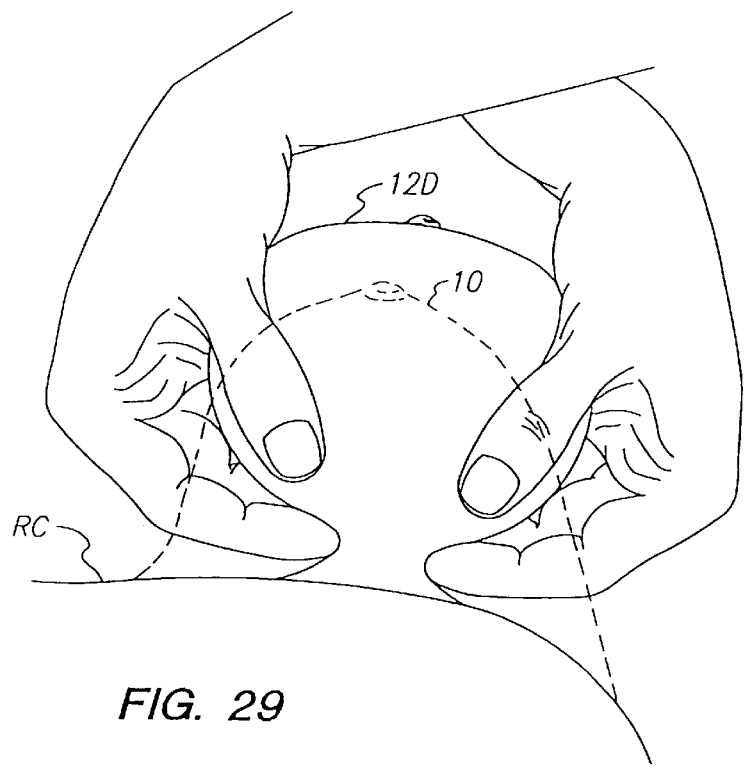
FIGS. 29, 30, 31, 32 and 33 comprise a series of overhead views of hand and finger positions that illustrate the Finger Walk$^{SM}$ method. In these figures, the right breast is immersed in a floatation bath with the patient in a generally upright position.

FIGS. 29 through 33 supply a sequence of illustrations of a Finger Walk$^{SM}$ procedure that is conducted while the patient is in an upright position, and leaning slightly forward. The perspective of FIGS. 29 through 33 is from a point above the patient's head, looking down into the water bath at her immersed breasts. FIG. 29 reveals a female breast on the right side of the torso in normal 10 and levitated and deflected positions 12D. A portion of the rib cage RC is shown along the base of the breast. FIG. 29 is an overhead view, depicting the crossed left and right hands of the examiner as he or she uses the fingers of both hands to constrict the lower portion of the breast. In FIG. 29, the fingertips are move progressively from the rib cage out toward the nipple. The examiner palpates the tissue by stroking the breast using very gentle pressure. This procedure may be repeated several times. Initially, this three-dimensional palpation may be utilized once or twice. Eventually, the breast structure may become more pliable and these steps can be repeated more often.

Figure 30:
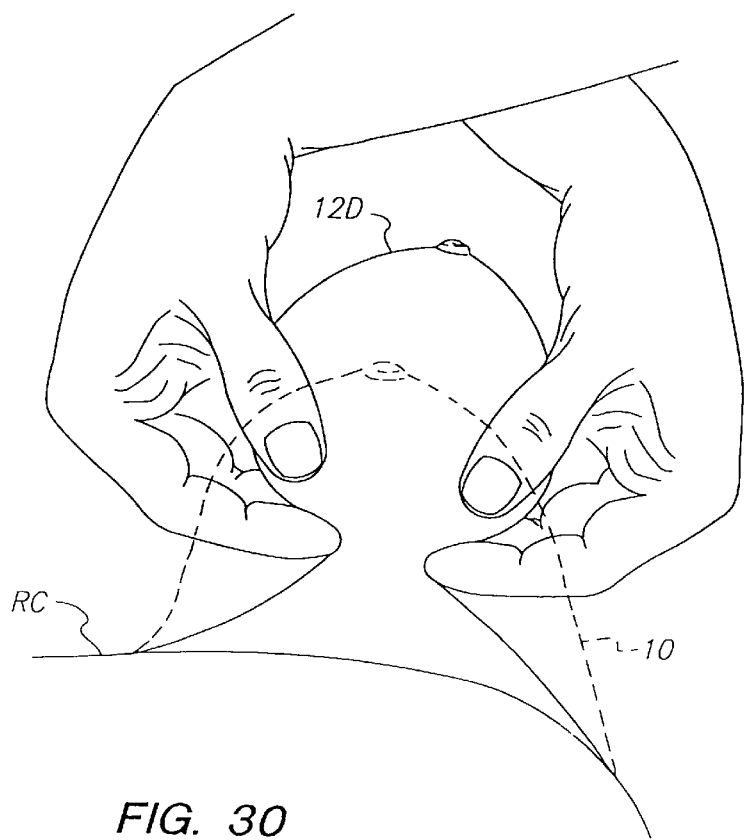
Figure 31:
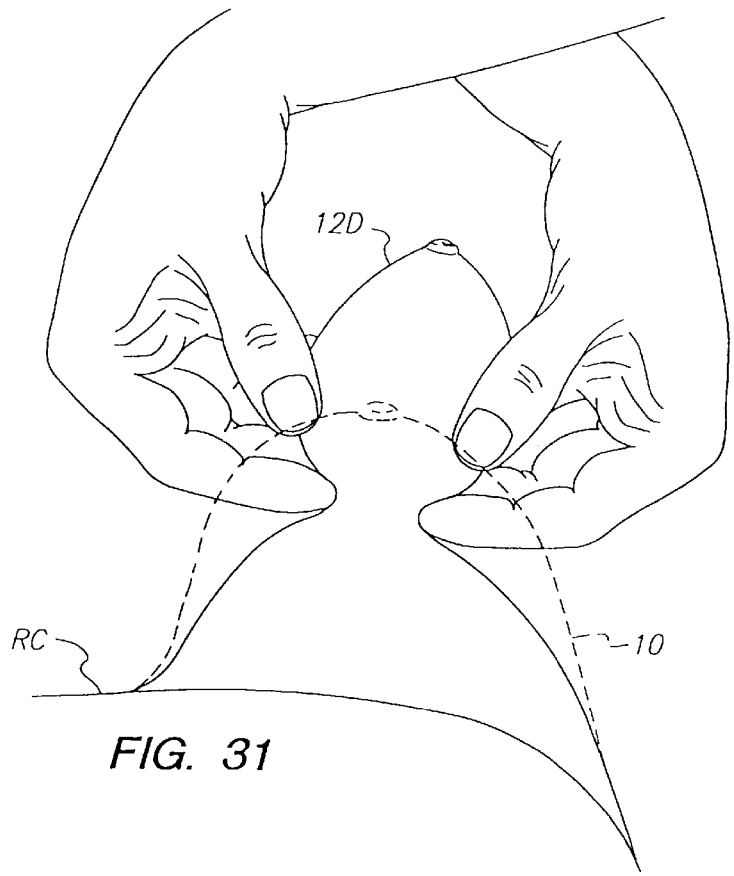

FIG. 30 shows the next stage of the Finger Walk$^{SM}$, depicting the breast in an extended position 12D. FIG. 31 offers a view of the breast in a constricted position 12D. In FIG. 30, the opposing finger tips are shown as they approach the midway position of the breast. The internal structure has undergone a reasonable change, which allows for greater three-dimensional penetration. As a result, the pressure applied by the fingertips at this stage may be generally reduced. In FIG. 31, the palpating fingertips have nearly reached the fill extent of travel toward the nipple and away from the rib cage.

Figure 32:
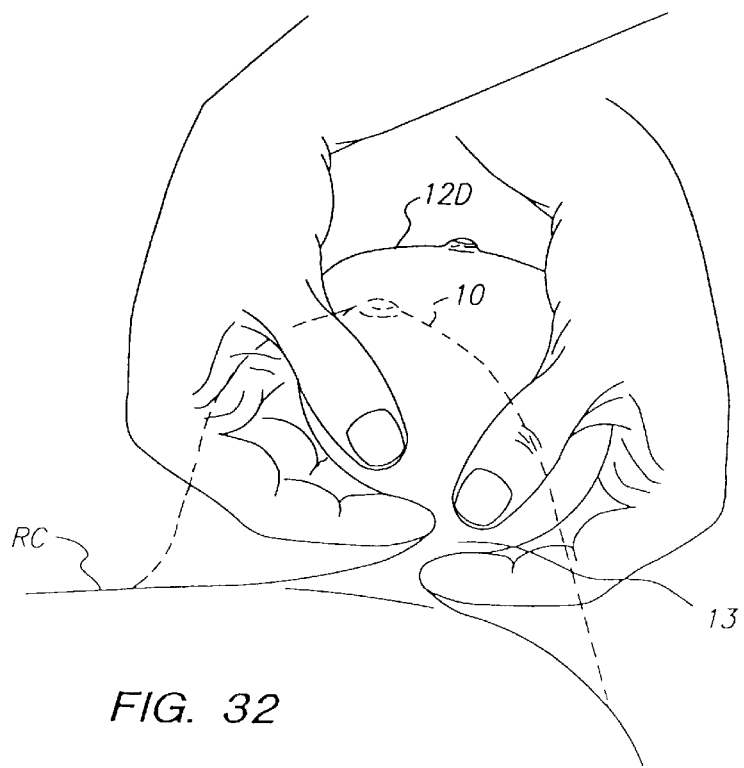
Figure 33:
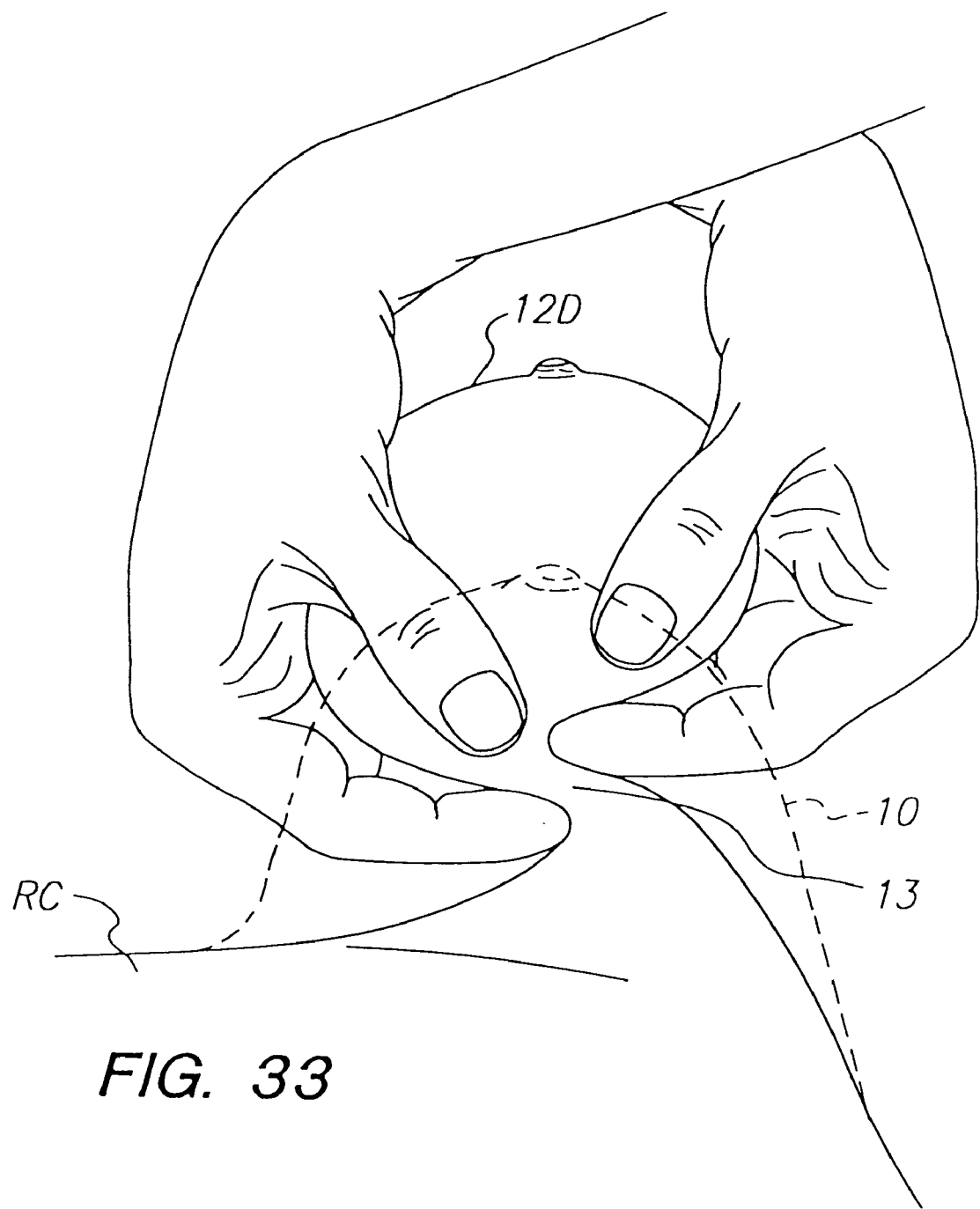

FIGS. 32 and 33 furnish two additional views of the examination process in which the examiner's fingers shape the patient's breast to form an constricted portion or "S-curve" 13 which enhances the sensitivity of the examiner to detect abnormalities. The examiner uses his or her hands so that the S-curve alternates from left to right and back and forth as may be required to perform a thorough examination. This portion of the method of the invention may be effectively employed in persons having larger breast sizes, for example, large C and D cups. The "S" curve and its modifications may be utilized to assist in reformatting the breast internal structure into its desired normal position. Another view of the "S" Curve is portrayed in FIG. 33 at a position midway in the breast. This procedure is similar to the Finger Walk maneuvers used in determining abnormalities. In FIG. 33, the fingertips are used to stroke the tissue rather than to probe the breast.

Figure 34:
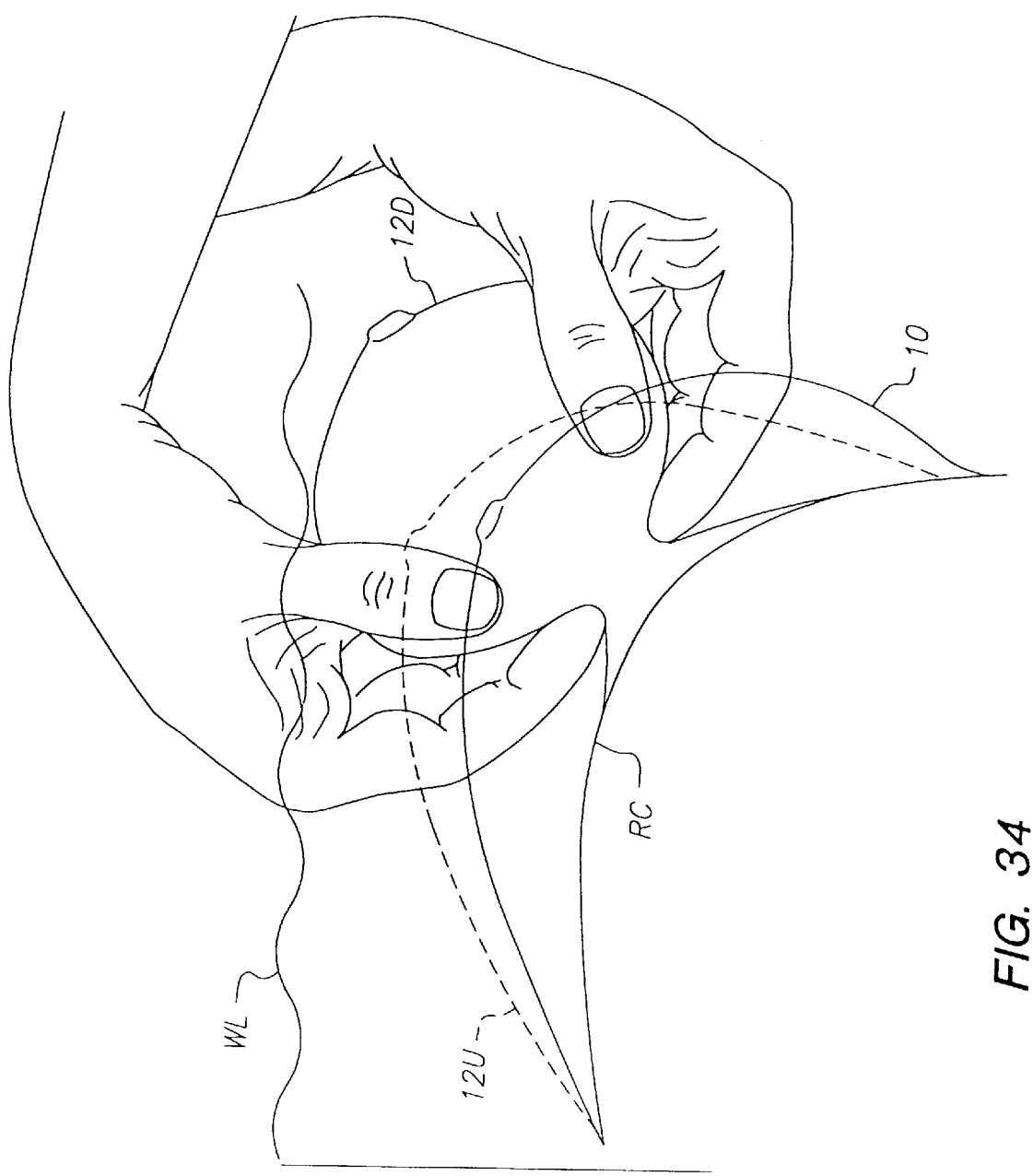
FIGS. 34 and 35 illustrate an examination procedure that is performed with the patient in a supine position with the rib cage rotated outward approximately forty-five degrees.
Figure 35:
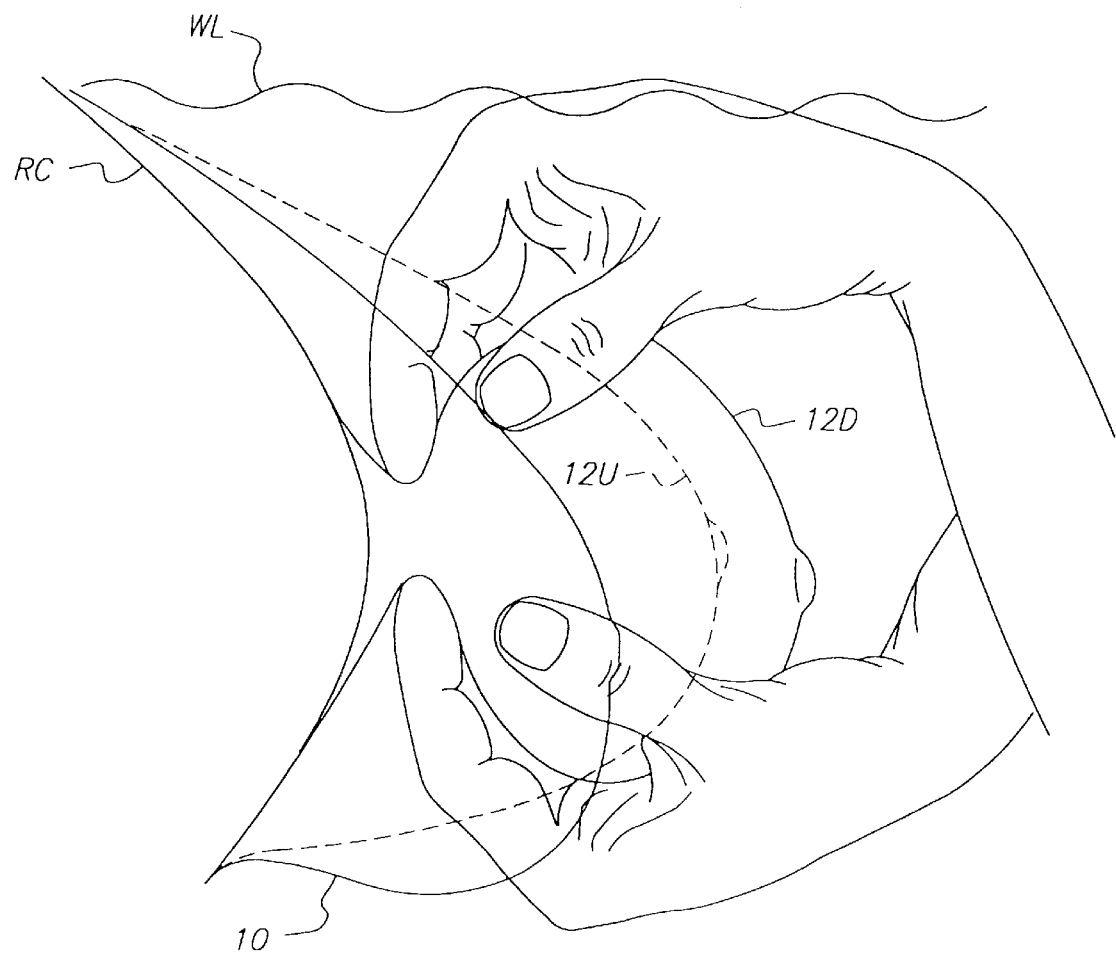

FIGS. 34 and 35 present side views of an examination performed while the patient's rib cage RC is rotated approximately forty-five degrees from a normal upright position. This technique is especially useful for patients having relatively large breasts. The rotation of the rib cage permits access to tissue overlying the lymph nodes and also allows for the examination of the pectoral muscle and tissues around the arm pit.

Figure 36:
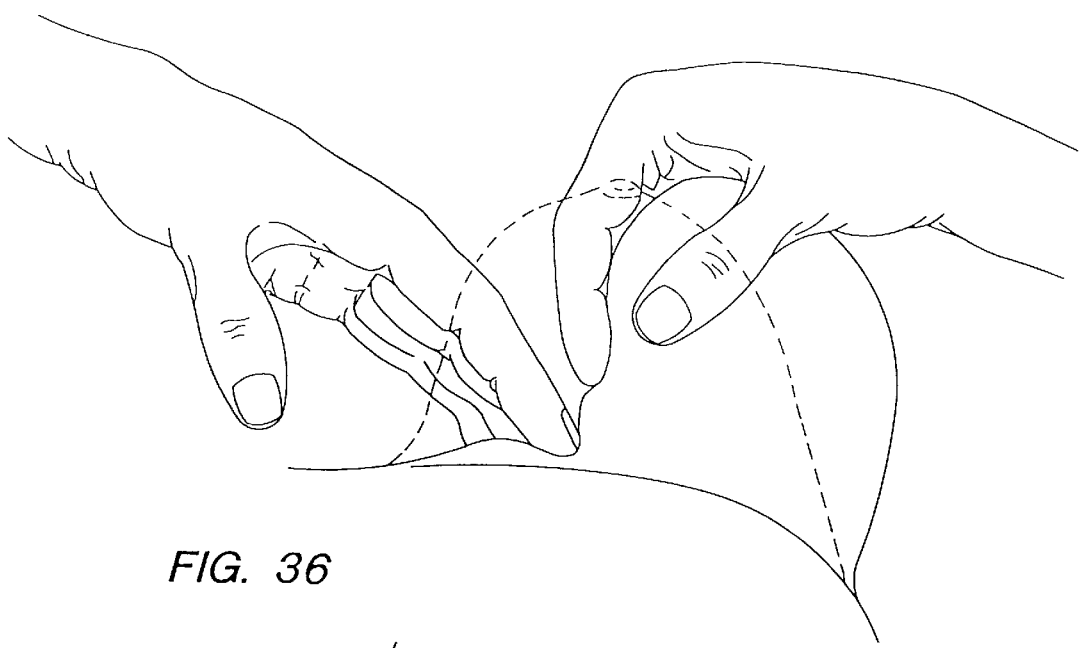
FIGS. 36 and 37 exhibit an examination procedure which is performed with the patient in an upright position.

FIG. 36 is an overhead view of an examination procedure in which the right breast is moved out to the patients right to permit the examiner to probe the breast tissue near the rib cage with the finger tips of the left hand.

Figure 37:
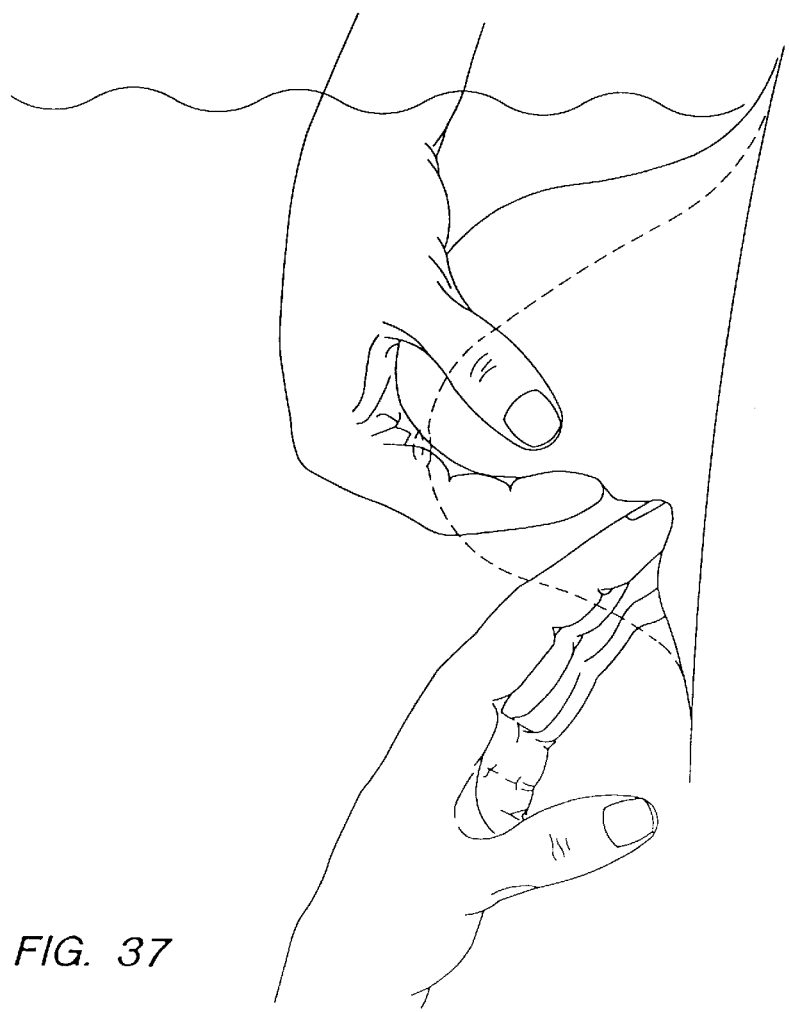

FIG. 37 is a side view which depicts an exam method in which the breast is lifted upward to access the tissue of the lower portion of the breast near the rib cage RC.

An important objective of the Finger Walk$^{SM}$ method is to use probing pressure to form a relatively constricted three-dimensional projection of tissue as seen in FIGS. 29 through 37. This projection is achieved by gently working the relaxed and levitated tissues into a shape which is more extended and stretched compared to the normal non-floatation position and shape. After the tissue is constricted and manipulated into a three-dimensional projection, the tissue is palpated using the fingertips (FT), as opposed to the flat portion of the fingers, to detect abnormalities.

Figure 38:
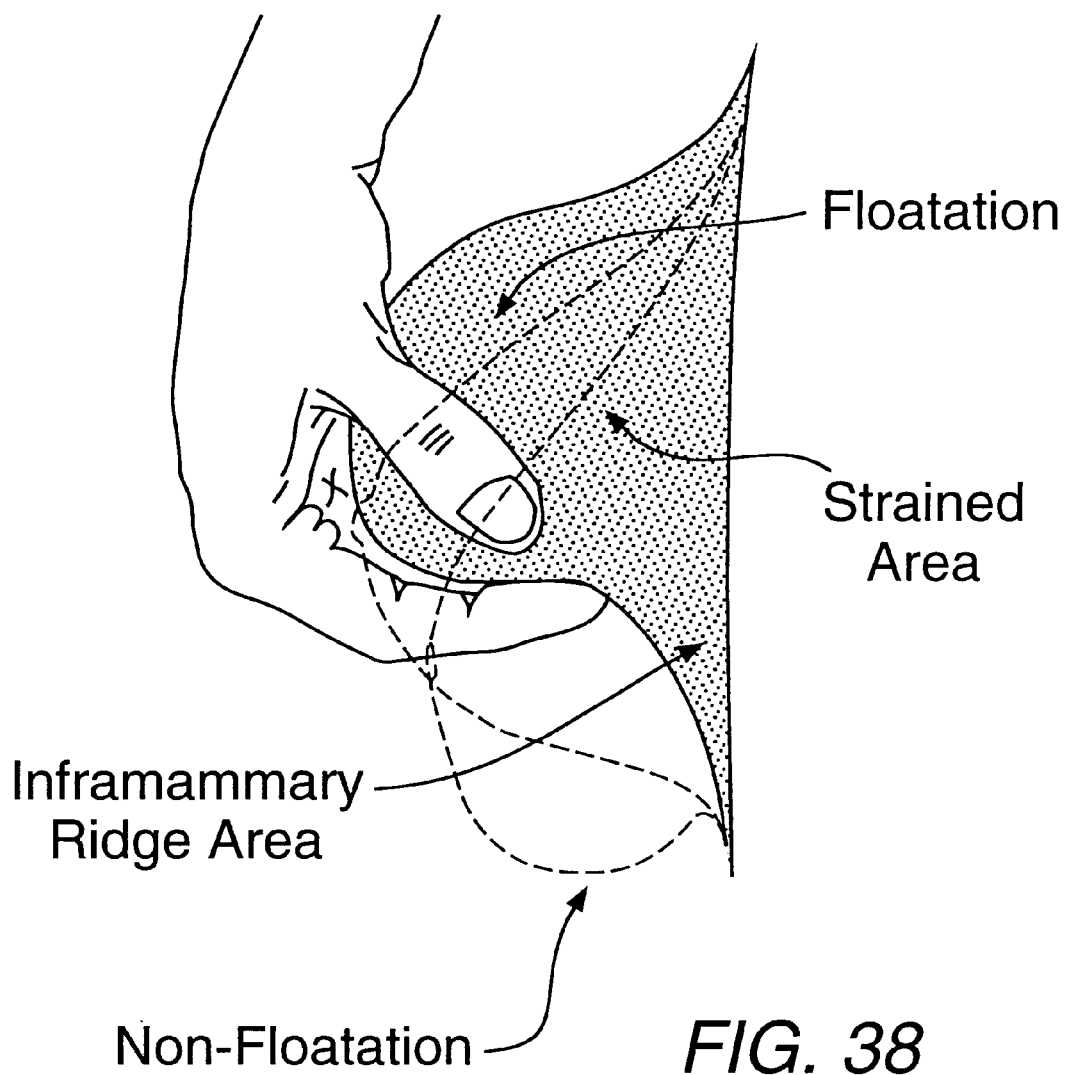
FIGS. 38 and 39 are a side views of a breast with the patient in a floatation bath in a generally upright position.
Figure 39:
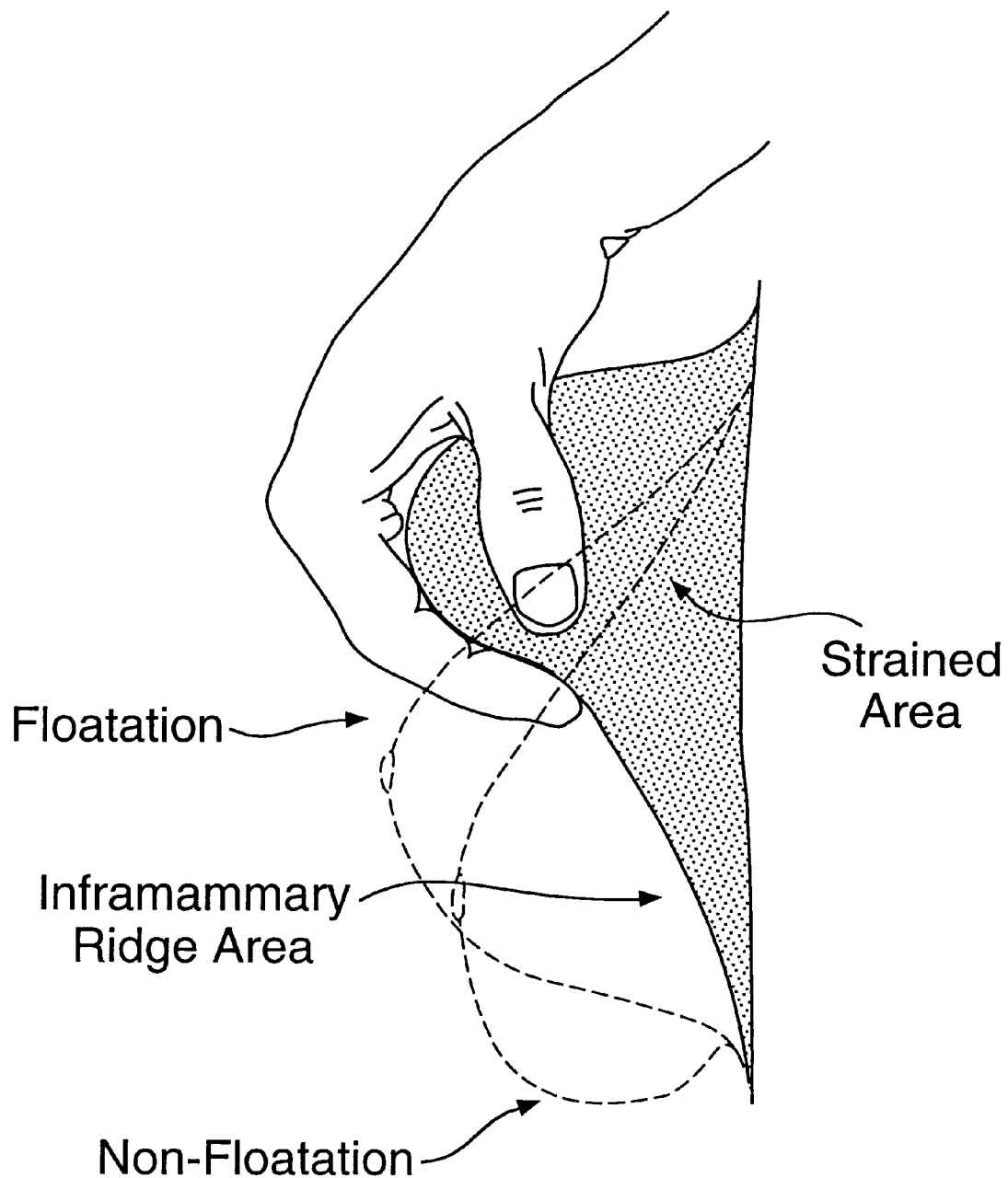

FIGS. 38 and 39 are a side views of a breast with the patient in a floatation bath in a generally upright position. In FIG. 38, the breast is being lifted to relieve the gravitational strain on the internal structure of the breast tissue. The breast tissue near the rib cage is progressively stroked in a upward motion toward the nipple with one hand. In FIG. 39, the breast has been lifted to a position near the upper limit of this palpation procedure.

Figure 40:
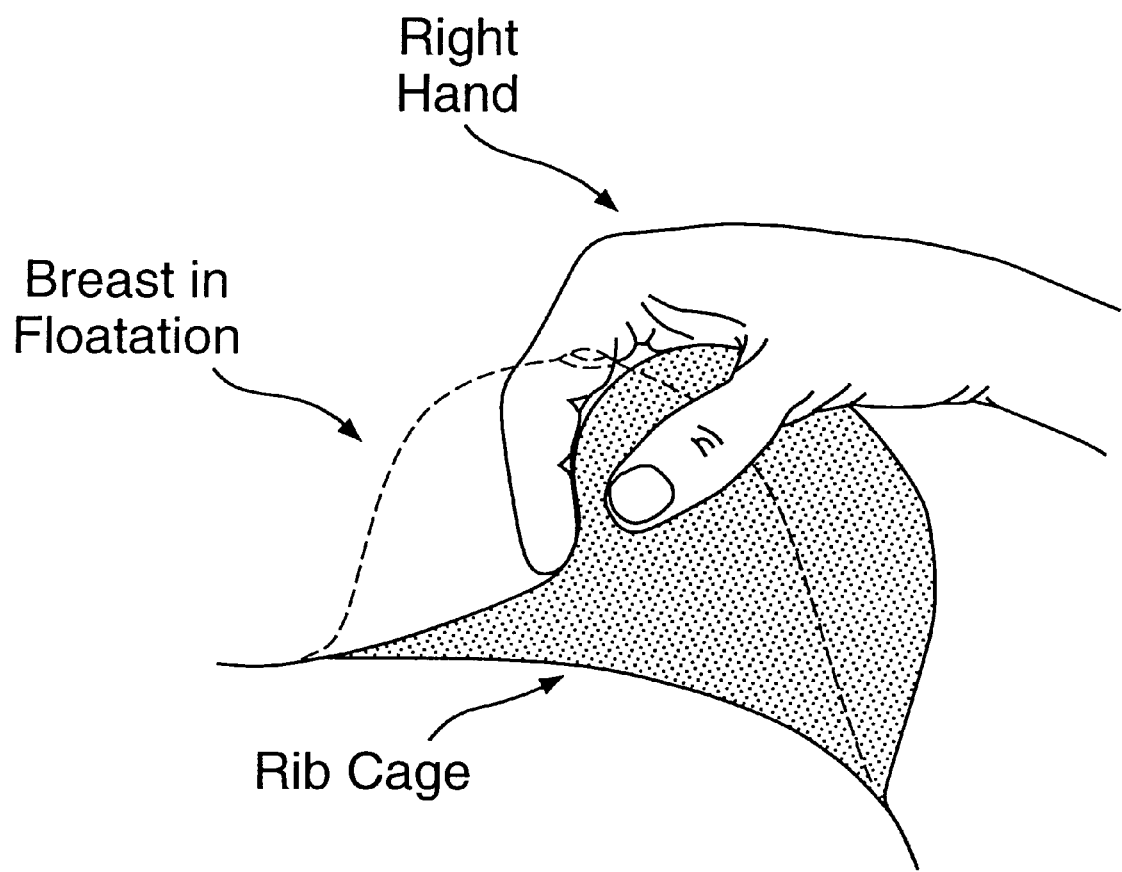
FIGS. 40, 41 and 42 are overhead views looking down on the right breast immersed in a floatation bath.
Figure 41:
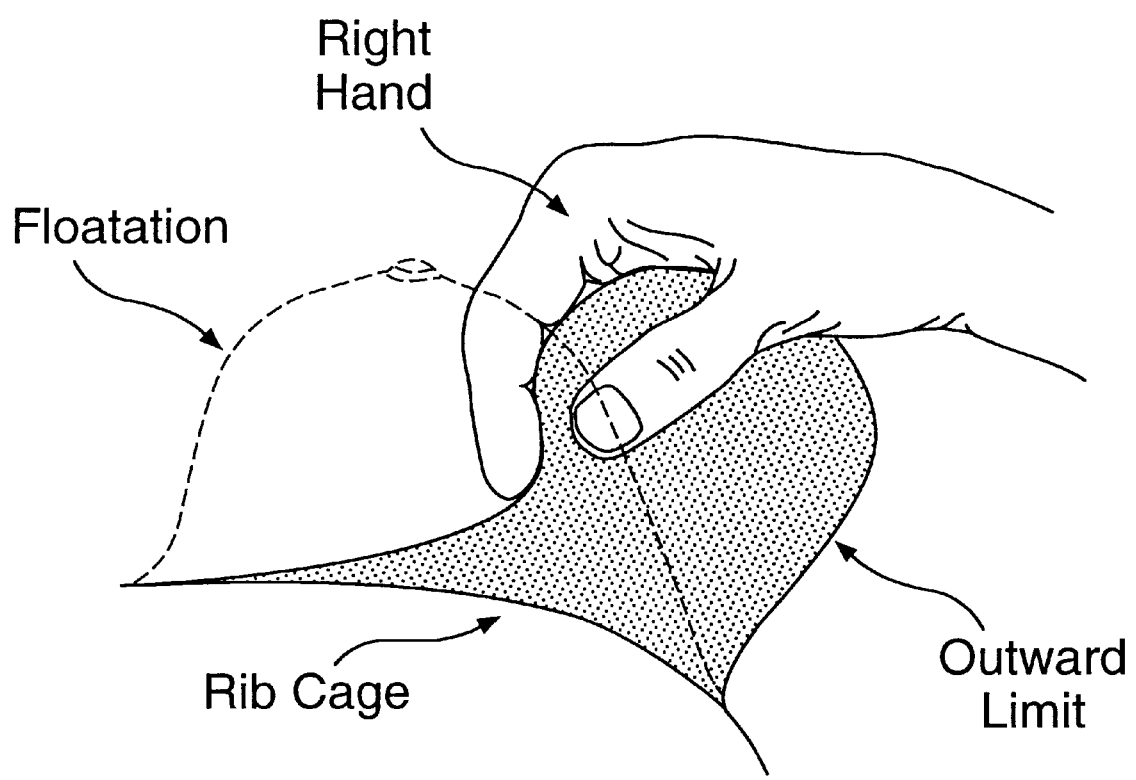
Figure 42:
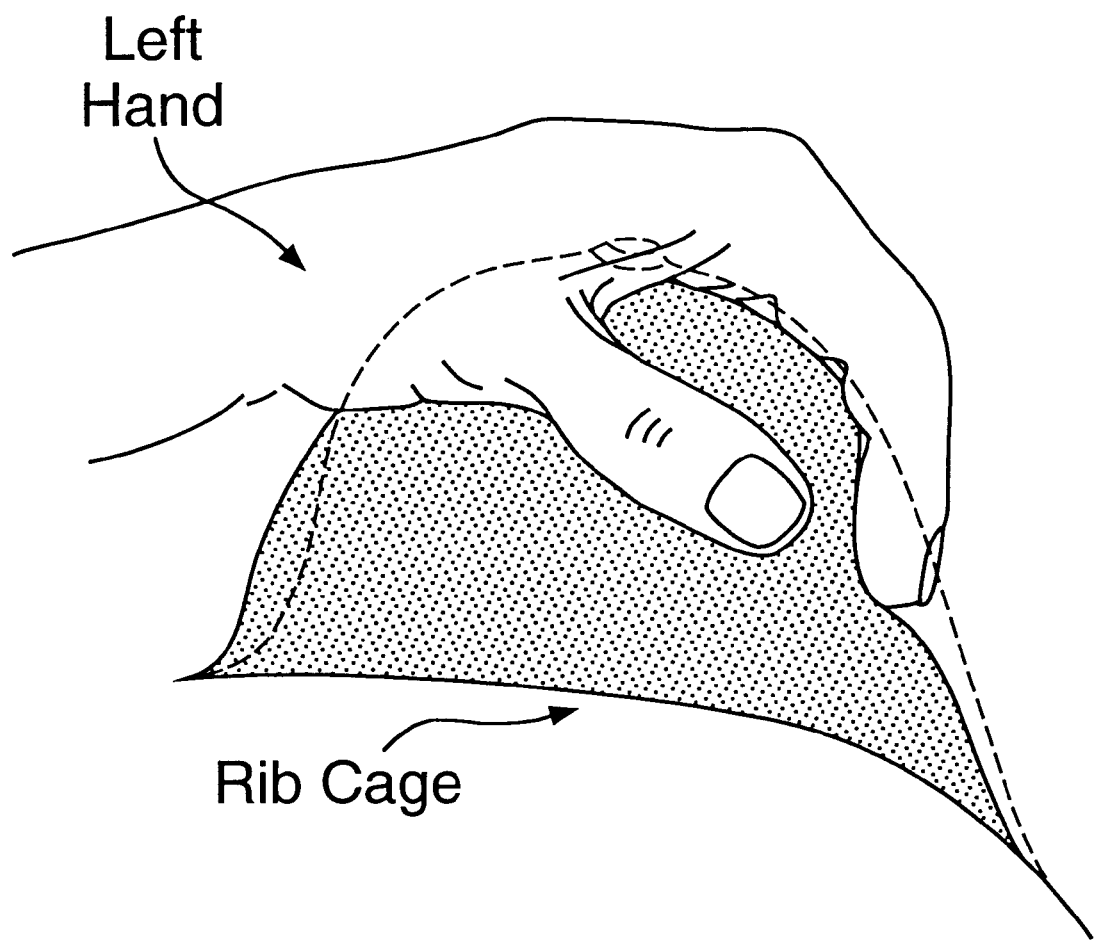

FIGS. 40, 41 and 42 are overhead views looking down on the right breast immersed in a floatation bath. In these figures, the breast is manipulated to relieve stress, to break up clusters in the internal tissue of the breast and to return the internal structure to its natural state. In FIG. 42, the hand is shown as it is gently pulsed in and out and then oscillated in a circular manner to assure that the internal structure finds its natural position. It is generally more comfortable for the patient to use her left hand for the right breast and the right hand for her left breast. This configuration maintains the breasts in an optimal relaxed position with minimal distortion due to arm position, and enables the examiner to massage the lumps residing in emulsified fatty tissue.

Figure 43:
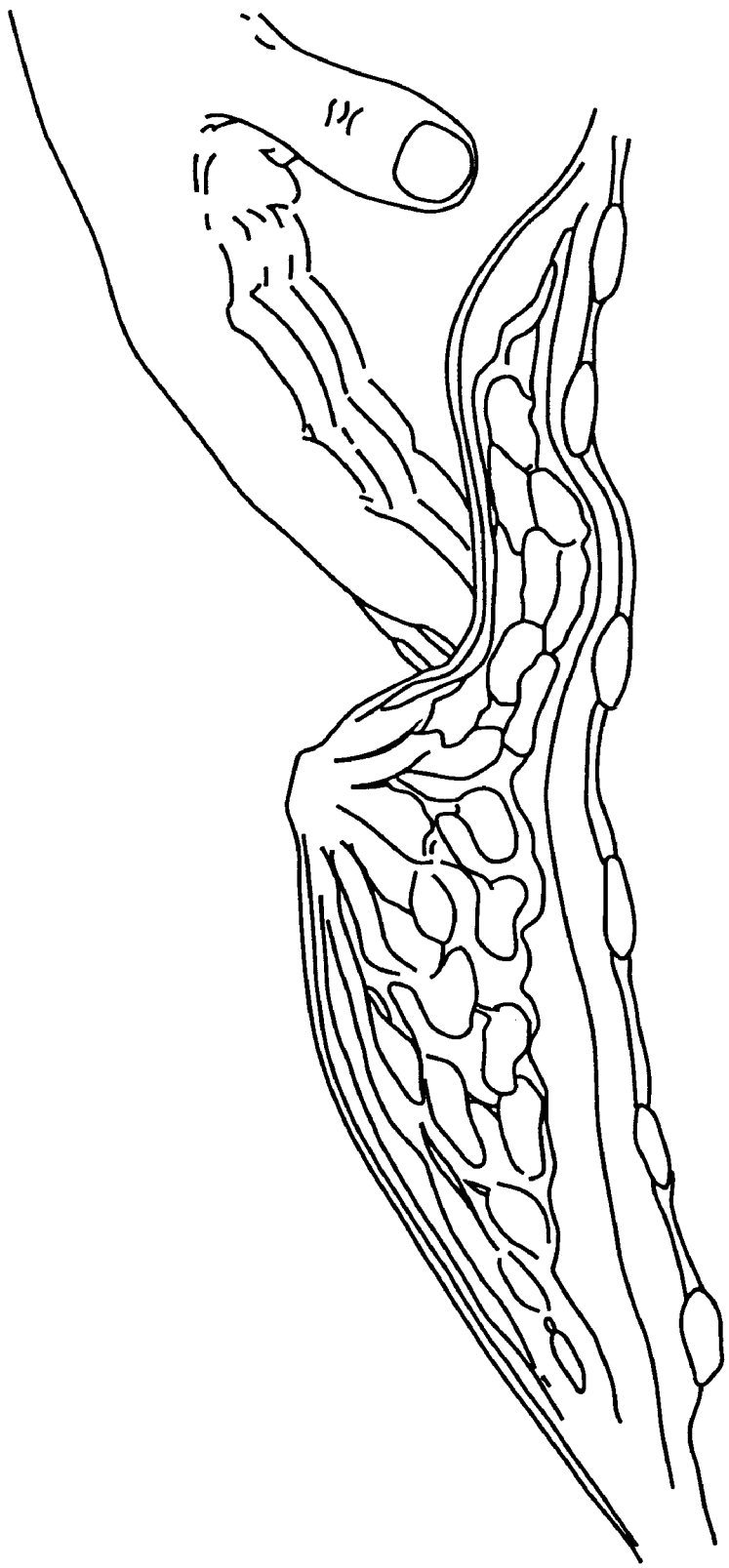
FIGS. 43, 44, 45 and 46 are partial cross-sectional views of the female breast as it would appear while the patient is in the supine position.
Figure 44:
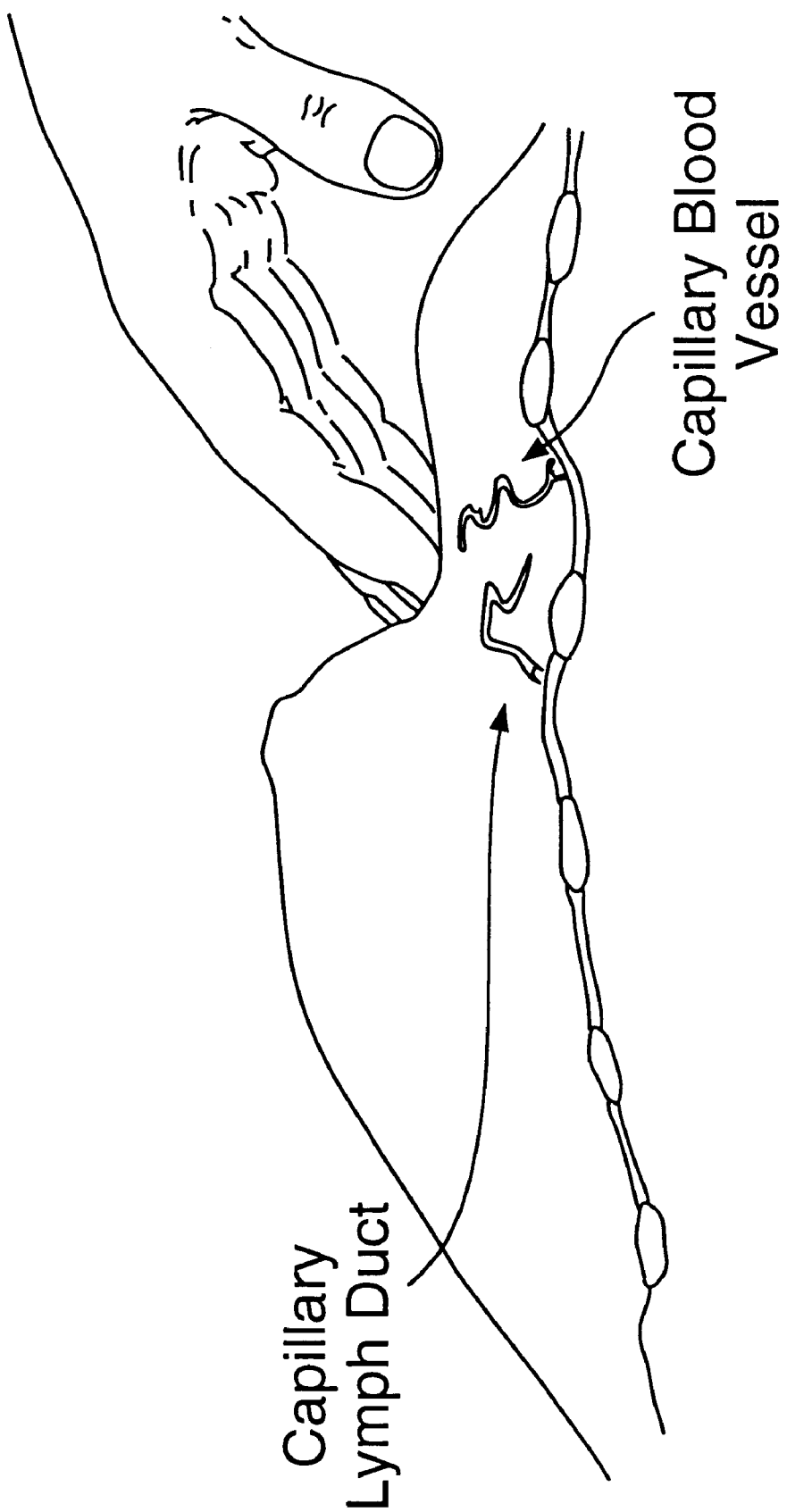
Figure 45:
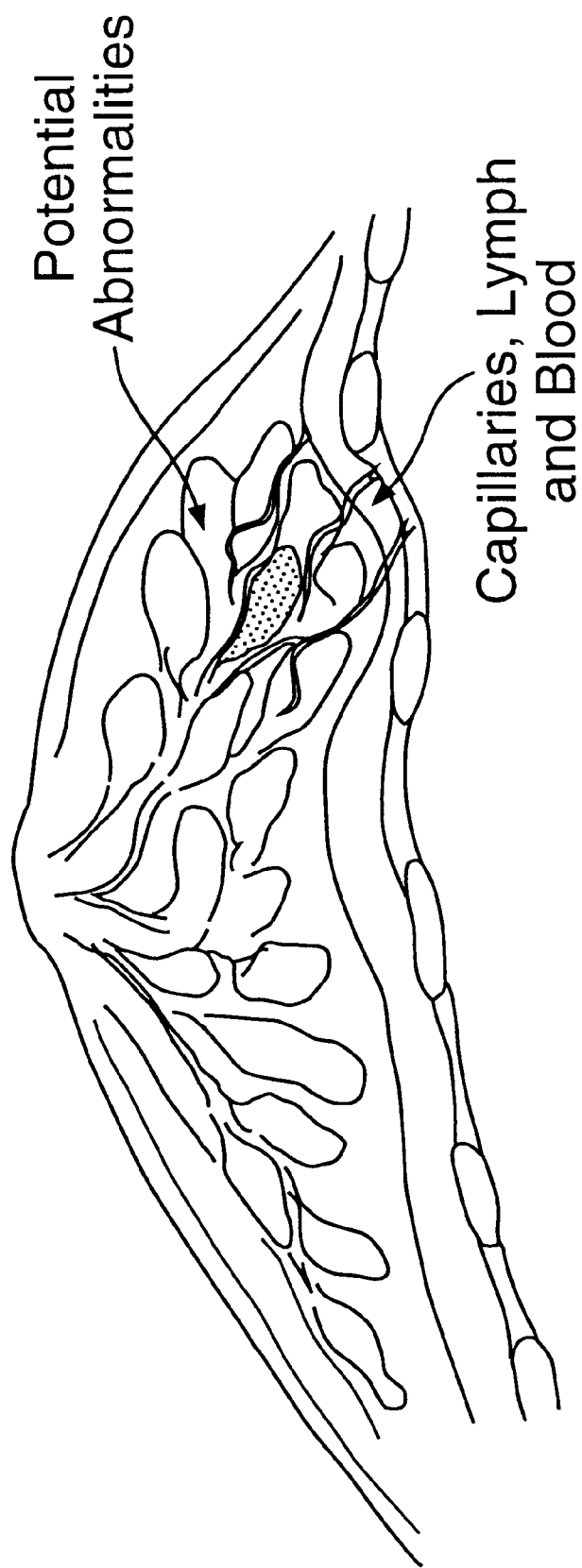
Figure 46:
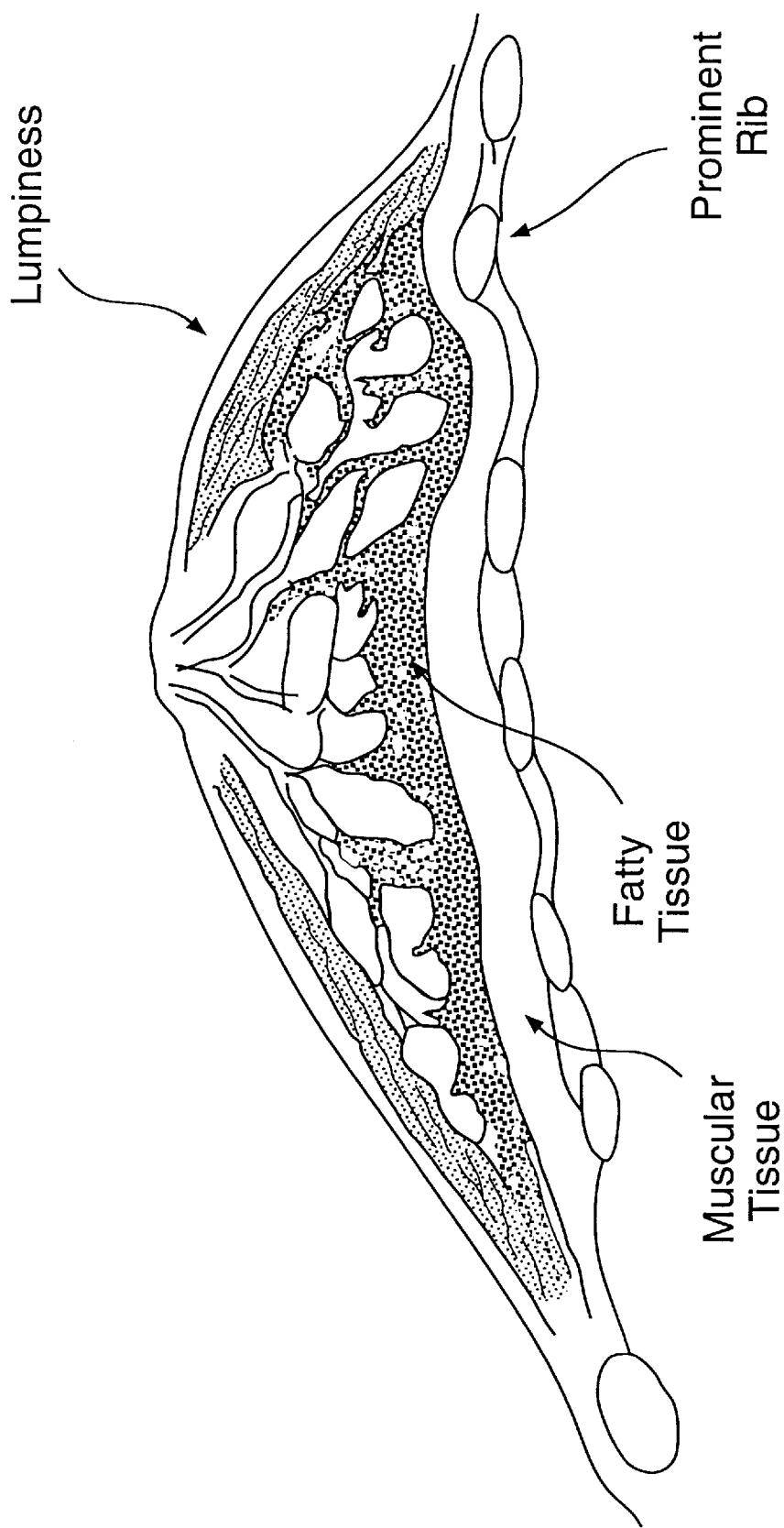

FIGS. 43, 44, 45 and 46 supply partial, cross-sectional views of the breast being massaged while the patient is in the supine position. FIG. 43 depicts the internal structures of the breast that may include lumps or clusters. These lumps or clusters may be held together by fatty tissue or may be entangled by lymph or blood vessels. FIG. 44 shows a capillary lymph duct and a capillary blood vessel. FIG. 45 suggests the structure of a potential abnormality. FIG. 46 reveals lumpy tissues, a prominent rib, and fatty and muscular tissues.

Figure 47:
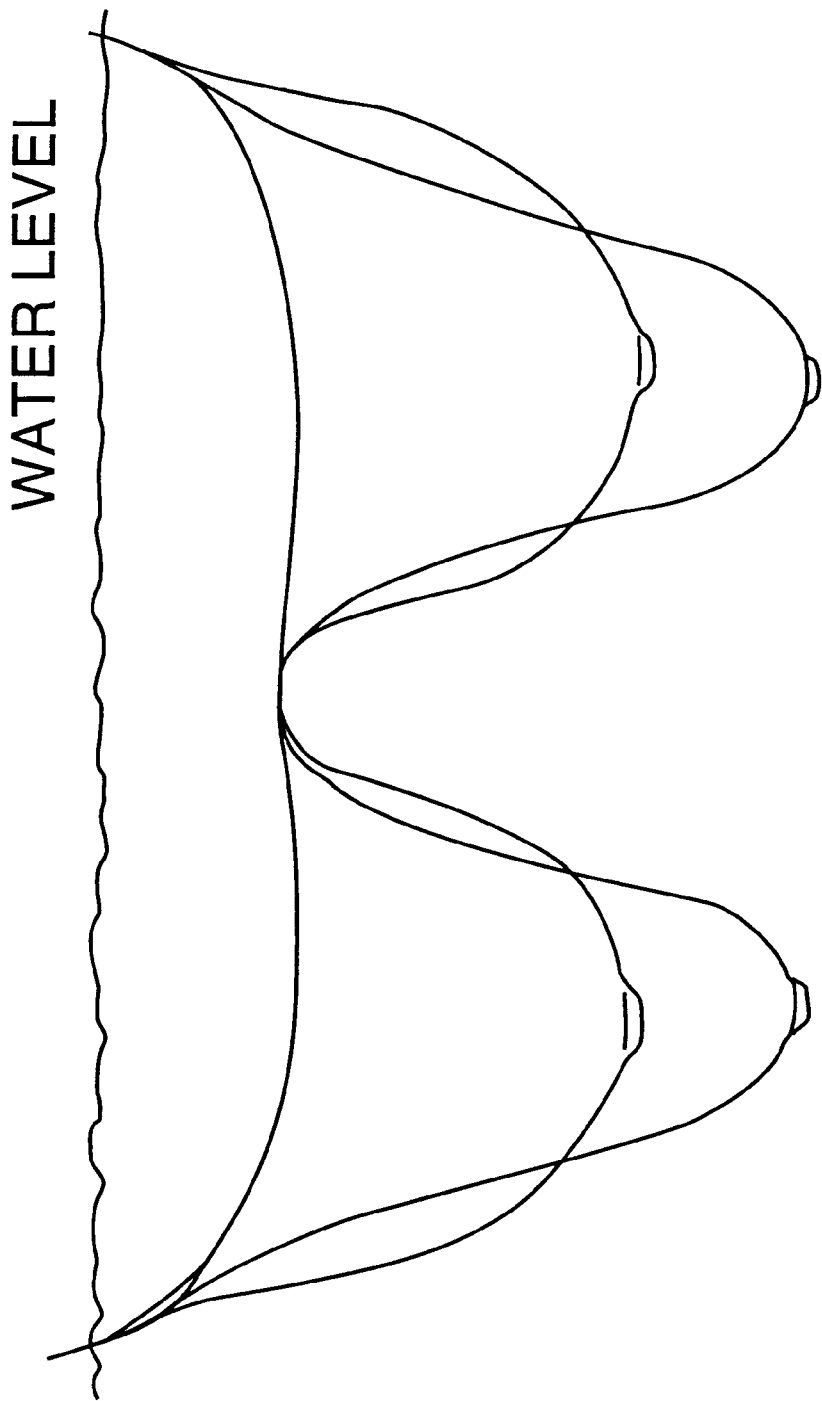
FIG. 47 compares the different shapes of the female breasts of a patient in a prone position with and without the levitating effects of floatation.

FIG. 47 compares the different shapes of the female breasts of a patient in a prone position with and without the levitating effects of floatation.

Figure 48:
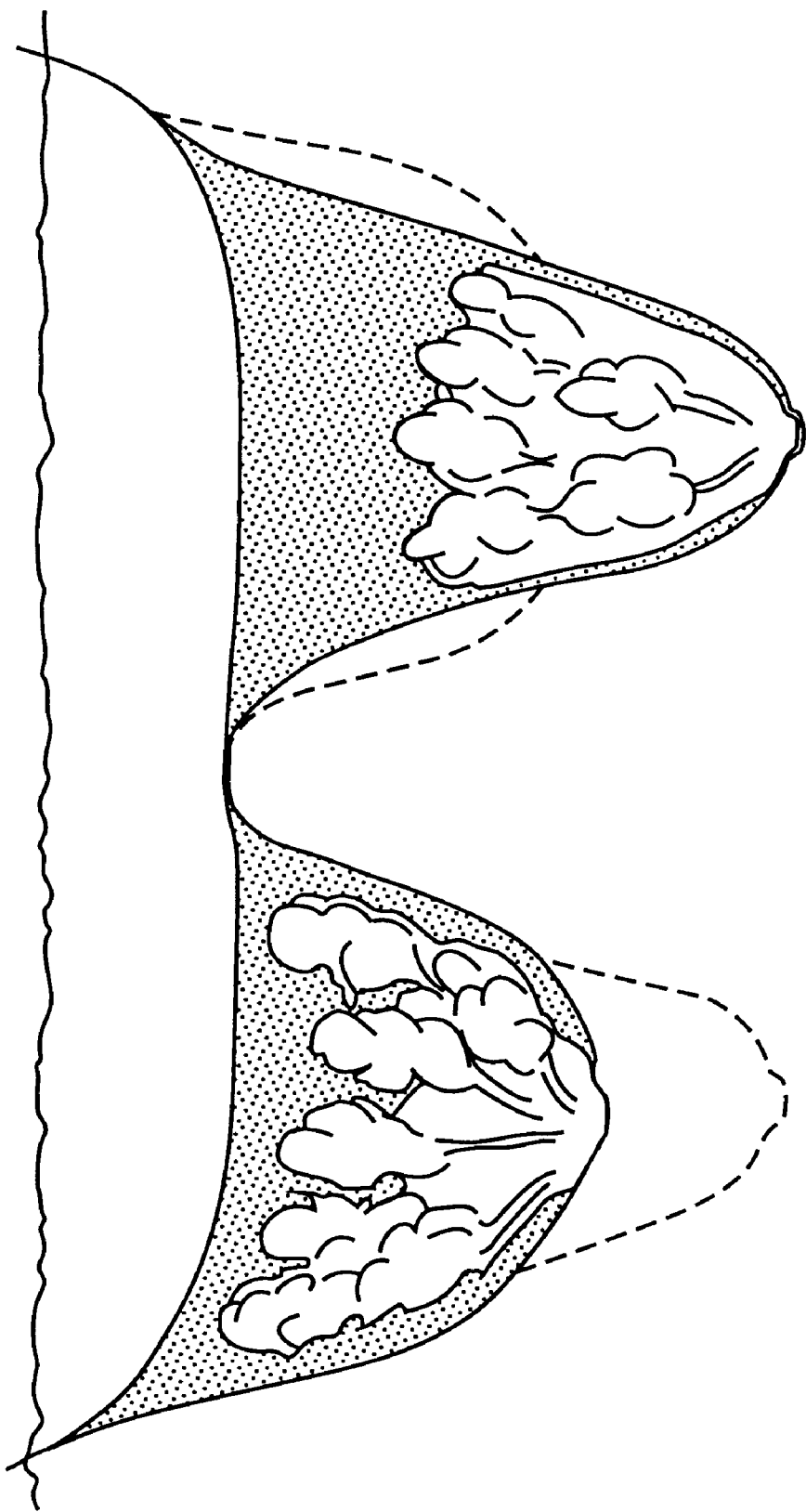
FIG. 48 reveals the migration of fatty tissue when a patient in a prone position immerses her breasts in water, while FIG. 49 portrays the emulsification of fatty tissue within the breast.
Figure 49:
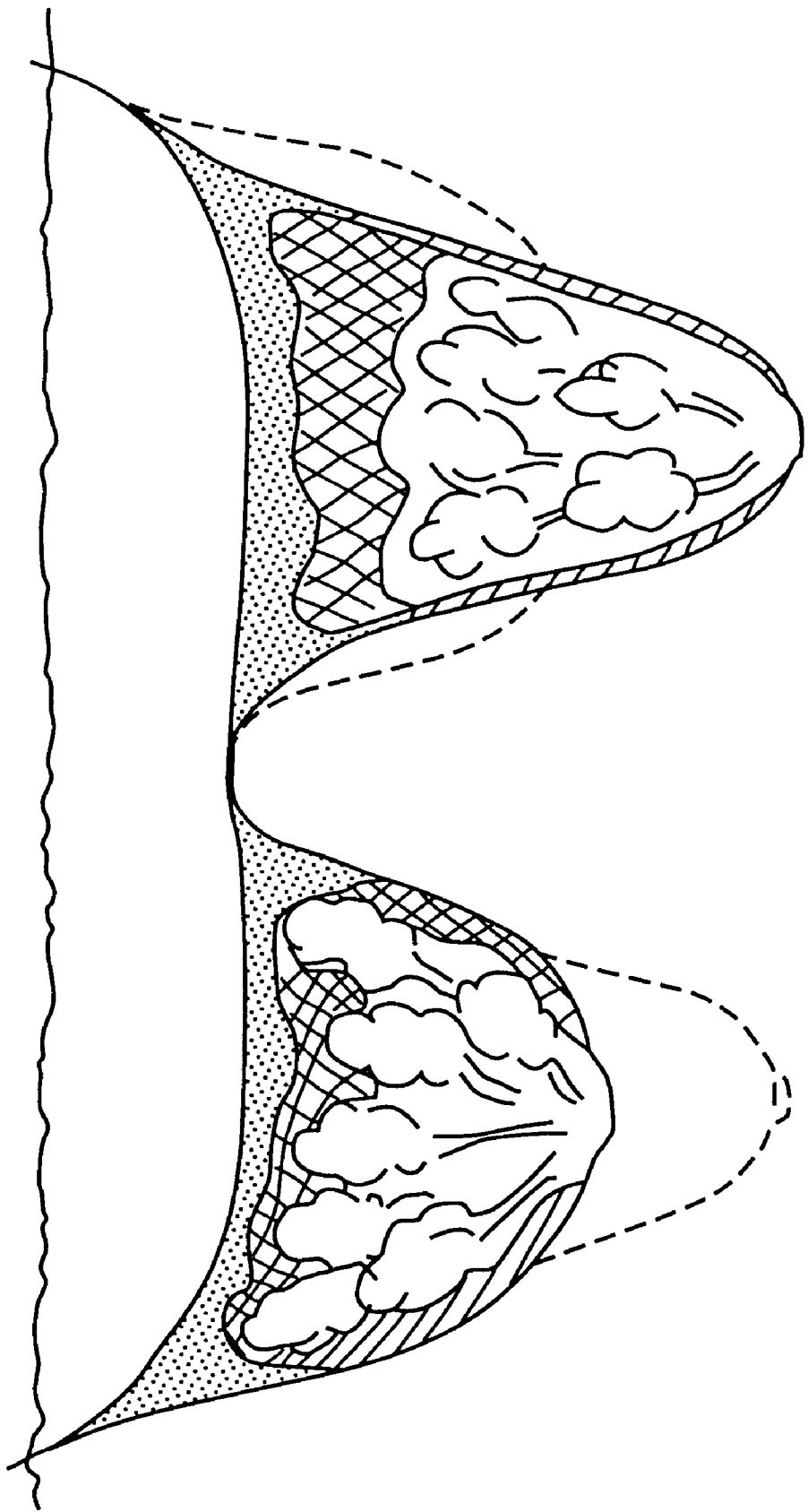
Figure 50:
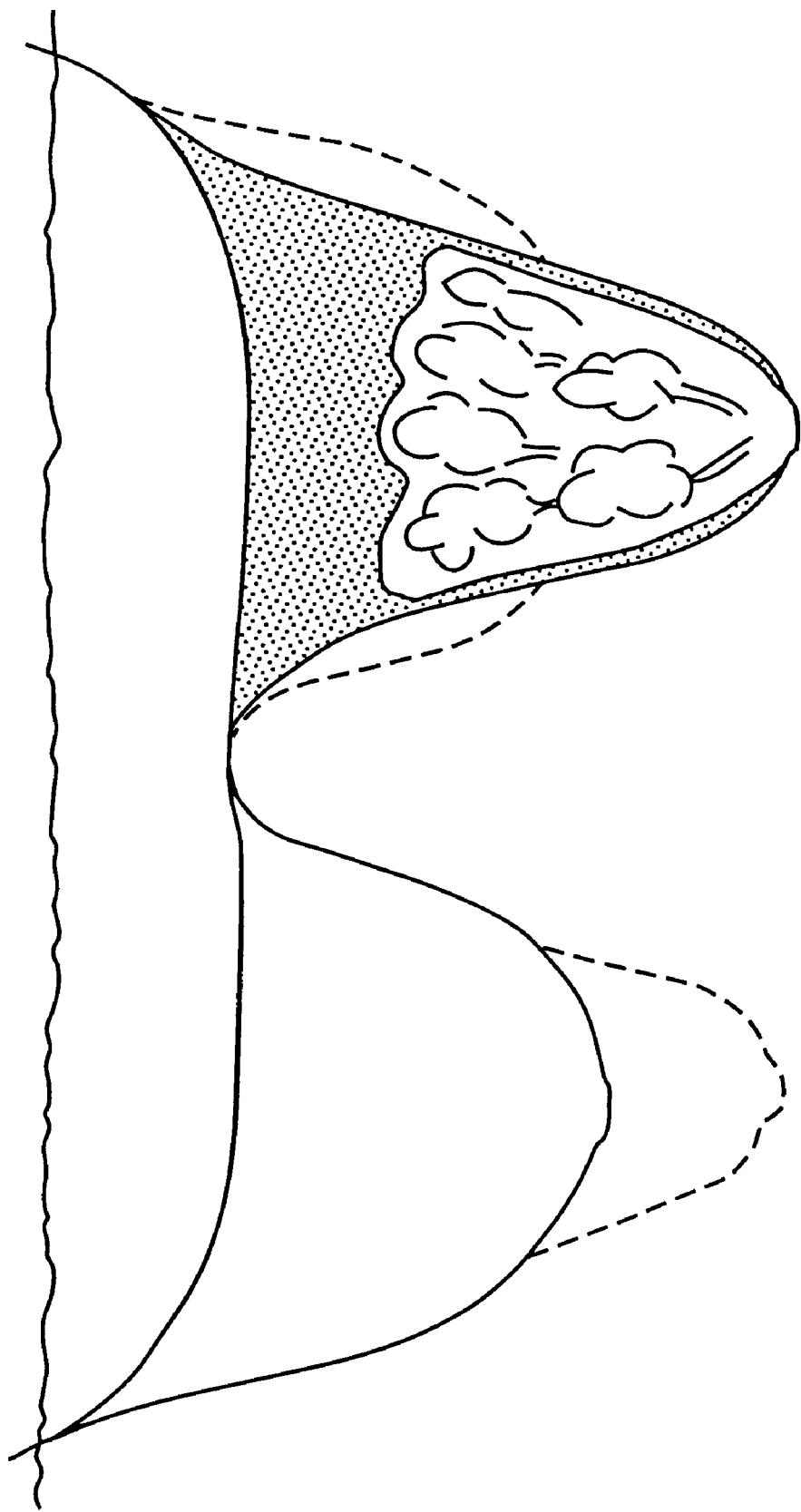
FIG. 50 illustrates the condition of the fatty tissue after submersion in a hot bath followed by cooling to room temperature.

FIG. 48 reveals the migration of fatty tissue when a patient in a prone position immerses her breasts in water, while FIG. 49 portrays the emulsification of fatty tissue within the breast after immersion for twenty minutes. In FIG. 49, the non-emulsified areas are indicated by the darker shading. FIG. 50 illustrates the condition of the fatty tissue after submersion in a hot bath followed by cooling to room temperature.

Figure 51:
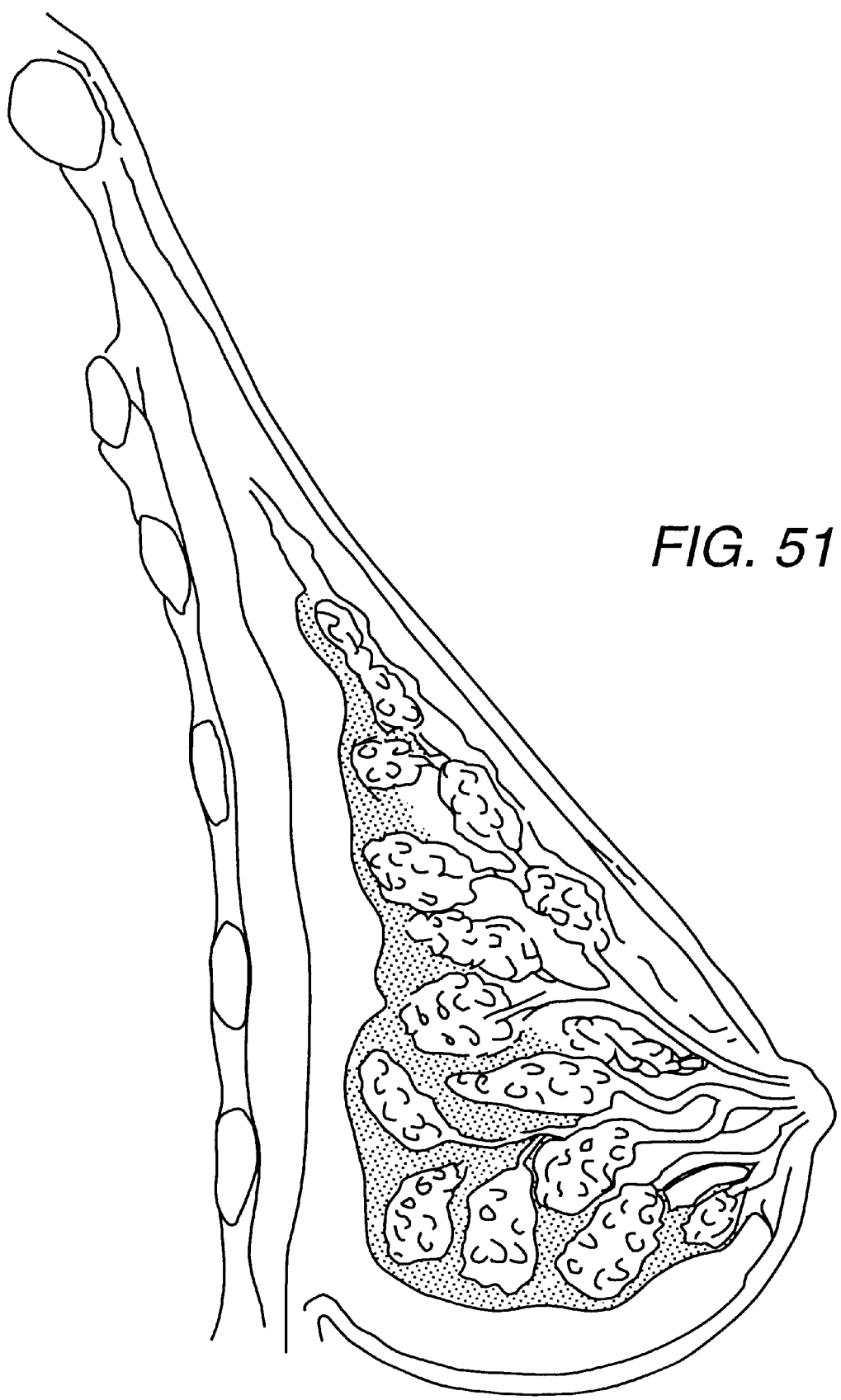
FIG. 51 shows a breast in cross-section while the patient is in an upright position, and reveals the migration of fatty tissue.
Figure 52:
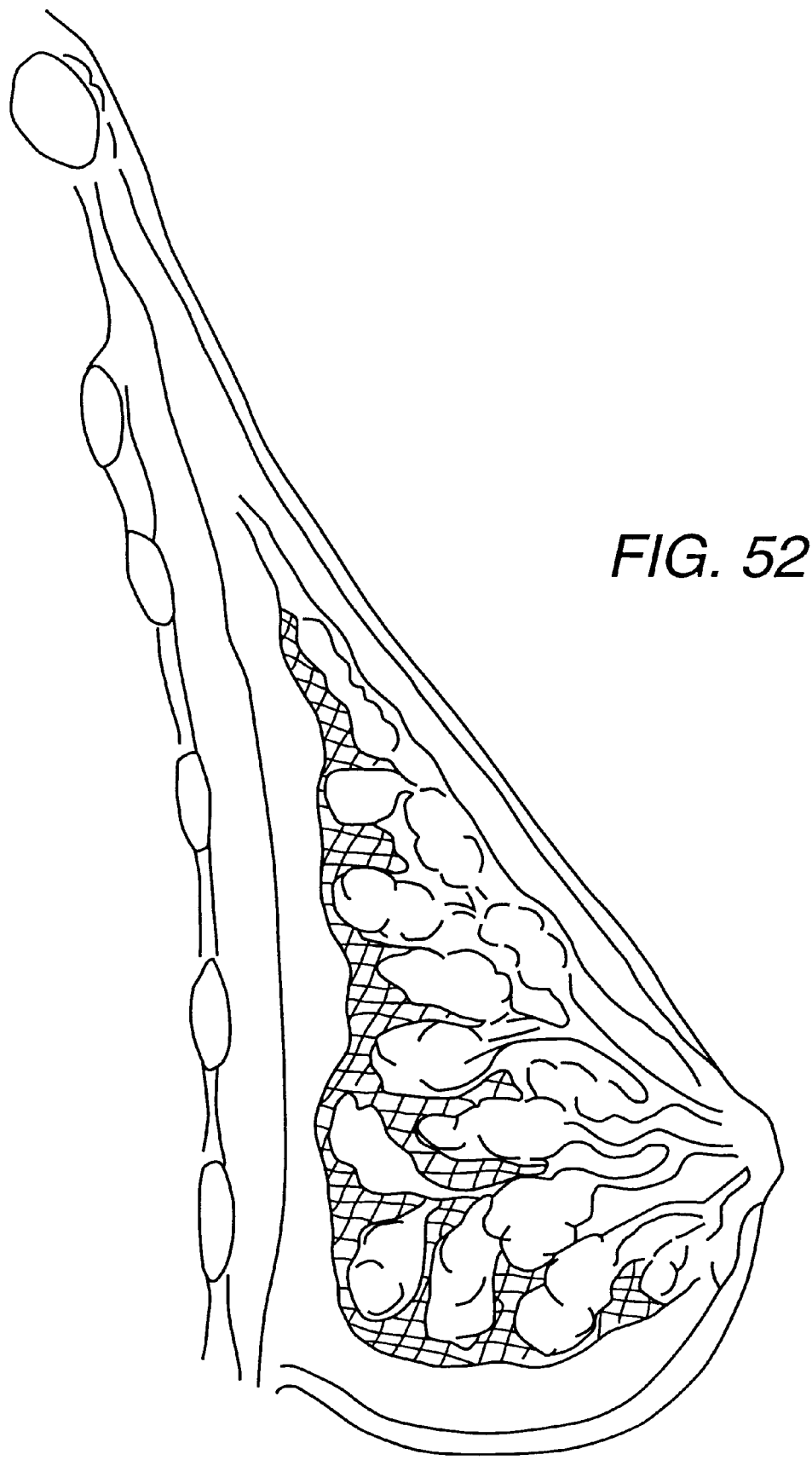
FIGS. 52 and 53 provide the same view as FIG. 51, but after a hot bath and massage.
Figure 53:
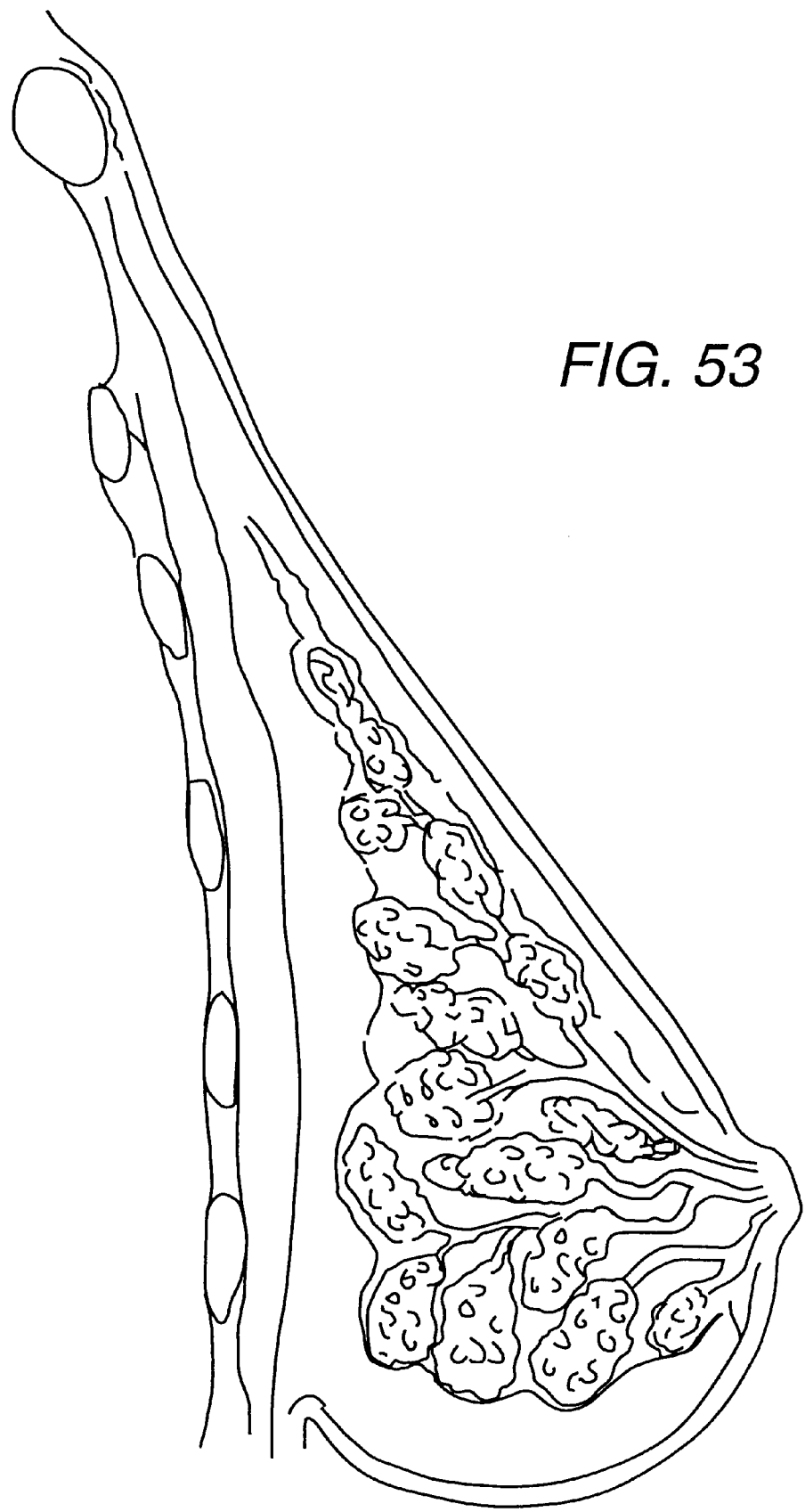

FIG. 51 shows a breast in cross-section while the patient is in an upright position, and reveals the migration of fatty tissue. FIGS. 52 and 53 provide the same view as FIG. 51, but after a hot bath and massage.

Figure 54:
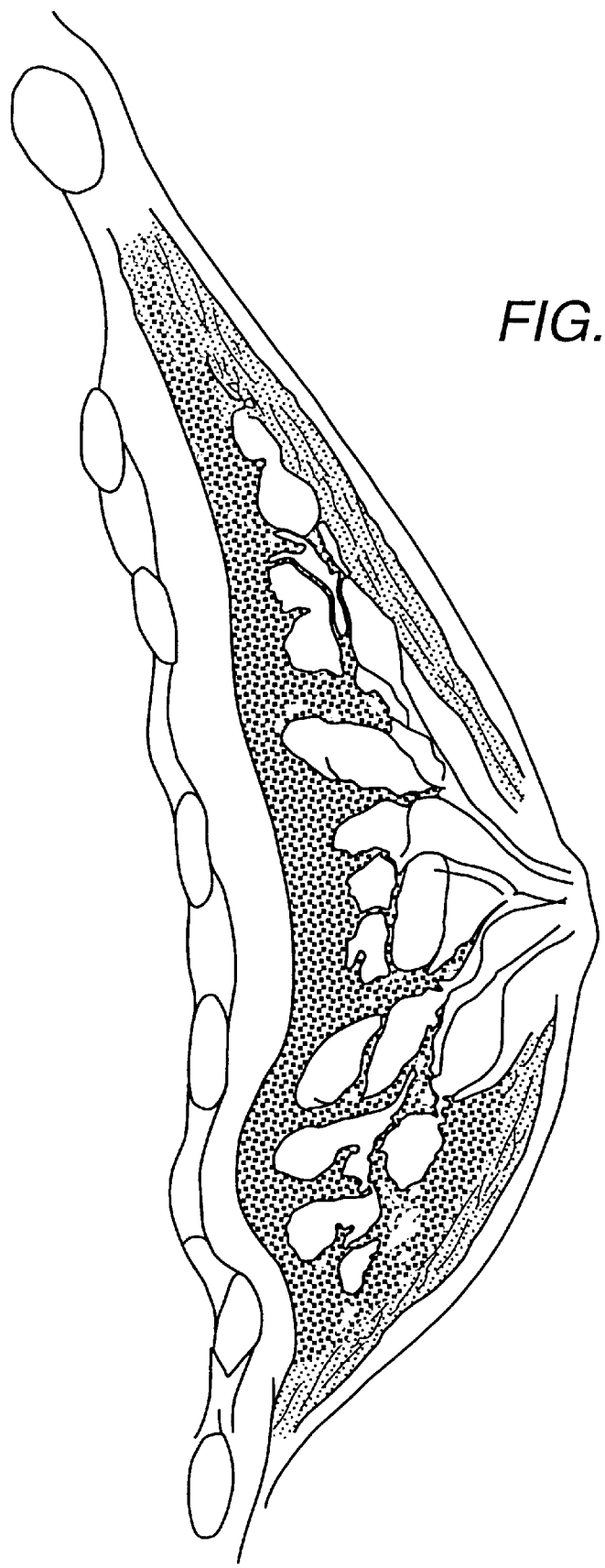
FIG. 54 shows the fatty tissue migration into the internal structure of the breast when the patient is in a supine position.
Figure 55:
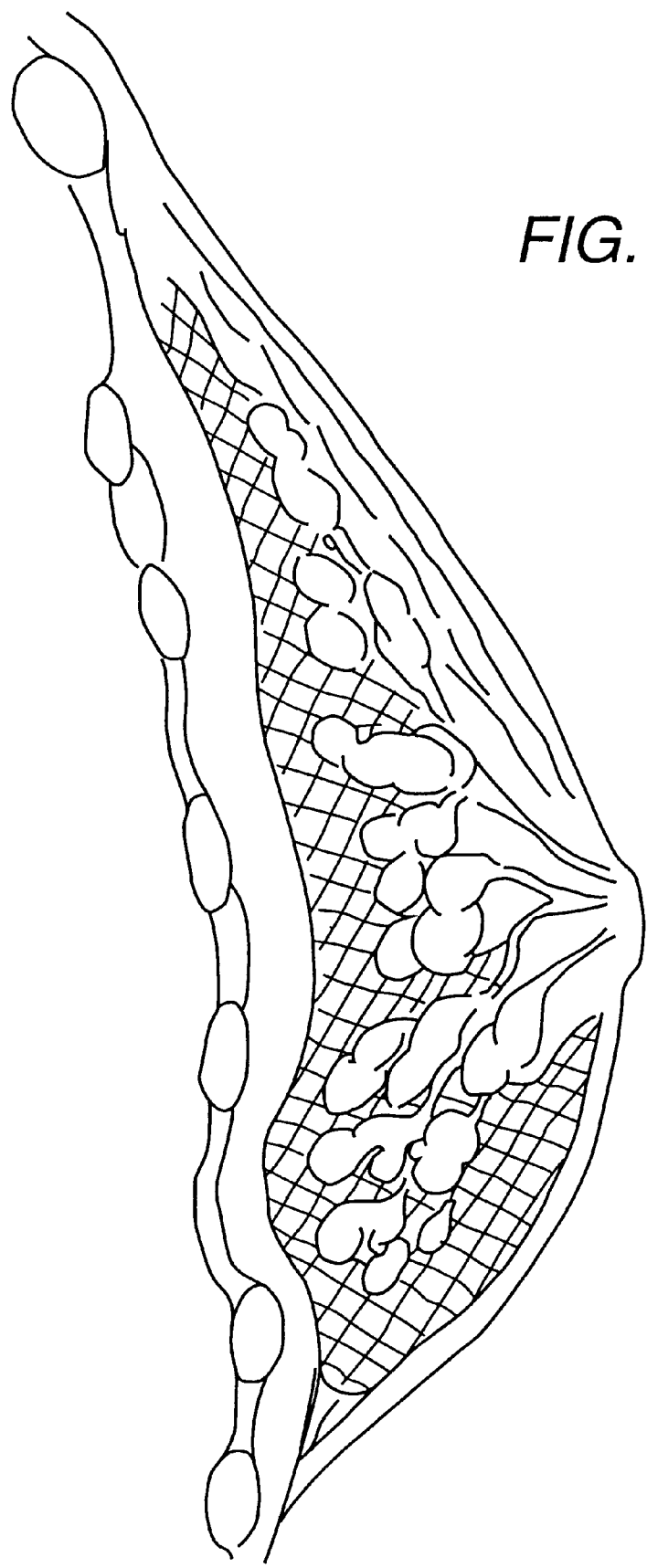
Figure 56:
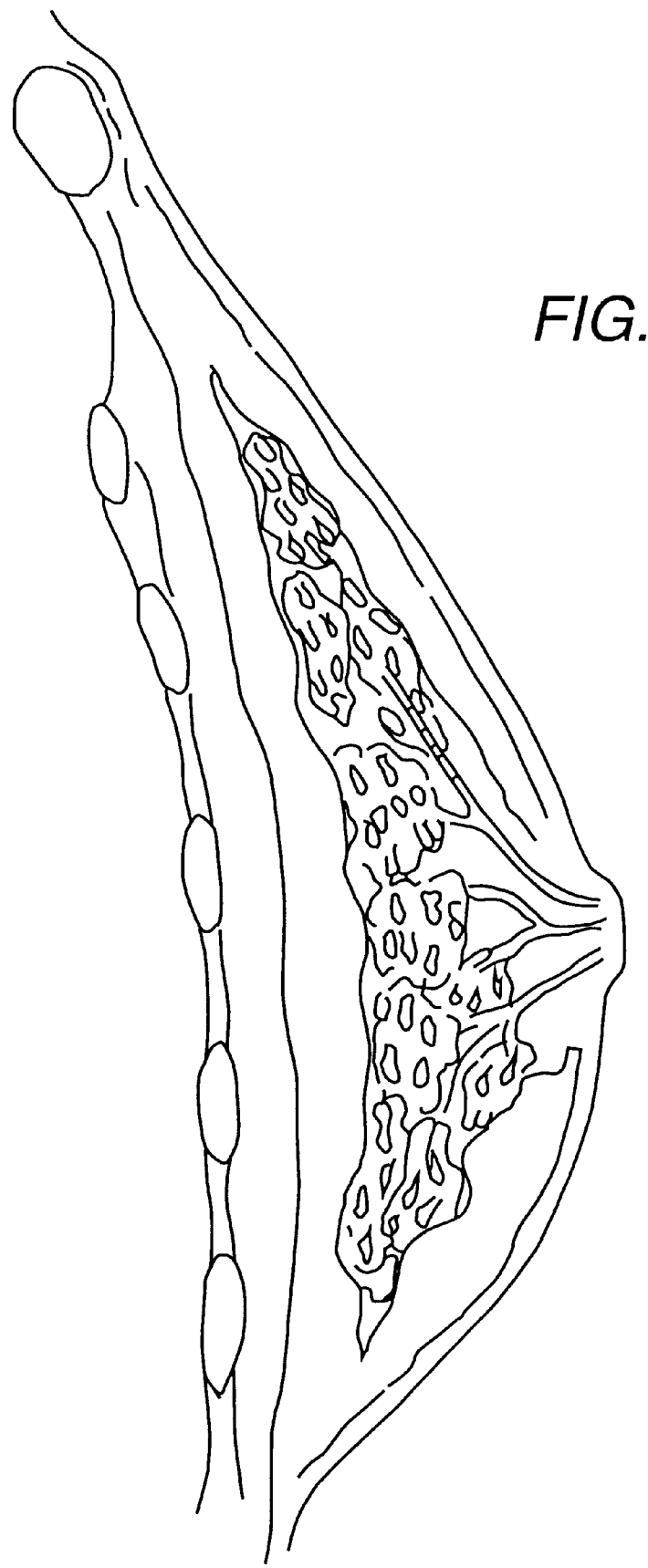
FIG. 56 illustrates the same tissue after it is cooled to normal body temperature.

FIG. 54 shows the fatty tissue migration into the internal structure of the breast when the patient is in a supine position. FIG. 55 shows the same breast after the emulsification that occurs during a hot bath and massage, while FIG. 56 illustrates the same tissue after it is cooled to normal body temperature.

Figure 57:
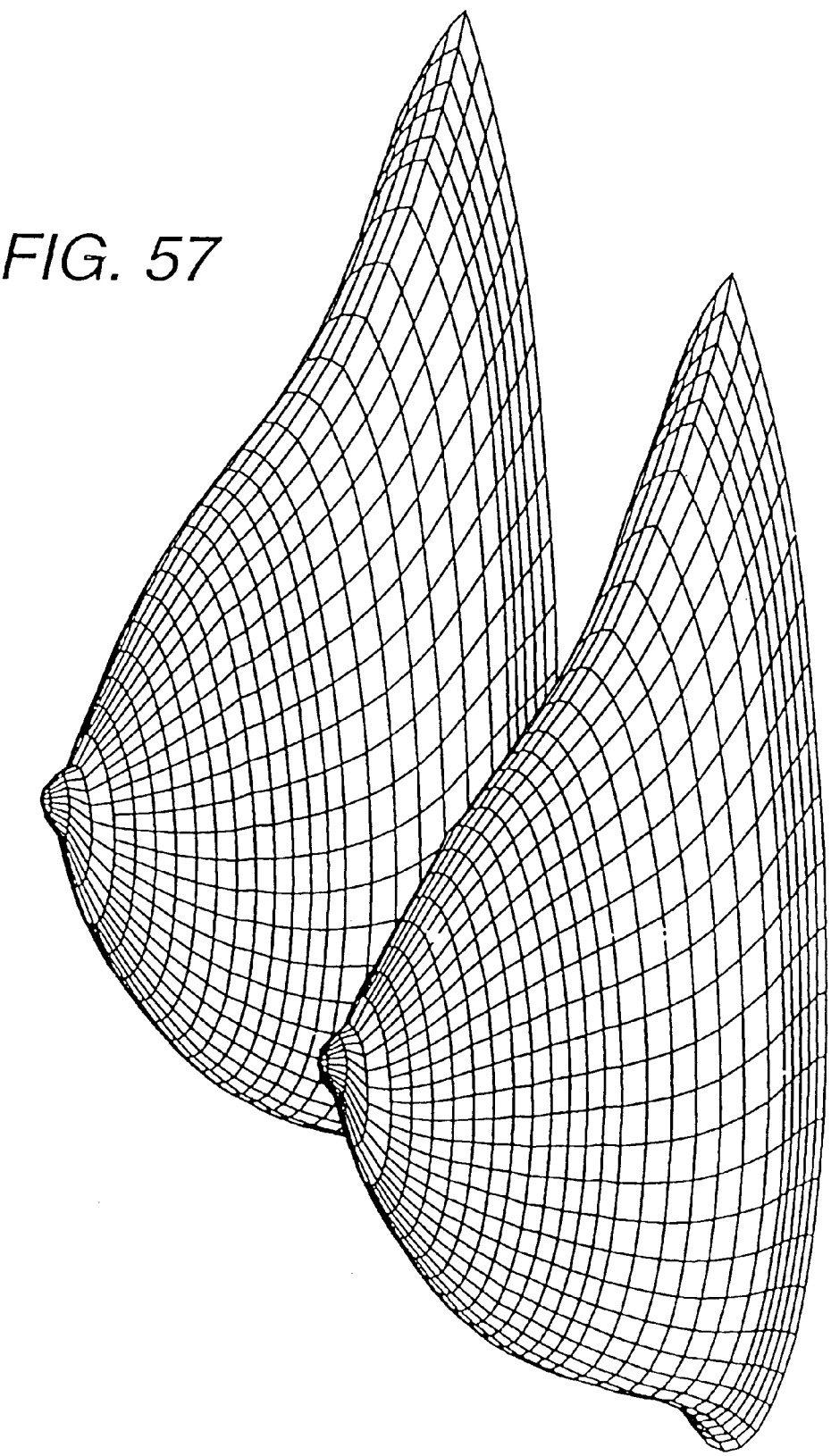
Figure 58:
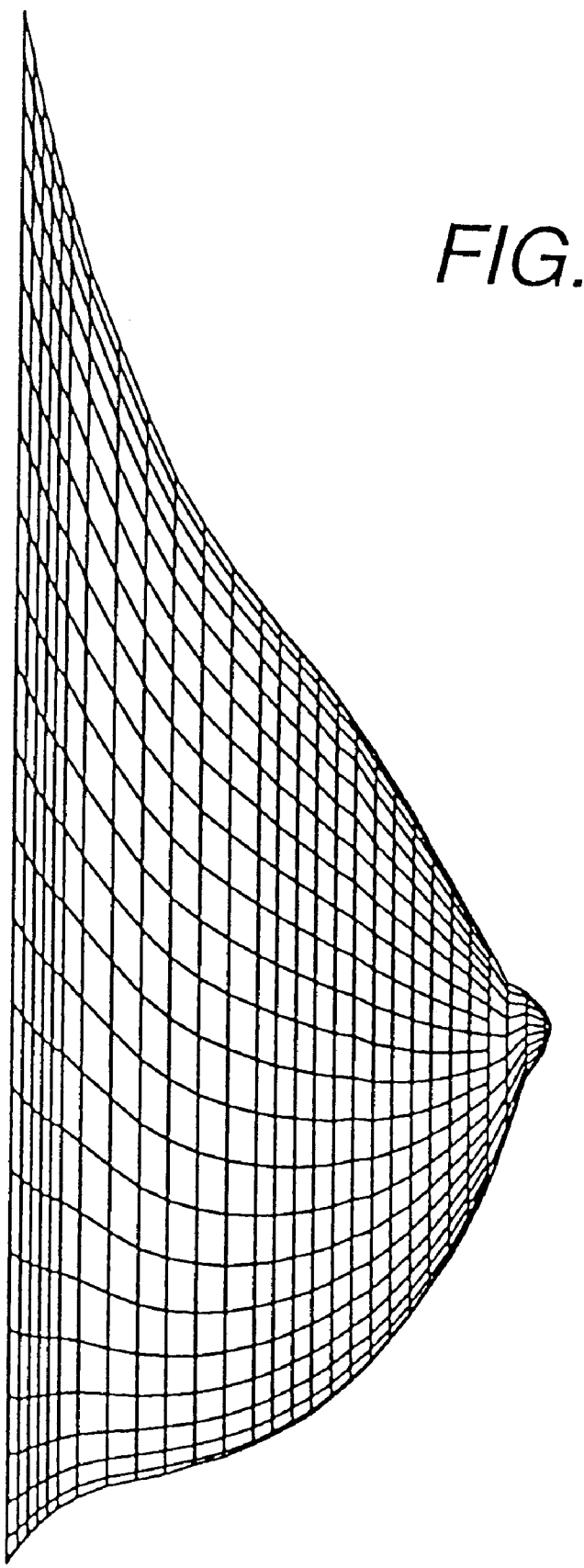
Figure 61:
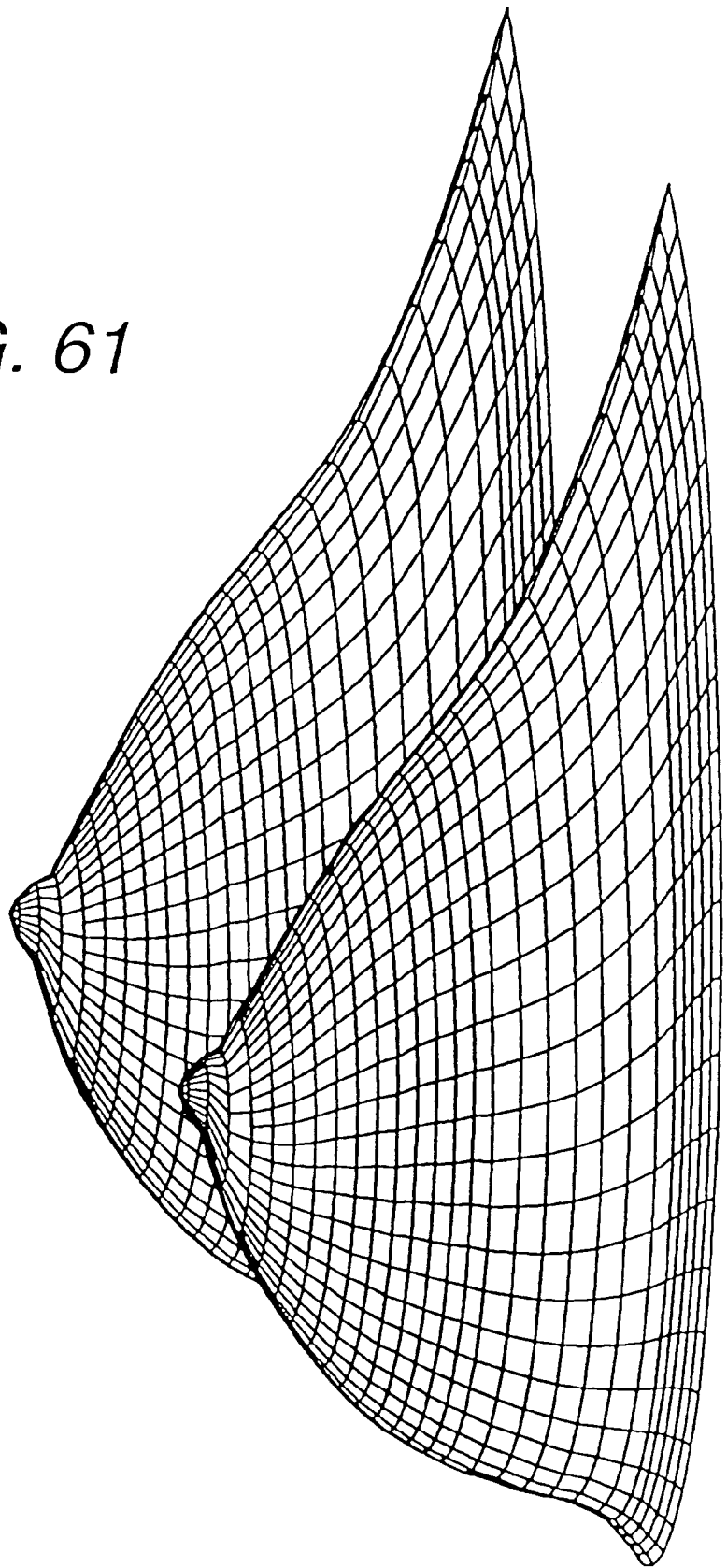
Figure 64:
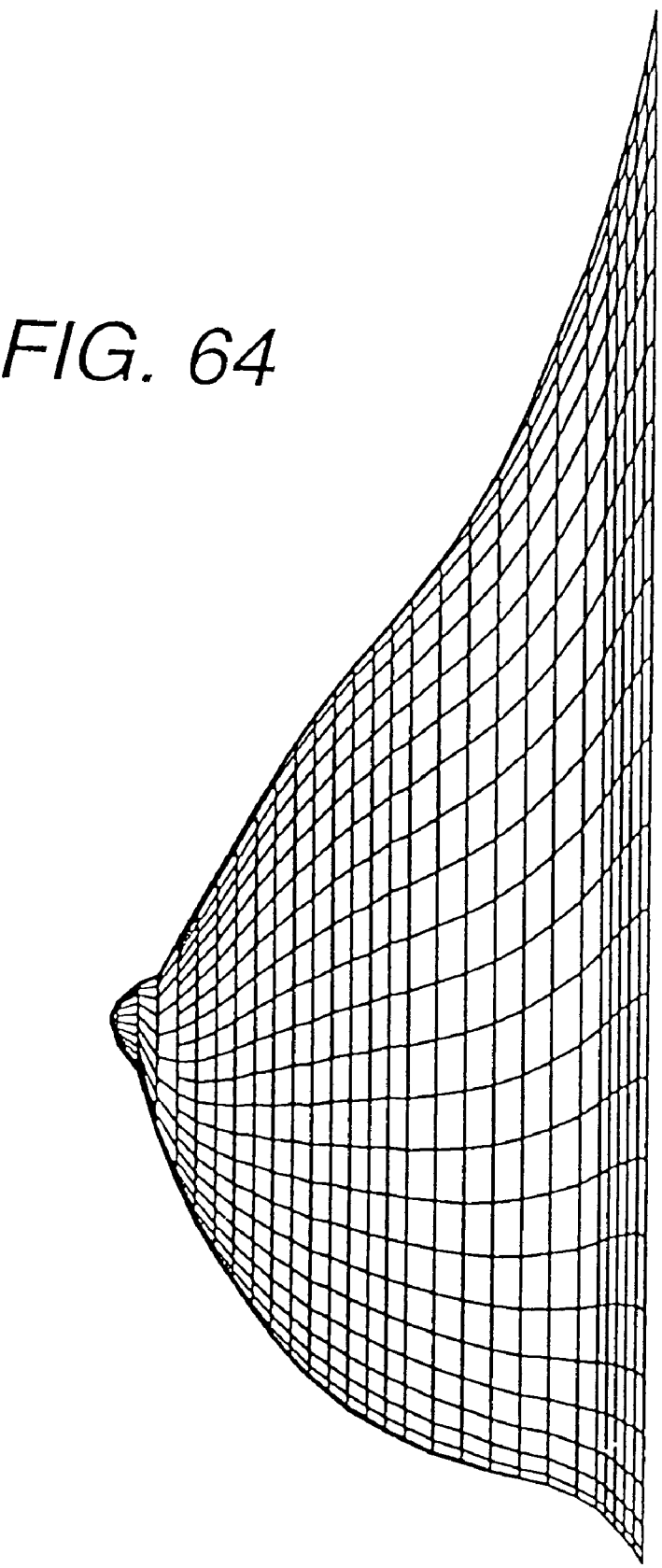

FIGS. 57 through 64 are computer-generated representations of breasts under floatation. FIG. 57 is a perspective view, FIG. 58 is a side view, FIG. 59 is a top view and FIG. 60 is a view taken from below the breasts. FIGS. 61, 62 and 63 offer additional perspective views, while FIG. 64 provides another side view. All of these computer-generated representations were created using a mold of a patient's breasts while they were under the influence of floatation. The mold was then measured by a three-dimensional sensor and mapped by computer software to produce the images found in FIGS. 57 through 64. These images may be used to manufacture clothing which is custom tailored to an individual's particular shape.

Making a Mold under Floatation for the Manufacture of Articles of Clothing

Figure 65:
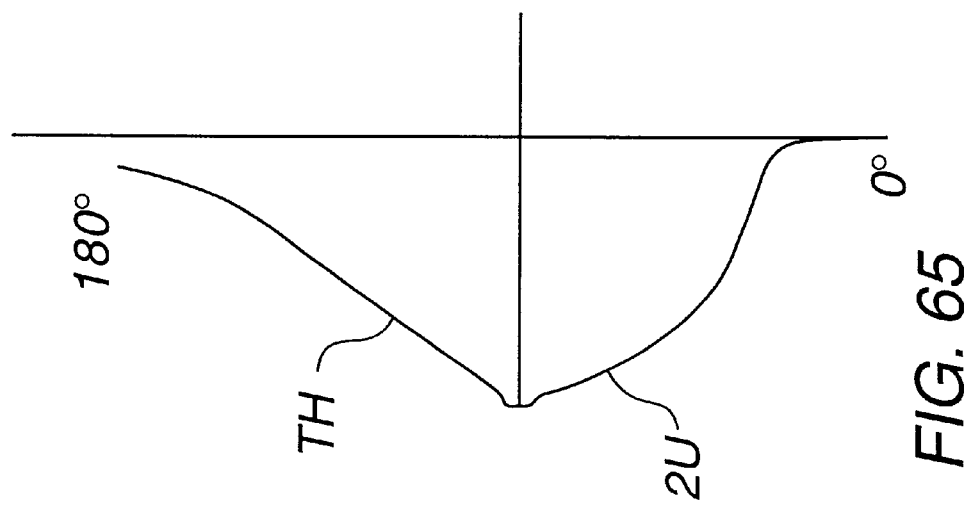

FIG. 65 is a cross-sectional plot of a female breast under floatation while the patient is in a prone position. FIG. 66 is a table that contains bust mold measurements that were obtained by making a three-dimensional mold of the breast shown in FIG. 65. Digitizing measurement equipment was then employed measure the surface of the mold to generate a numerical value for coordinate pairs of elevation and radial position. The lower portion of the cross-sectional plot is located at the zero degree (0) direction, while the upper portion is located at the one hundred and eighty degree (180) direction.

This method of making a mold of the breast under floatation is not only useful for making clothing which fits the natural contours of the breast, but is also a valuable tool for detecting abnormalities. Thickened portions TH of the breast tissue that are normally not readily detectable using conventional examination methods can be sensed using the method of the present invention.

Figure 67:
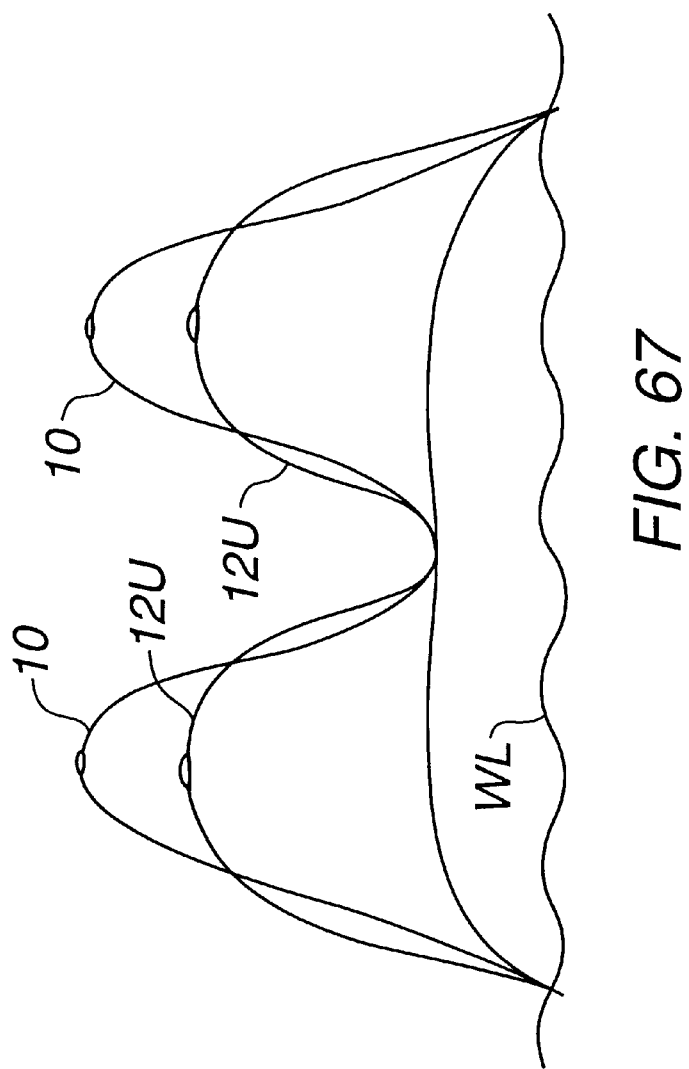
FIG. 67 is an overhead view of a patient in a prone position.

FIG. 67 is a diagram showing a patient partially immersed in water in a prone position from the perspective of an overhead position. The breasts are shown in both the distorted pendular shapes 10 which occur without the effects of floatation, and in their natural "perfect" shapes 12U which occur in the floatation environment.

Figure 68B:
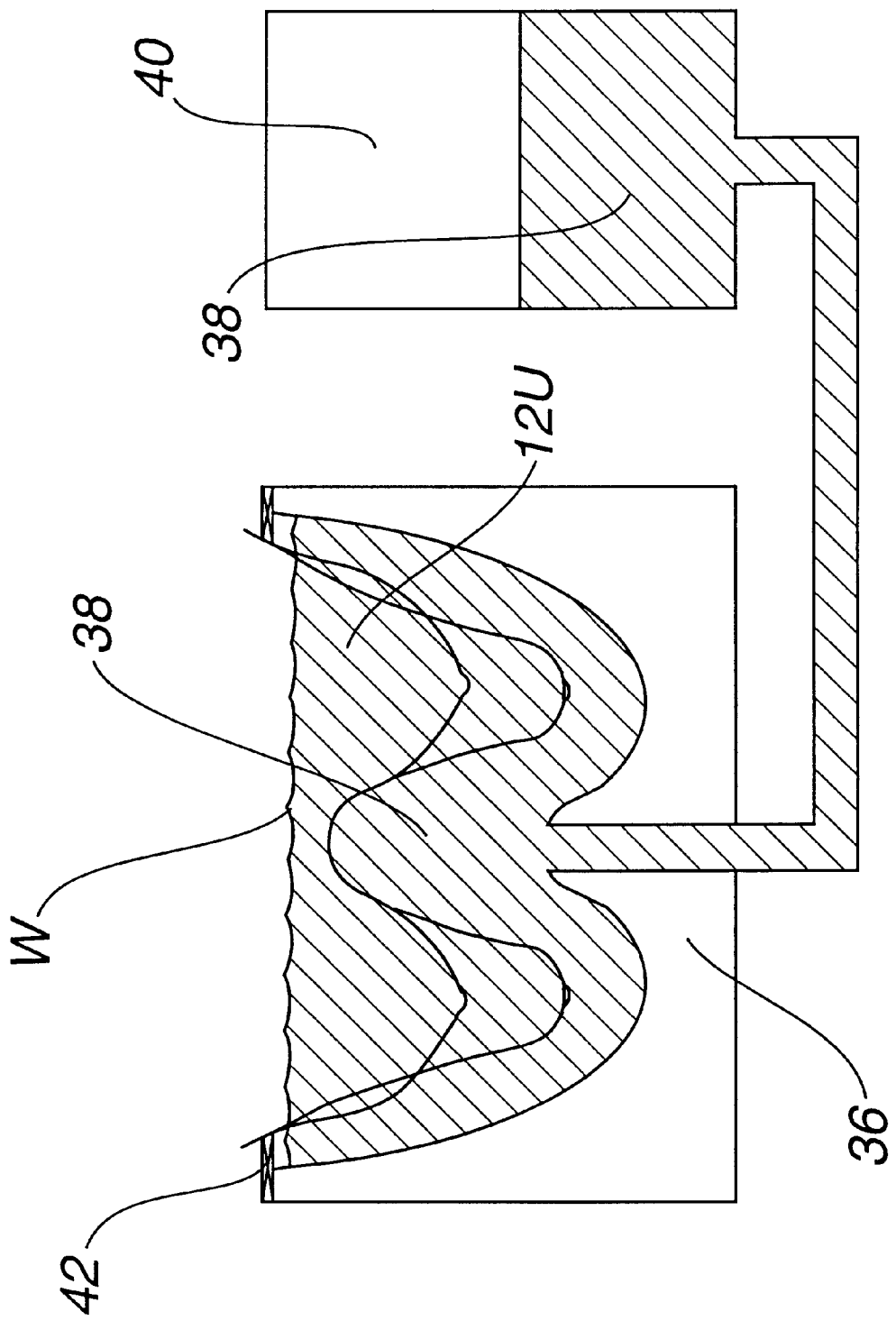
Figure 69:
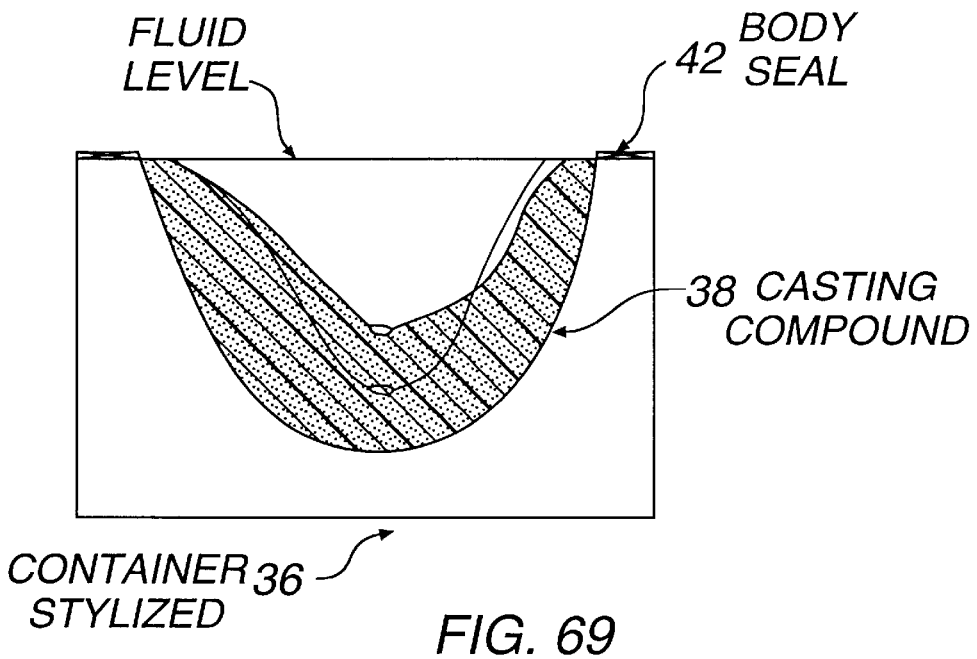
FIG. 69 is a side view of the container shown in FIG. 68A.

FIGS. 68A and 68B illustrate containers 36 that are used to cast molds of female breasts. The container 36 is used to make a bust of the female breasts 12U. During the casting process, the patient is situated in the prone position. A liquid casting compound 38 flows into the container 36 from a reservoir 40. When the casting compound 38 enters the container 36, the breasts are placed under floatation. This causes the breasts to assume a nearly natural shape, since gravity has very little effect. The compound 38 is kept inside the container 36 by body seal 42. FIG. 69 is a side view of the container 36. In a preferred embodiment of the invention, a commercially available casting compound called Earthium Advanced Life Cast™ is utilized to manufacture the mold.

Figure 70:
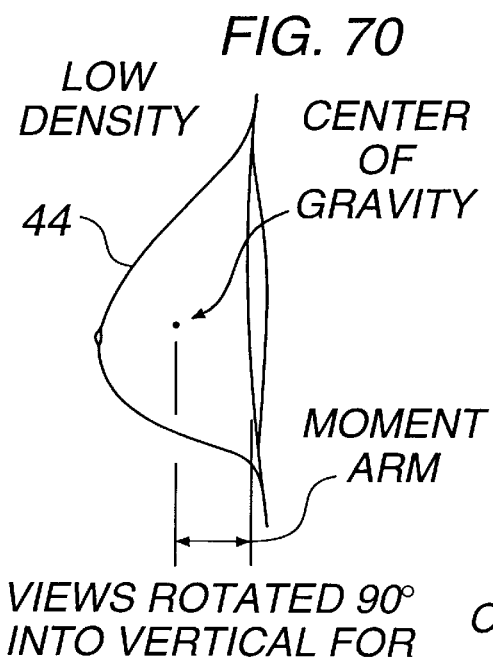
FIGS. 70 and 71 depict profiles of low and high density castings a female breast.
Figure 71:
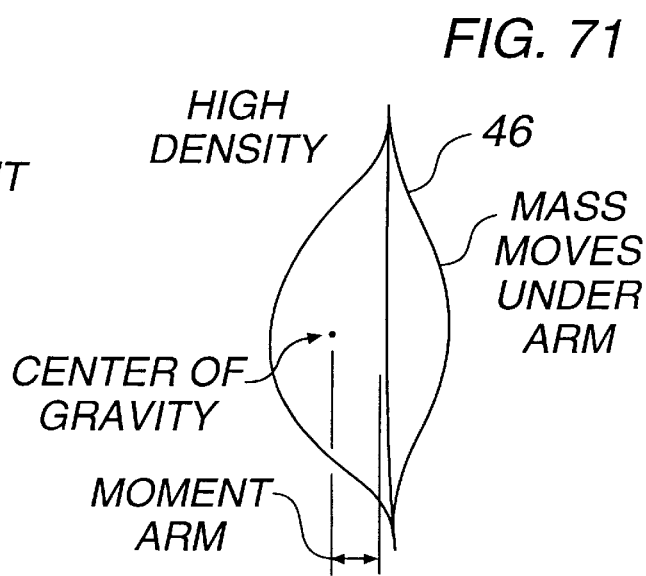

FIGS. 70 and 71 are side views of molds 44 and 46 produced by the casting process illustrated in FIGS. 68A, 68B and 69. The mold 44 shown in FIG. 70 is a "low-density" casting, because the particular mix of casting compound that was used to make this mold 44 had a specific gravity that was less than that of water. The mold 46 shown in FIG. 71 is a "high-density" casting, because the particular mix of casting compound that was used to make this second mold 46 had a specific gravity that was greater than that of water. Different mixtures of casting compounds may be composed to obtain castings of varying densities which, in turn, control the shape of the finished mold. The density and curing time of the completed mold is also affected by the ratios of the casting compound, the water, the water temperature and the catalyst. When the casting has a relatively low density, the breast extends relatively far away from the rib cage, and takes on a somewhat elongated shape. This increases the moment arm to the center of gravity of the breast, and increases the tension on the breast tissue caused by the forces of gravity. Conversely, when the casting has a relatively high density, the breast does not extend as far away from the rib cage, and takes on a more compact shape. The moment arm to the center of gravity of the breast is reduced, and the tension on the breast tissue caused by the forces of gravity are lowered.

Castings having different densities that produce different shapes are useful in detecting abnormalities in the breast tissue. When levitated in the prone position, the internal structure of the breast will seek its most natural position. Any abnormality in the breast tissue will create a distortion or have a protruding effect on the outer surface of the mold.

Castings of different shapes are also useful for producing various articles of clothing which can be custom fit to a particular breast shape. For example, the present invention may be utilized to manufacture a bra which reduces the strain on the breast tissue by reducing the moment arm to the center of gravity of the breast. A bra or breast inserts can be custom-designed to fit individual tastes or needs. The moment arm has a major role in the up and down motion of the breast in walking and running. Providing a custom fit bra contributes to good health and positive self-esteem.

Articles of Clothing

Figure 72:
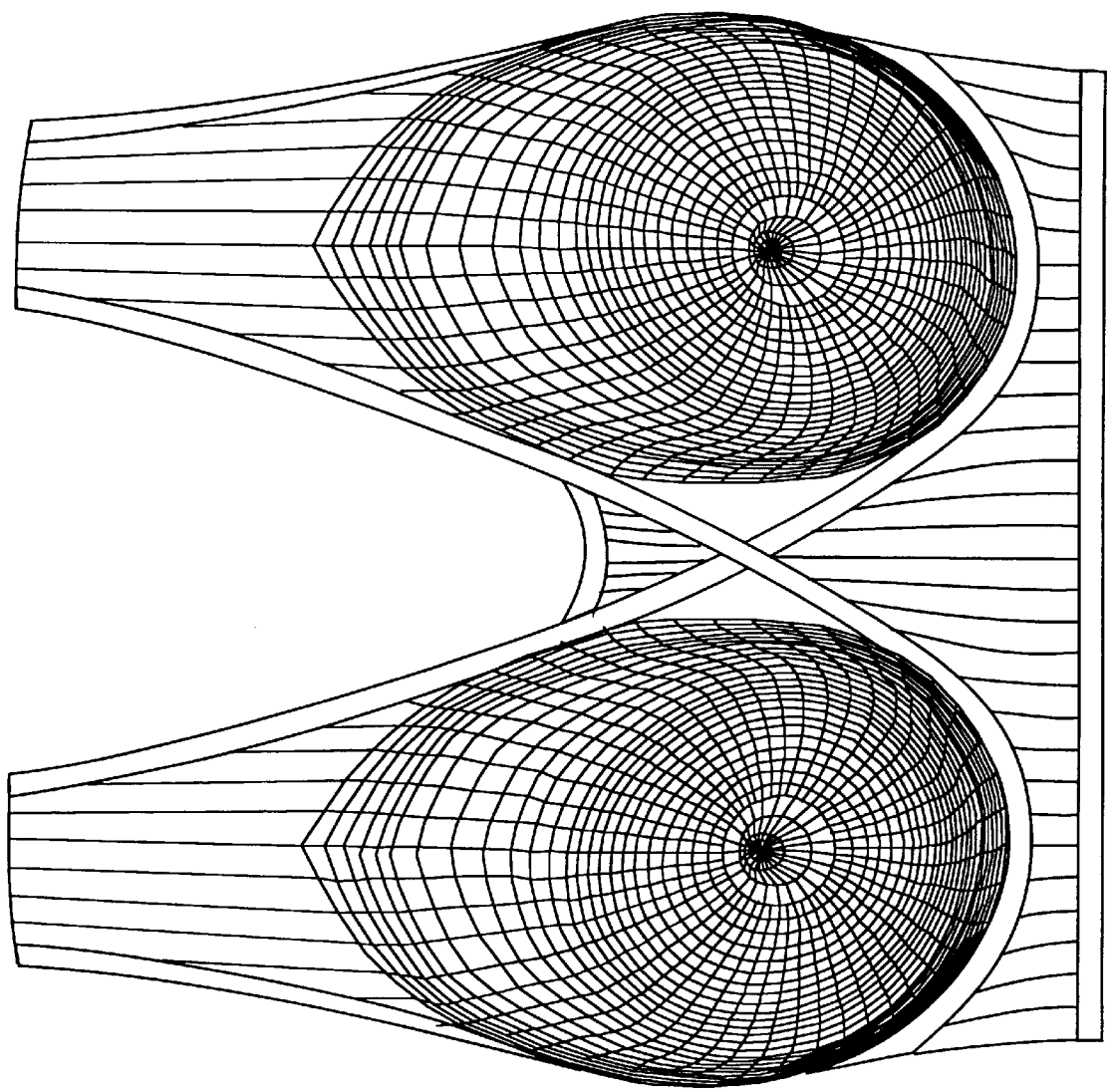
Figure 77:
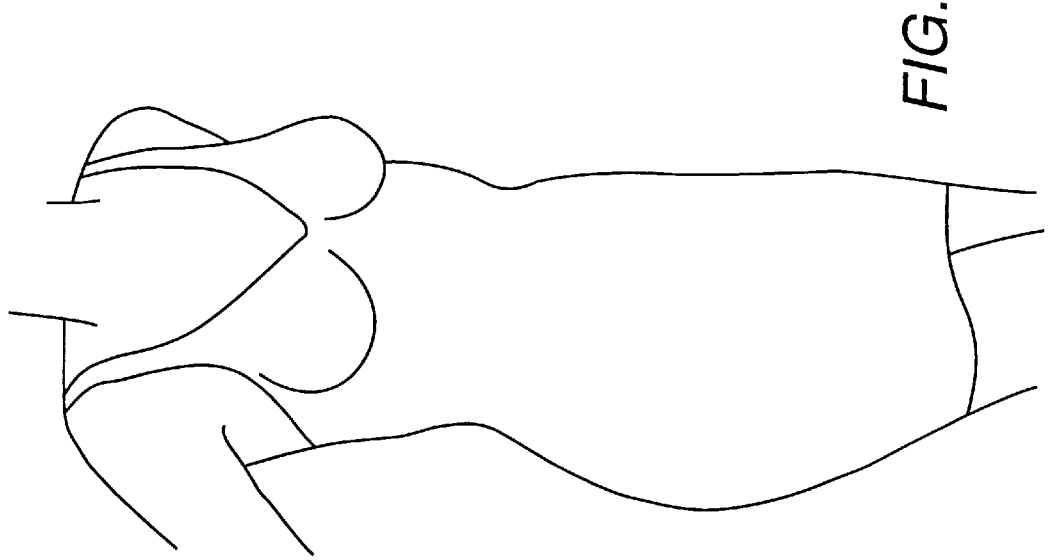
FIG. 77 supplies a contrasting view of a body suit without the Perfect Bra™.
Figure 76:
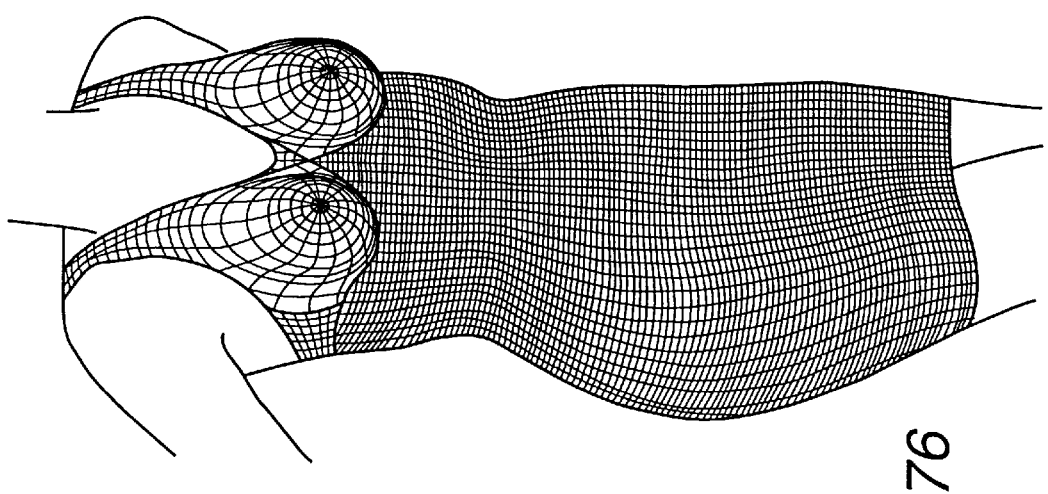
FIG. 76 reveals a body suit incorporating the Perfect Bra™.

FIGS. 72 and 73 furnish front and side views of the Perfect Bra™, while FIGS. 74 and 75 offer comparative views of the Perfect Bra™ and a conventional bra, respectively. FIG. 76 reveals a body suit incorporating the Perfect Bra™. FIG. 77 supplies a contrasting view of a body suit without the Perfect Bra™.

Figure 79:
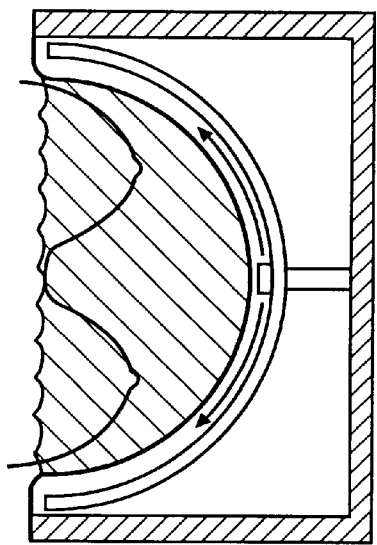
FIGS. 79 and 80 are cross-sectional views of the laser or ultrasound digitizing device shown in FIG. 78.
Figure 80:
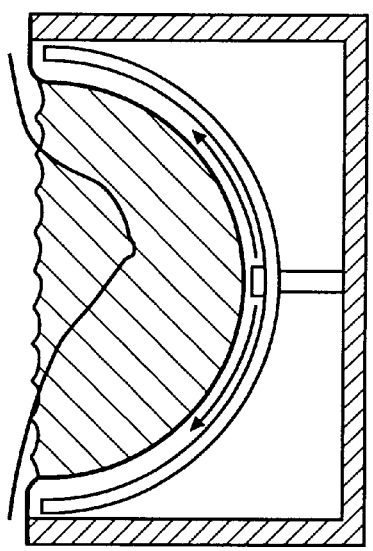
Figure 78:
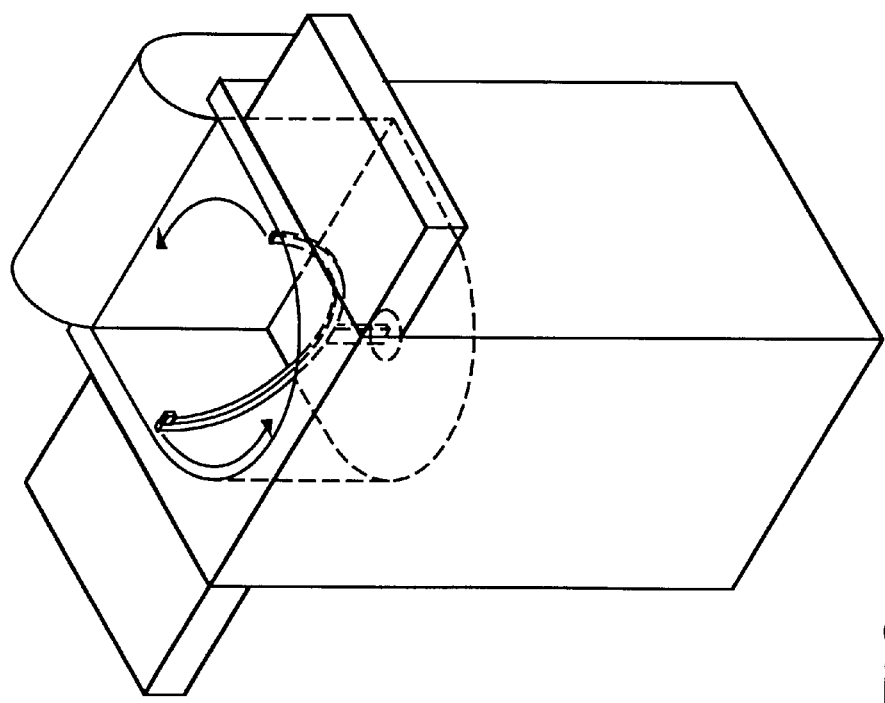
FIG. 78 supplies a perspective view of a laser or ultrasound digitizing device.

FIG. 78 supplies a perspective view of a laser digitizing device. FIGS. 79 and 80 show the digitizing device while it is being used to measure the topography of the breast.

CONCLUSION

Although the present invention has been described in detail with reference to particular preferred and alternative embodiments, persons possessing ordinary skill in the art to which this invention pertains will appreciate that various modifications and enhancements may be made without departing from the spirit and scope of the Claims that follow. The imaging equipment that has been disclosed above is presented to educate the reader about particular embodiments, and is not intended to constrain the limits of the invention or the scope of the Claims. The List of Reference Characters which follows is intended to provide the reader with a convenient means of identifying elements of the invention in the Specification and Drawings. This list is not intended to delineate or narrow the scope of the Claims.

LIST OF REFERENCE CHARACTERS

10 Female breast in normal pendent position
12U Female breast immersed in water under influence of floatation in undeflected position
12D Deflected position of breast during examination
13 Constricted portion of breast
14 Internal structure of breast
16 Spa tub
17 Modular spa facility
18 Shower
20 Schematic block diagram of ultrasonic breast evaluation equipment and circuitry
22 Remote power source
24 Signal conditioner
26 Ultrasonic transducer
28 Signal processor
30 Control panel
32 Glove containing transducer
34 Finger cup
35A Heater and control unit
35B Heated water tubes
35C Heating pad
35D Return tubes
35E Line transformer
35F Well area in pad
35G Gel
35H Fitted heating pads in garment
35I Control unit
35J Lightweight power supply
35K Zipper
35L Pre-heated gel pouch
36 Container
38 Reservoir
40 Casting compound
42 Body seal
44 Low density mold
46 High density mold
F Finger
FF Flat portion of finger
FN Finger nail
FT Finger tip
RC Rib cage
T Torso
W Water
WL Water level

What is claimed is:

1. A method of detecting an abnormality in a portion of the human body comprising the steps of:
    immersing said portion of the human body in a fluid to produce a levitating effect which partially counteracts gravity and allows said portion of the human body to assume a shape less distorted by gravity;
    applying pressure using the finger tips (FT) to form an "S-curve" deflection of said portion of the human body; and
    producing an ultrasound image of said portion of the human body under the levitating influence caused by the immersion of said portion of the human body in said fluid using an ultrasound detector immersed in said fluid.

2. A method as claimed in claim 1, in which said fluid is hot water (W) which relaxes the tissues of said portion of the human body.

3. A method as claimed in claim 2, in which said hot water (W) has a temperature in the range of from 101 to 104 degrees Fahrenheit.

4. A method detecting an abnormality in a portion of the human body comprising the steps of:
    placing a patient in a generally upright position;
    immersing said portion of the human body of said patient in a fluid to produce a levitating effect which partially counteracts gravity and allows said portion of the human body to assume a shape less distorted by gravity;
    applying pressure using the finger tips (FT) to form a "S-curve" deflection of said portion of the human body; and
    producing an ultrasound image of said portion of the human body under the levitating influence caused by the immersion of said portion of the human body in said fluid using an ultrasound detector immersed in said fluid.

5. A method as claimed in claim 1, in which the patient is in a generally upright position and is leaning forward slightly.

6. A method as claimed in claim 1, in which the patient is leaning forward at an angle of approximately five to fifteen degrees.

7. A method as claimed in claim 1, in which the patient is in a supine position.

8. A method as claimed in claim 1, in which the patient is in a prone position.

9. A method detecting an abnormality in a portion of the human body comprising the steps of:

immersing said portion of the human body of said patient in a fluid to produce a levitating effect which partially counteracts gravity and allows said portion of the human body to assume a shape less distorted by gravity;

rotating the rib cage of said patient approximately forty-five degrees from the supine position;

applying pressure using the finger tips (FT) to form a "S-curve" deflection of said portion of the human body; and producing an ultrasound image of said portion of the human body under the levitating influence caused by the immersion of said portion of the human body in said fluid using an ultrasound detector immersed in said fluid.

10. A method detecting an abnormality in a portion of the human body comprising the steps of:

immersing said portion of the human body of said patient in a fluid to produce a levitating effect which partially counteracts gravity and allows said portion of the human body to assume a shape less distorted by gravity;

rotating the rib cage of said patient approximately forty-five degrees from the reclining position;

applying pressure using the finger tips (FT) to form a "S-curve" deflection of said portion of the human body; and producing an ultrasound image of said portion of the human body under the levitating influence caused by the immersion of said portion of the human body in said fluid using an ultrasound detector immersed in said fluid.

11. A method as claimed in claim 1, in which said portion of the human body is an abdomen.

12. A method as claimed in claim 1, in which said portion of the human body includes a male testicle.

13. A method as claimed in claim 1, in which a male abdomen is probed to detect a hernia.

14. A method as claimed in claim 1, in which said portion of the human body is a female breast.

15. A method as claimed in claim 1, comprising the additional step of using a heating pad (35C) to warm said portion of the human body prior to producing an ultrasound image.

16. A method as claimed in claim 1, comprising the additional steps of:

applying a probing pressure using the fingertips (FT); and using said probing pressure to form a relatively constricted three-dimensional projection of tissue to enable the formation of an enhanced ultrasound image.

17. A method as claimed in claim 1, in which the levitating force of said fluid does not push said portion of the human body back against the torso, but lifts said portion of the human body away form the torso.

18. A method as claimed in claim 1, in which said human body is generally substantially immersed in said fluid.

19. A method as claimed in claim 4, in which the patient is in a generally upright position and is leaning forward slightly.

20. A method as claimed in claim 4, in which the patient is leaning forward at an angle of approximately five to fifteen degrees.

21. A method as claimed in claim 4, in which the patient is in a supine position.

22. A method as claimed in claim 4, in which the patient is in a prone position.

* * * * *